US011304903B2

(12) United States Patent
Bayley et al.

(10) Patent No.: US 11,304,903 B2
(45) Date of Patent: Apr. 19, 2022

(54) COMPARTMENTALISED GEL MATRIX AND METHOD OF PRODUCTION

(71) Applicants: Oxford University Innovation Limited, Oxford (GB); Katholieke Universiteit Leuven, Leuven (BE)

(72) Inventors: John Hagan Pryce Bayley, Oxford (GB); Kunwar Tanuj Sapra, Oxford (GB); Giovanni Maglia, Glimmen (NL); Mariam Mohamed Abdelsattar Bayoumi, Heverlee Leuven (BE)

(73) Assignees: Oxford University Innovation Limited, Oxford (GB); Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 16/498,137

(22) PCT Filed: Mar. 27, 2018

(86) PCT No.: PCT/GB2018/050801
§ 371 (c)(1),
(2) Date: Sep. 26, 2019

(87) PCT Pub. No.: WO2018/178654
PCT Pub. Date: Oct. 4, 2018

(65) Prior Publication Data
US 2021/0121402 A1 Apr. 29, 2021

(30) Foreign Application Priority Data
Mar. 27, 2017 (GB) ..................... 1704835

(51) Int. Cl.
*A61K 9/127* (2006.01)
(52) U.S. Cl.
CPC .......... *A61K 9/1275* (2013.01); *A61K 9/1274* (2013.01); *A61K 9/1277* (2013.01)

(58) Field of Classification Search
CPC .. A61K 9/1275; A61K 9/1274; A61K 9/1277; A61K 9/1271; A61K 9/113;
(Continued)

(56) References Cited

U.S. PATENT DOCUMENTS 5,626,870 A * 5/1997 Monshipouri ......... A61K 9/127
264/4.1
6,048,546 A 4/2000 Sasaki et al.
(Continued)

FOREIGN PATENT DOCUMENTS

EP 0199362 A2 10/1986
WO 2005102268 A2 11/2005
(Continued)

OTHER PUBLICATIONS

Baxani, D.K., et al., "Bilayer Networks within a Hydrogel Shell: A Robust Chassis for Artificial Cells and a Platform for Membrane Studies", (2016) Angew. Chem. 55, 14240-14245.
(Continued)

*Primary Examiner* — Gollamudi S Kishore
(74) *Attorney, Agent, or Firm* — Hamilton, Brook, Smith & Reynolds, P.C.

(57) ABSTRACT

The invention provides a compartmentalised gel matrix comprising one or more compartments, wherein each compartment comprises a volume of hydrophobic medium and one or more aqueous droplets therein. The invention further provides a pharmaceutical formulation comprising a compartmentalised gel matrix according to the invention, a synthetic cell comprising a compartmentalised gel matrix according to the invention and a synthetic tissue comprising a compartmentalised gel matrix according to the invention.

24 Claims, 13 Drawing Sheets

(58) Field of Classification Search
CPC .... B01F 3/08; B01F 3/12; C08J 3/075; C12N 11/00; C12N 15/09; G01N 33/483; G01N 33/50
See application file for complete search history.

(56) References Cited

U.S. PATENT DOCUMENTS

| 2010/0062054 | A1* | 3/2010 | Kazakov | A61K 9/5138 424/450 |
|---|---|---|---|---|
| 2012/0022048 | A1 | 8/2012 | Wallace et al. | |
| 2012/0220481 | A1 | 8/2012 | Wallace et al. | |

FOREIGN PATENT DOCUMENTS

| WO | 2013064837 A1 | 5/2013 |
|---|---|---|
| WO | 2014064459 A2 | 5/2014 |

OTHER PUBLICATIONS

Bayley, H., et al., "Droplet interface bilayers", (2008) Mol. BioSyst. 4, 1191-1208.
Blain, J.C., et al., "Progress Toward Synthetic Cells", (2014) Annu. Rev. Biochem. 83, 615-640.
Bodor, N., et al., "Soft Drug Design: General Principles and Recent Applications", P. Med. Res. Rev. 20, 58-101, Dec. 22, 1999.
Booth, M.J., et al., "Light-Activated communication in synthetic tissues", (Apr. 1, 2016) Sci Adv 2, e1600056, 12 pages.
Clavel, F., et al., "HIV Drug Resistance", (2004) J. Med. 350, 1023-1035.
Duarte-Campos, D.F., et al., "Three-dimensional printing of stem cell-laden hydrogels submerged in a hydrophobic high-density fluid", (2013) Biofabrication 5, 015003, 11 pages).
Holden, M.A., "Functional Bionetworks from Nanoliter Water Droplets", (2007) J. Am. Chem. Soc. 129, 8650-8655.
Huang, X., et al., "Interfacial assembly of protein-polymer nano-conjugates into stimulus-responsive biomimetic protocells", (2013) Nat Commun 4, 3239.
Maglio, G., et al., "Anaylsis of Single Nucleic Acid Molecules with Protein Nanopores", (2010) Method. Enzymol. 475, 591-623.
Maglia, G., et al., "Droplet networks with incorporated protein diodes show collective properties", (2009) Nat. Nanotechnol. 4, 437-440.
Notification of Transmittal of International Search Report and the Written Opinion of the International Searching Authority, or the Declaration for International Application No. PCT/GB2018/050801, "Compartmentalised Gel Matrix and Method of Production" dated Jun. 11, 2018.
Notification Concerning Transmittal of International Preliminary Report on Patentability for International Application No. PCT/GB2018/050801, "Compartmentalised Gel Matrix and Method of Production", dated Oct. 1, 2019.
Pouponneau, P., et al., "Co-encapsulation of magnetic nanoparticles and doxorubicin into biodegradable microcarriers for deep tissue targeting by cascular MRI navignation" (2011) Biomaterials 32, 3481-3486.
Sarles, S.A., et al., "Physical encapsulation of droplet interface bilayers for durable, portable biomolecular networks", (2010) Lab on a Chip 10, 710-717.
Search Report for Great Britain Application No. GB1704836.6, "Compartmentalised Gel Matrix and Method of Production", dated Jan. 11, 2018.
Stadler, B., et al., "Polymer hydrogel capsules: en route toward synthetic cellular systems", (2009) Nanoscale 1, 68-73.
Villar, G., et al., "A Tissue-Like Printed Material", (2013) Science 340, 48-52.
Venkatesan, G.A., et al., "Droplet immobilization within a polymeric organogel improves lipid bilayer durability and portability", (2016) Lab on a Chip 16, 2116-2125.
Walsh, C. "Molecular mechanisms that confer antibacterial drug resistance", Nature 406, 775-781 (Aug. 2000).
White, N., "Antimalarial drug resistance and combination chemotherapy", Phil. Trans. R. Soc. Lond. B, 354, 739-749 (1999).
Xu, G., et al., "Strategies for Enzyme/Prodrug Cancer Therapy", Clinical Cancer Research, 7: 3314-3324 (Nov. 2001).

* cited by examiner

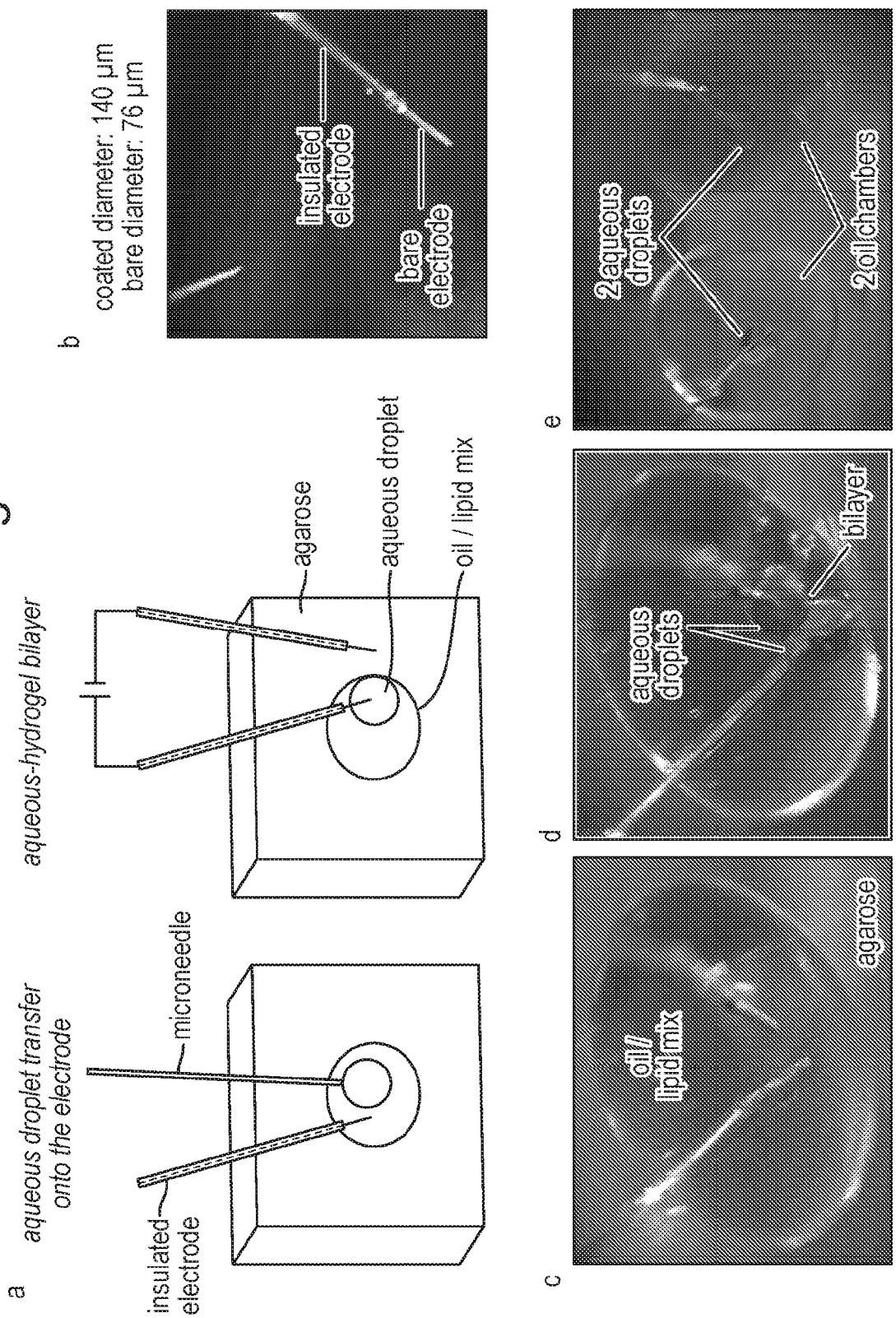

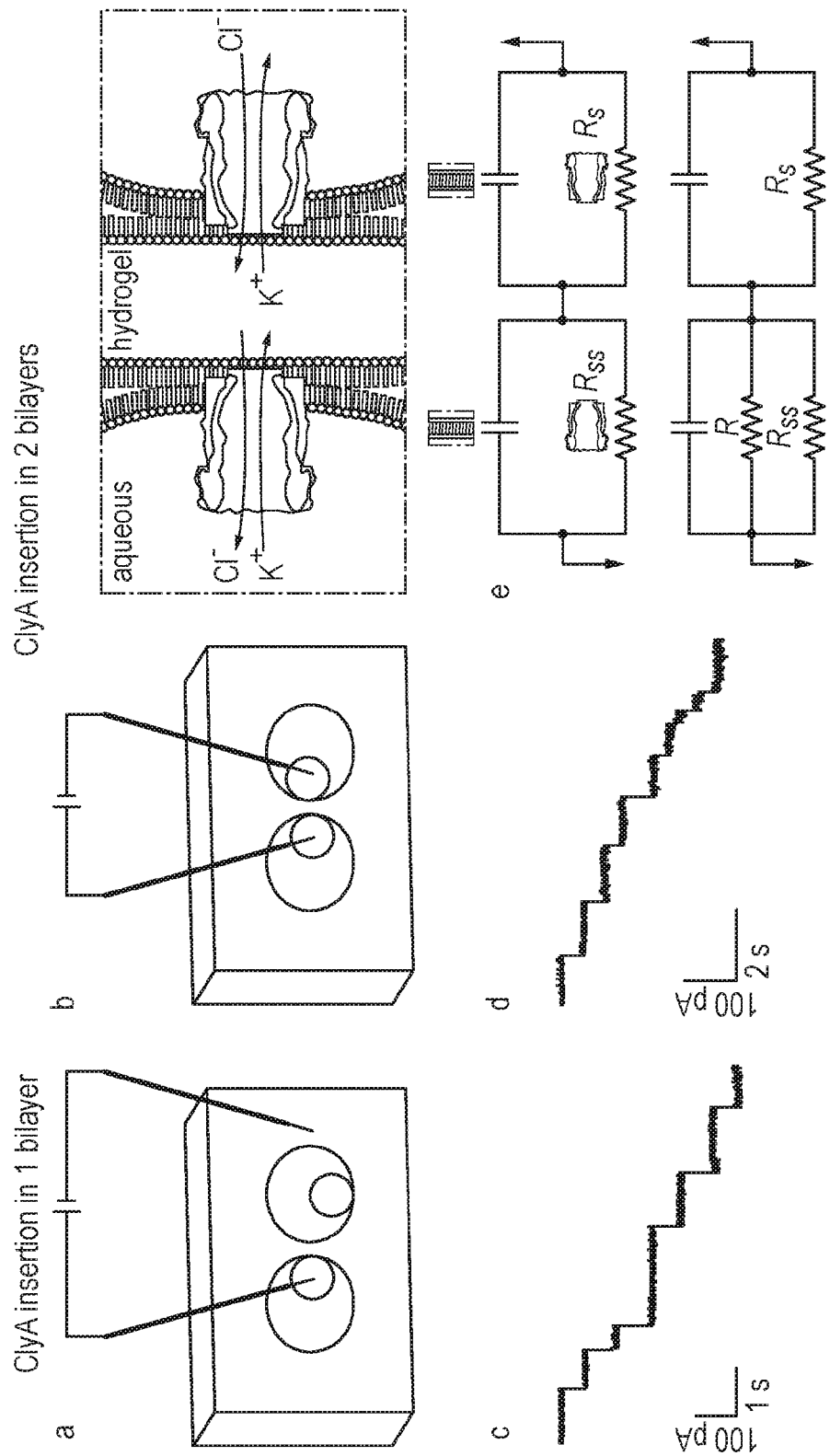

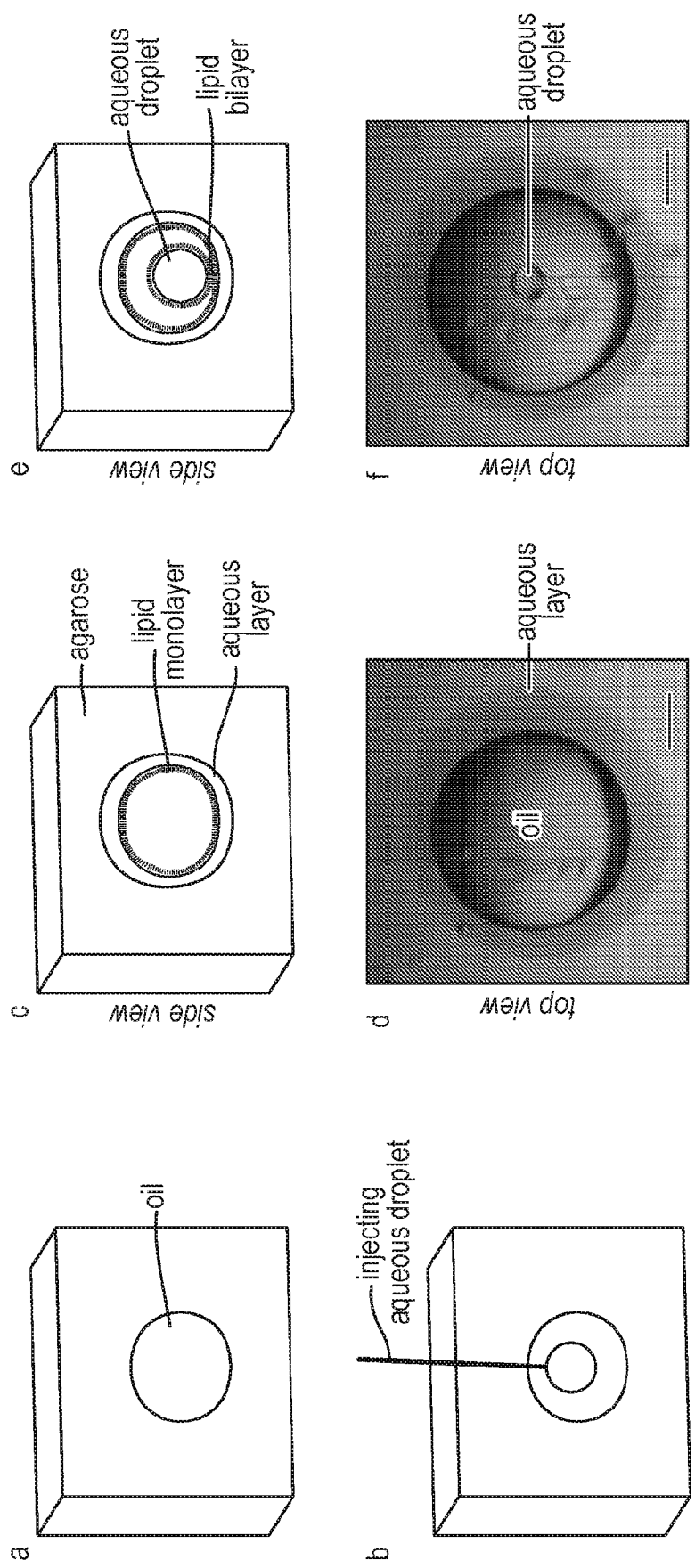

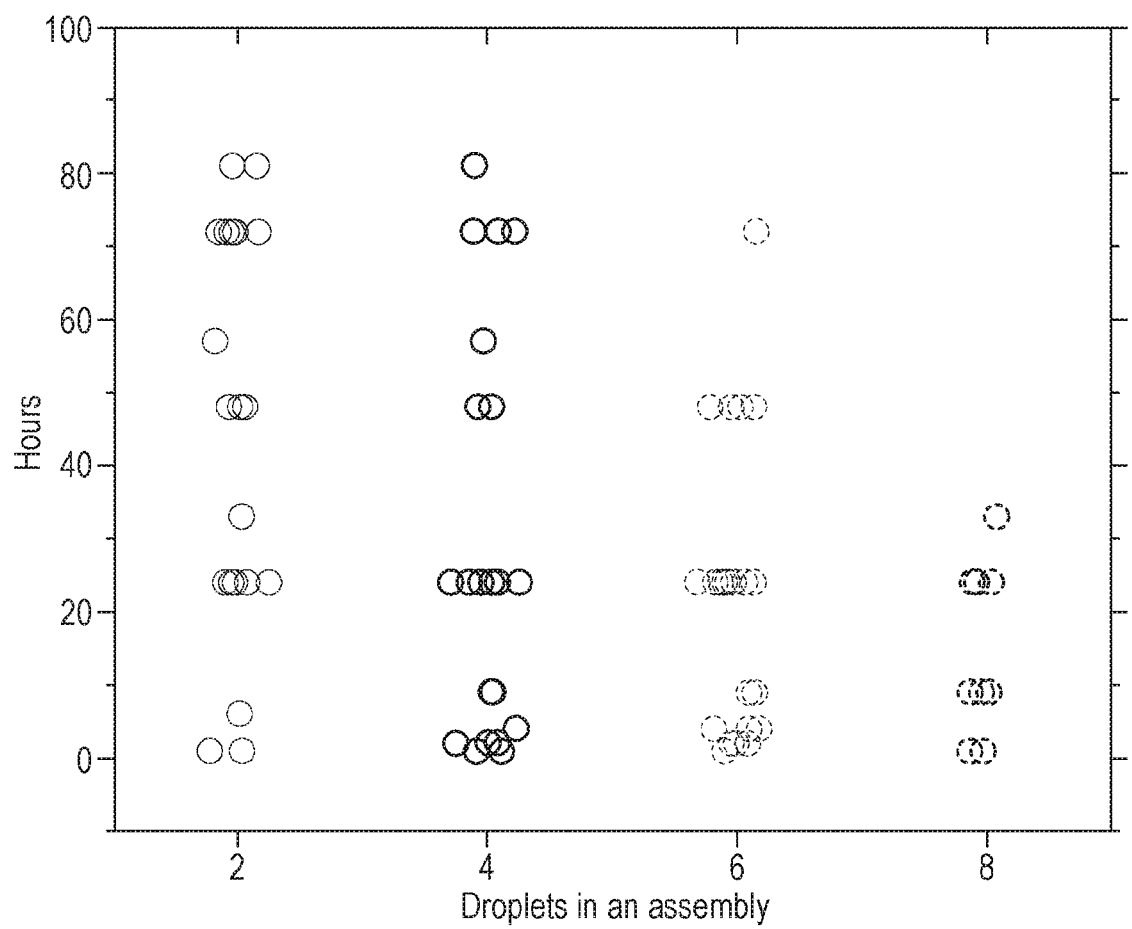

100 # COMPARTMENTALISED GEL MATRIX AND METHOD OF PRODUCTION

RELATED APPLICATIONS

This application is the U.S. National Stage of International Application No. PCT/GB2018/050801, filed Mar. 27, 2018, which designates the U.S., published in English, and claims priority under 35 U.S.C. § 119 or 365(c) to Great Britain Application No. 1704835.6, filed Mar. 27, 2017. The entire teachings of the above applications are incorporated herein by reference.

The work leading to this invention has received funding from the European Union Seventh Framework Programme (FP7/2007 to 2013) under grant agreement no. 236250.

FIELD OF THE INVENTION

The invention relates to a compartmentalised gel matrix. The invention also relates to a pharmaceutical formulation, a synthetic cell and a synthetic tissue comprising the compartmentalised gel matrix. The invention also provides a method for producing the compartmentalised gel matrix. Various possible uses of the compartmentalised gel matrix are described herein.

BACKGROUND TO THE INVENTION

A robust gel matrix having compartments capable of containing and releasing one or more biologically useful agents to its surroundings may have applications in a wide variety of fields. In the case that the compartments comprise layers that mimic cell membranes, the gel matrix has many applications in the field of synthetic biology. In the case that such agents can be released in a controlled manner the gel matrix may be applied in the field of drug delivery. Where the gel matrix contains numerous compartments, complex structures may be obtained.

The success of the biological cell is owed to compartmentalisation. A direct consequence of compartmentalization is chemical and electrical signaling, which are key factors in imparting emergent properties to biological cells and tissues. Consequently, a mandatory feature of a protocell, and the success of its translation into a prototissue, is compartmentalization and communication between its multiple compartments. Like its biological counterpart, enclosing DNA, RNA, and proteins in small volumes of protocells ensures protection from degradation while providing the required concentration for optimal function. For protocellular systems, delimiting the active contents from their environment bestows the possibility of functional engineering by means of spatial and temporal control over the system. It is therefore desirable to provide a robust and stable compartmentalised system for a wide range of uses, including in mimicking biological systems.

A compartmentalised system would be particularly useful in synthetic biology. Synthetic biology seeks to build and tweak cells to understand how life began, functions, and evolves, as well as to engineer and exploit new life forms. One approach to synthetic biology is a top-down approach that involves synthesizing a minimal genetic blueprint, 'creating' a cell, and taming the metabolic pathways for biotechnological applications. However, the present invention is particularly suited to bottom-up synthetic biology, which is focused on the de novo design of a cell with the specific aim of building structures and mimicking complex cellular functions. Toward the realization of synthetic cellular systems, promising success has been achieved in the bottom-up design of a protocell (Blain et al., "Progress toward synthetic cells", *Annu. Rev. Biochem.* 83, 615-640 (2014)), and intriguing possibilities have been demonstrated for a functional prototissue (Villar et al., "A tissue-like printed material", *Science* 340, 48-84 (2013); Booth et al., "Light-activated communication in synthetic tissues", *Sci Adv* 2, e1600056, doi: 10.1126/sciadv.1600056 (2016)).

A number of tools and techniques have been introduced in recent years (e.g. nanometre-sized lipid vesicles, giant unilamellar vesicles, polymersomes, capsosomes, proteinosomes, and vesosomes), as models of biological systems such as protocells and for applications in drug delivery and nanotechnology. Recently, individual aqueous droplets encapsulated in oil have been proposed as simple protocell models. The aqueous droplets (protocells) can be connected to form a bilayer at the contact interface in in an oil/lipid bath. Bilayer-linked aqueous droplets situated in a network are capable of electrical and chemical communication with each other and with the surrounding aqueous medium via protein nanopores. Droplet networks have been shown to exhibit emergent properties of electrical and mechanical nature, which are among the first steps toward a prototissue. The aqueous droplets can be replaced by millimeter-sized hydrogel pieces in oil to give stable bilayers at their interface. However, thus far, neither the vesicular nor the droplet systems have been optimized for designing hierarchical cellular mimics in a bottom-up fashion, i.e., starting from a proto-organelle to a prototissue.

One example of a system comprising aqueous compartments in oil is described in WO 2013/064837 A1. This document describes a droplet encapsulate comprising a drop of hydrophobic medium surrounded by a peripheral layer of non-polymeric amphipathic molecules. The drop contains an aqueous droplet that is itself surrounded by a layer of non-polymeric amphipathic molecules. Another system comprising aqueous compartments in oil is described by Baxani et al., "Bilayer networks within a hydrogel shell: a robust chassis for artificial cells and a platform for membrane studies", *Angew. Chem.* 55, 14240-14245 (2016). This paper describes a microfluidics system whereby aqueous droplets in oil are exposed to a continuous flow of alginate, creating an alginate shell around a portion of oil. The portion of oil contains aqueous droplets. Although useful for encapsulating a specific number of aqueous droplets inside a single oil volume, forming multiple oil compartments may be challenging using this method.

Previously, liposomes and polymersomes have been used to form multiple aqueous droplets encapsulated in hydrogel (Städler et al., "Polymer hydrogel capsules: en route toward synthetic cellular systems", *Nanoscale* 1, 68-73 (2009); Huang et al., "Interfacial assembly of protein-polymer nano-conjugates into stimulus-responsive biomimetic protocells", *Nat Commun* 4, doi:10.1038/ncomms3239 (2013)). However, these nanometer-sized containers are not amenable to spatial control in the structures, nor is it possible to achieve a precise control of their numbers inside the hydrogel. The ability to provide a defined number of aqueous droplets is an important feature of a protocell for a controlled functional output.

SUMMARY OF THE INVENTION

The present invention provides a multi-compartment system comprising aqueous droplets stabilized in a hydrophobic medium, all encapsulated in a gel. The compartments may be in electrical and/or chemical communication with one another. This capability can be enhanced by the formation of a lipid bilayer (at an interface between the hydrophobic medium and an aqueous droplet therein, and/or an interface between the hydrophobic medium its surroundings) and the insertion of membrane proteins in said bilayer. Advantageously, two such bilayers may be adjoined to form a double bilayer. Furthermore, the method of the invention enables the formation of two adjoining lipid bilayers in a controlled manner. The presence of a double bilayer is important for mimicking a functional cell or tissue. Therefore, this platform displays the basic requirements for the realization of a prototissue, and has the potential to be implemented for drug delivery and the construction of biosensors.

An aqueous droplet, stabilized in an oil/lipid bath, inside a gel, may serve as the basic unit for the bottom-up construction of a protocell, and a collection of these as prototissue. The use of a firm gel matrix allows the formation of multiple compartments inside the same gel unit. The stable encapsulation of aqueous droplets in different oil compartments held in the hydrogel enables the formation of two parallel bilayers close to each other—a first step toward engineering organelle and cell mimics for controlled electrical and chemical communication. A major advantage of the present strategy is the ease of hierarchical encapsulation, thereby offering a clear demarcation between a proto-organelle, a protocell and a prototissue. A hierarchical architecture where the number of compartments can be controlled is especially important for engineering linear systems, which can be developed into more complex systems with non-linear outputs.

The compartmentalised and multi-compartmentalised gel matrices of the present invention allow a specified number of compartments of a specified size to be incorporated in gels. Advantageously, the size of each compartment and the size of each aqueous droplet therein may be controlled. Furthermore, the number of aqueous droplets within each compartment may be controlled. The method of manufacturing the compartmentalised and multi-compartmentalised gel matrices of the invention involves simple manual assembly. The solid support provided by the gel and the ease of manual construction of the gel matrix allows a precise control over the number of aqueous droplets and compartments inside the gel.

A compartmentalised gel matrix provides a robust and tunable environment for containing a precisely-defined number of compartments of hydrophobic medium, each having a precisely-defined number of aqueous droplets therein. The relative positions of each compartment may be chosen. Communication between compartments and the aqueous droplets therein may be controlled by the distance between compartments, the nature of the gel between compartments, the presence or absence of membrane proteins joining compartments to the surrounding gel and/or to each other, and so on.

Accordingly, in one aspect the present invention provides a multi-compartmentalised gel matrix comprising a gel matrix and a plurality of compartments, wherein each compartment comprises:
  a volume of a hydrophobic medium;
  an outer layer of amphipathic molecules around the volume of hydrophobic medium;
  an aqueous droplet in the volume hydrophobic medium; and
  an inner layer of amphipathic molecules at an interface between the aqueous droplet and the hydrophobic medium.

Advantageously, one or more compartments within a compartmentalised gel matrix according to the invention may comprise a droplet of hydrophobic medium contained within a layer of aqueous medium. The aqueous medium may, for instance, stabilise an outer layer of amphipathic molecules around the volume of hydrophobic medium.

Accordingly, in another aspect the invention provides a compartmentalised gel matrix comprising a gel matrix and a nested compartment, wherein the nested compartment comprises:
  a volume of a hydrophobic medium;
  an aqueous droplet in the hydrophobic medium;
  an aqueous layer around the volume of hydrophobic medium;
  an inner layer of amphipathic molecules at the interface between the aqueous droplet and the hydrophobic medium; and
  an outer layer of amphipathic molecules at the interface between the aqueous layer and the volume of hydrophobic medium.

The compartmentalised gel matrix and multi-compartmentalised gel matrix of the invention are robust. Their properties and susceptibility to external stimuli may be determined according to the nature of the gel matrix. For instance, the gel matrix may be selected to release its contents in response to a particular environment. Accordingly, the invention provides a pharmaceutical formulation for drug delivery comprising a multi-compartmentalised gel matrix or compartmentalised gel matrix, wherein the compartmentalised or multi-compartmentalised gel matrix comprises an active ingredient. The invention further provides a use of a compartmentalised or multi-compartmentalised gel matrix according to the invention in a method of drug delivery.

In addition to being robust, the compartmentalised gel matrix and multi-compartmentalised gel matrix of the invention allow the simulation of biological systems such as organelles and cells. In particular, the compartments and the aqueous droplets therein in the compartmentalised gel matrix and multi-compartmentalised gel matrix of the invention may communicate with one another, for instance via bilayers, double bilayers or even by diffusion through the gel (mimicking cytoplasm). Communication between separate environments is an important element in mimicking biological systems such as organelles and cells. Synthetic tissues and even synthetic organs may be built from synthetic cells. Accordingly, the invention provides a synthetic cell comprising a multi-compartmentalised gel matrix or compartmentalised gel matrix according to the invention. The invention also provides a synthetic tissue comprising a plurality of synthetic cells. The invention also provides the use of a compartmentalised or multi-compartmentalised gel matrix according to the invention in synthetic biology.

Advantageously, the compartmentalised gel matrix and multi-compartmentalised gel matrix of the invention may be prepared by a convenient and controllable method.

Accordingly the invention provides a method of manufacturing a multi-compartmentalised gel matrix, the method comprising:
  (i) inserting a volume of a hydrophobic medium into an incompletely gelled gel precursor via an inserting means to form a compartment;
  (ii) repeating step (i) one or more times to provide a plurality of compartments in the gel precursor;
  (iii) gelling the gel precursor;

(iv) inserting a volume of an aqueous medium into one of the plurality of compartments via an inserting means to form an aqueous droplet therein; and (v) repeating step (iv) a plurality of times to provide an aqueous droplet in each compartment among the plurality of compartments.

The invention also provides a method of manufacturing a compartmentalised gel matrix comprising a nested compartment, the method comprising:

(i) inserting a volume of a hydrophobic medium into an incompletely gelled gel precursor via an inserting means to form a compartment;

(iii) gelling the gel precursor;

(vi) inserting a quantity of an aqueous medium in or near the volume of hydrophobic medium via an inserting means to form an engulfed volume of hydrophobic medium in a layer of aqueous medium; and (vii) inserting a volume of an aqueous medium into the engulfed volume of hydrophobic medium via an inserting means to form an aqueous droplet therein.

BRIEF DESCRIPTION OF THE FIGURES

FIG. 1 (*i*) shows a protocell, which is a gel matrix comprising multiple proto-organelles (a proto-organelle being an aqueous droplet encased in a volume of oil). FIG. 1 (*ii*) shows a prototissue comprising several protocells. The prototissue consists of a modular gel network, wherein each gel module is a protocell comprising proto-organelles. The expanded portion of FIG. 1 (*ii*) shows a lipid monolayer surrounding the oil and the aqueous droplets, and the formation of a bilayer where the lipid monolayers contact one another. FIG. 1 (*iii*) also shows a prototissue, wherein a single gel piece contains multiple protocells. In FIG. 1 (iii) the protocells are volumes of oil containing multiple aqueous droplets. FIG. 1 (*iv*) illustrates a proto-organ comprising multiple prototissues as shown in FIG. 1 (*iii*).

FIG. 4A shows the set-up for the electrical measurements on bilayers formed by (i) an inner layer of amphipathic molecules at the interface between an aqueous droplet and a volume of hydrophobic medium and (ii) an outer layer of amphipathic molecules around the volume of hydrophobic medium.

FIG. 5 shows that the current flowing between two adjacent bilayers (formed by (i) an inner layer of amphipathic molecules at the interface between an aqueous droplet and a volume of hydrophobic medium and (ii) an outer layer of amphipathic molecules around the volume of hydrophobic medium) depends on the number of Cytolysin A pores present in the bilayers.

FIG. 6 diagrammatically illustrates the formation of a nested compartment (Images a, b, c, e), and contains images of such a nested compartment (Images d, f).

FIG. 7 shows the stability of compartments comprising 2, 4, 6, and 8 aqueous droplets in an oil volume with time. Droplets began to fuse in 1 to 80 hours in compartments comprising two aqueous droplets, and in 1 to 30 hours in compartments comprising 8 aqueous droplets.

DETAILED DESCRIPTION OF THE INVENTION

Figure 1:
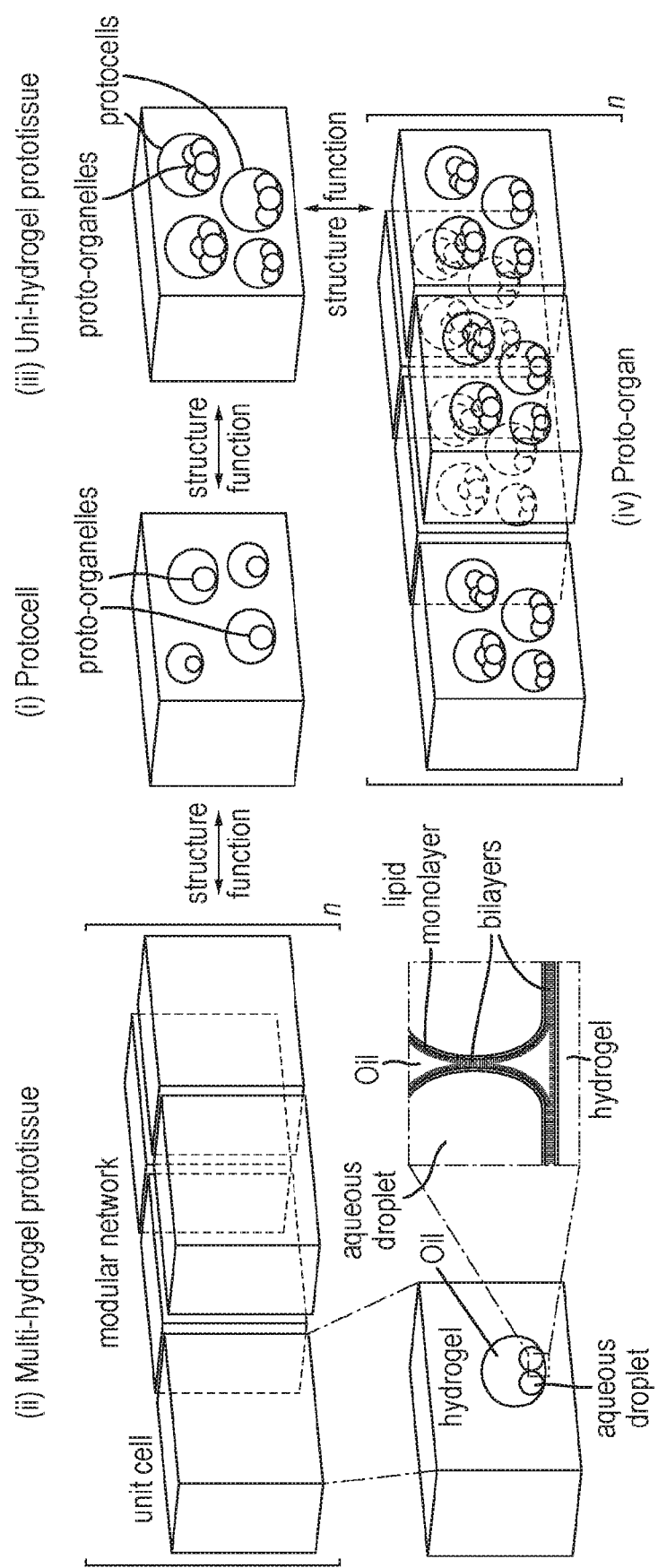
FIG. 1 illustrates the construction of synthetic cells and tissues according to the invention.

As defined above, the invention provides in one aspect a multi-compartmentalised gel matrix comprising a gel matrix and a plurality of compartments, wherein each compartment comprises:

a volume of a hydrophobic medium;

an outer layer of amphipathic molecules around the volume of hydrophobic medium;

an aqueous droplet in the volume hydrophobic medium; and an inner layer of amphipathic molecules at an interface between the aqueous droplet and the hydrophobic medium.

In another aspect, the present invention provides a compartmentalised gel matrix comprising a gel matrix and a nested compartment, wherein the nested compartment comprises:

a volume of a hydrophobic medium;

an aqueous droplet in the hydrophobic medium;

an aqueous layer around the volume of hydrophobic medium;

an inner layer of amphipathic molecules at the interface between the aqueous droplet and the hydrophobic medium; and an outer layer of amphipathic molecules at the interface between the aqueous layer and the volume of hydrophobic medium.

The various features of both of the above-defined aspects of the invention will now be defined and discussed in more detail below.

Multi-Compartmentalised and Compartmentalised Gel Matrix

The invention provides a multi-compartmentalised gel matrix and a compartmentalised gel matrix. The term "compartmentalised" as used herein is taken to mean that the gel matrix comprises one or more compartments. The term "multi-compartmentalised" as used herein is taken to mean that the gel matrix comprises two or more compartments. Thus, the term "compartmentalised" encompasses the term "multi-compartmentalised" and where the term "compartmentalised" is used it should be taken to include the meaning "multi-compartmentalised". Typically, the compartmentalised gel matrix of the invention is a multi-compartmentalised gel matrix.

The term "compartment" as used herein is taken to mean an area within a gel (typically a gel matrix), the composition of which differs from the composition of the surrounding gel matrix. In particular, a compartment may be defined as a volume of hydrophobic medium surrounded by a gel. The compartmentalised gel matrix and multi-compartmentalised gel matrix of the invention comprise compartments each having therein (i) a volume of hydrophobic medium and (ii) an aqueous droplet. However, a multi-compartmentalised gel matrix may also comprise one or more compartments that do not comprise an aqueous droplet. Generally, the or each compartment is within the gel matrix.

A compartment is obtainable by inserting a volume of hydrophobic medium into a gel precursor. The gel precursor is subsequently gelled. This process is described in more detail below. Accordingly a compartment may be present in a gel precursor or in a gel matrix. A compartment may further comprise one or more aqueous droplets within the volume of hydrophobic medium. A compartment may further comprise an aqueous layer surrounding a volume of hydrophobic medium therein. Thus, although a compartment may be described as a volume of hydrophobic medium surrounded by a gel, the volume of hydrophobic medium need not be in direct contact with the surrounding gel.

The shape of a compartment is not particularly limited. However, the shape of a compartment is typically such as may be obtained by injecting a volume of hydrophobic medium into a gel precursor. For example, the compartment may be a rounded or spherical shape, e.g. a droplet.

The size of a compartment is not particularly limited. Typically, the volume of a compartment may be in the range of from 5 µL to 2000 µL, e.g. 50 µL to 1000 µL.

In some embodiments, a compartment is a nested compartment. A nested compartment is a compartment comprising an aqueous layer between the volume of hydrophobic medium in the compartment and the surrounding gel matrix. The term "compartment" as used herein should be taken to encompass the term "nested compartment".

The multi-compartmentalised gel matrix of the invention may comprise a plurality of compartments, none of which are nested compartments. Alternatively, one or more compartments within the multi-compartmentalised gel matrix of the invention may be nested compartments. In one embodiment, all of the compartments within a multi-compartmentalised gel matrix of the invention are nested compartments.

Gel Matrix

The term "gel matrix" as used herein is taken to mean a volume of a material comprising a gel which is gelled. The term "gel matrix" is taken to refer to the gel part of both a compartmentalised gel matrix and a multi-compartmentalised gel matrix according to the invention.

The gel matrix may have a fixed shape. The shape of the gel matrix is not particularly limited. The gel matrix may be in the form of a bulk or a block. Typically, the shape of the gel matrix is determined by the shape of a mould in which it is formed. Exemplary shapes for the gel matrix include a cuboid, a cube, a spheroid, a sphere, a cylinder, or a sheet.

The gel matrix may have a fixed volume. The volume of the gel matrix is not particularly limited. However, the volume of the gel matrix is sufficient to encapsulate one or more compartments of hydrophobic medium. Typically the volume of the gel matrix is at least 0.1 ml, preferably at least 1 ml.

The gel matrix comprises a gel. A gel may be defined as a "nonfluid colloidal network or polymer network that is expanded throughout its whole volume by a fluid". The nonfluid component of a gel, which is capable of forming the gel when expanded with a fluid, is referred to herein as a gel-forming agent. The gel-forming agent may, for instance, be polymeric or colloidal. A gel therefore comprises a network of the gel-forming agent which is expanded throughout its volume (i.e. swelled) by the fluid. The process of forming a gel from the fluid and the gel-forming material is referred to as "gelling".

A gel precursor material is a medium that has not yet fully gelled, comprising the gel-forming agent and the fluid. A gel precursor is therefore typically flowable. Gel is formed by the gelling of a gel precursor material. When a gel matrix comprises both gel and gel precursor material, the gel matrix may be described as "incompletely gelled". When a gel matrix does not comprise (i.e. no longer comprises) gel precursor material it is "fully gelled". The extent of gelling of the gel matrix is such that the gel matrix is firm (for instance, the gel matrix is not flowable). In particular, the gel matrix is sufficiently gelled that it is impermeable to hydrophobic media such as oil. For example, the gel matrix is sufficiently gelled that a volume of hydrophobic medium (e.g. oil) inserted into the gel matrix will not escape from the gel matrix. The volume of hydrophobic medium (e.g. oil) will typically remain intact in the gel matrix for an hour or more, preferably for a day or more. Preferably the gel matrix is fully gelled.

The nature of the gel, and of the gel particles from which a gel may be formed, is not particularly limited. However, preferably the gel comprises a hydrophilic material. This is preferable so that when a volume of hydrophobic medium comprising amphipathic molecules is present in the gel, the amphipathic molecules will assemble in a monolayer wherein the hydrophilic groups of the amphipathic molecules are subject to attractive interactions with the gel in order to enable the formation of a monolayer such as a lipid monolayer.

An exemplary gel which may be used is a hydrogel, for instance agarose gel, a gelatin hydrogel or a gelatin methacrylate hydrogel. A hydrogel may be defined as "a gel in which the swelling agent (i.e. the fluid) is water". A hydrogel is produced by the gelling of a gel precursor material that is an aqueous solution of a gel-forming agent. In the case of a hydrogel, the gel-forming agent may be referred to herein as a hydrogel compound. Any suitable hydrogel compound may be employed. The hydrogel compound is typically polymeric. For instance, the hydrogel compound may be a polysaccharide, a polyvinyl alcohol, a polyacrylate, a polymer comprising a number of hydrophobic groups or a derivative thereof. The hydrogel compound is typically a polysaccharide. Examples of hydrogel compounds include agarose, methylcellulose and hyaluronan. Preferably, the hydrogel compound is agarose, gelatin or gelatin methacrylate. More preferably, it is agarose. The gel-forming agent may therefore be a gel-forming agent which comprises agarose. The gel-forming agent which comprises agarose may, for instance, be agarose.

Hydrogels are particularly advantageous when used in the gel matrix of the invention because of their tunable material properties, such as their mechanical properties. The stiffness of the hydrogel is an example of a property of a hydrogel which may be varied or tuned. Mechanical properties (such as stiffness) can be tuned by adjusting parameters such as the nature and concentration of gel-forming agent compound, the nature and concentration of cross-linking agent (if present) and other parameters as would be well understood by the skilled person. Thus, in some embodiments the invention relates to a compartmentalised or multi-compartmentalised gel matrix wherein the gel matrix comprises hydrogel and has a specified stiffness. The ability to determine the mechanical properties of the gel matrix is useful as, for instance, it allows the resistance of the gel matrix to mechanical wear and tear to be adjusted.

An example of a gel which is suitable for creating gel matrices having tunable mechanical properties (particularly stiffness) is polyacrylamide gel. Polyacrylamide gel is well-suited to the formation of gel matrices of tunable stiffness owing to the ease of tuning the cross-linking in polyacrylamide gel. Thus, in some embodiments the compartmentalised or multi-compartmentalised gel matrix of the invention comprises polyacrylamide gel.

The ability to tune the mechanical properties of the gel matrix is particularly advantageous where the gel comprises, or is intended to comprise biological cells. This is because cells behave differently on materials of different stiffnesses. Accordingly the behaviour of cells in the gel matrix may be controlled by tuning the stiffness of the gel matrix. Thus, in some embodiments the invention relates to a compartmentalised or multi-compartmentalised gel matrix wherein the gel matrix comprises a hydrogel and further comprises a plurality of biological cells.

Another exemplary gel which may be used is a DNA gel. By "DNA gel" is meant a gel comprising a DNA molecule. Thus, in some embodiments, the gel of the gel matrix is a DNA gel.

Accordingly the invention provides a compartmentalised or multi-compartmentalised gel matrix wherein the gel comprises a hydrogel. In some embodiments, the invention provides a compartmentalised or multi-compartmentalised gel matrix wherein the gel consists of hydrogel.

The concentration of the gel-forming agent (for example a hydrogel compound) in the fluid (which may, for example, be an aqueous medium, such as water or cell-growth medium) is typically from 0.01 mg/L to 500.0 mg/L. For instance, the concentration of the gel-forming agent in the fluid may be from 0.1 mg/L to 100.0 mg/L, or from 0.5 mg/L to 30.0 mg/L.

Another example of a gel is a matrix of crosslinked colloids. In this instance, the gel-forming agent which is used to form the gel comprises crosslinkable colloid particles, and the gel precursor material from which the gel is formed is a suspension comprising crosslinkable colloid particles. Other examples of gels include gels comprising polymers which may be cross-linked by photoinitiated polymerisation, or by thermally-induced polymerisation.

The gel may be biological in origin. For instance, the gel may comprise collagen derived from animals. Another example of a biologically-derived gel is Matrigel. Biologically-derived gels may be particularly suitable for forming gel networks which support biological cells. In some embodiments, the invention provides a compartmentalised or multi-compartmentalised gel matrix wherein the gel comprises a biocompatible gel.

Alternatively or additionally, the gel may comprise biological material. Thus, in some embodiments, the gel may comprise one or more proteins. In some embodiments, the gel may comprise one or more of an extracellular matrix, fibrinogen, fibronectin or collagen.

Preferably the gel matrix comprises a hydrogel. Preferably, the gel precursor material from which the gel is formed therefore comprises the gel-forming agent (which may be referred to as a hydrogel compound) and water. The gel precursor material from which the gel is formed may therefore be an aqueous medium. The aqueous medium typically comprises at least 80% water by weight, for example at least 90% water by weight.

Another exemplary gel is a polymer which is covalently cross-linked. Covalent cross-linking is typically photoinitiated, e.g. by ultraviolet light, or thermally initiated, e.g. by heating. In this instance, the gel-forming agent comprises non-cross-linked polymer, and the gel precursor material comprising the gel-forming agent may be any liquid comprising non-cross-linked polymer.

In addition to gel (and, when present, gel precursor material), a gel matrix may comprise other materials, compounds or substances. For instance, the gel matrix may contain at least one small molecule, such as a dye. Suitable dyes include, but are not limited to, pyranine. In some embodiments, the gel matrix may comprise an active agent. The term "active agent" a used herein is an agent which has an effect on or in the human or animal body, such as a therapeutic agent or a diagnostic agent. Exemplary active agents are discussed in more detail below, in the section entitled "uses of the compartmentalised gel matrix". In some embodiments, the gel matrix may be functionalised with the active agent, e.g. covalently bound to the active agent. The active agent may be a therapeutic agent, such as a prodrug, or a diagnostic agent, such as a contrast agent.

Thus, the invention provides a compartmentalised or multi-compartmentalised gel matrix comprising an active agent. The invention further provides a compartmentalised or multi-compartmentalised gel matrix wherein the gel is functionalised with an active agent. In some embodiments, the invention provides a compartmentalised or multi-compartmentalised gel matrix wherein the gel is a hydrogel and the hydrogel is functionalised with an active agent.

In some embodiments, a gel matrix may comprise biological compounds, or a mixture of biological compounds. By "biological compound" is meant a compound which may be found in vivo, for example in the human body. Examples of biological compounds include proteins, e.g. enzymes. Mixtures of biological compounds include, for example, gastric juices.

In another embodiment, the gel matrix may comprise biological cells. The term "biological cell", as used herein, is well known and refers to a cell comprising a cytoplasm (typically comprising organelles such as a nucleus or a ribosome) enclosed within a membrane. The biological cells may be prokaryotic or eukaryotic. The biological cells are typically eukaryotic. The biological cells may be naturally occurring or genetically (or otherwise) modified. Often, the biological cells are mammalian cells derived from mammalian tissue, for instance mouse, rat, sheep or human tissue. For instance, the biological cells may be derived from primate tissue such as human or chimpanzee tissue. In some embodiments, the one or more biological cells are selected from two or more different types of biological cells.

A type of a biological cell refers to the cell type of a biological cell taken from a particular species. For instance, typical examples of mammalian biological cell types include mouse embryonic fibroblasts (MEFs), HeLa cells, cells of cell lines derived from HeLa cells, Jurkat cells, induced pluripotent stem cells, human embryonic kidney (HEK) cells, osteoblast cells, chrondrocyte cells and mesenchymal stem cells.

Thus, the invention provides a compartmentalised or multi-compartmentalised gel matrix wherein the gel matrix comprises biological cells. The said cells may be present within the gel itself, in addition or alternatively to being in one or more compartments.

In some embodiments of the invention, the composition of the gel matrix may be chosen to react to an external stimulus. In particular, the composition of the gel matrix may be designed to become more permeable or lose its form in response to an external stimulus. By "become more permeable" is meant that that the gel matrix may allow volumes of hydrophobic medium to move therethrough more easily. For instance, the gel matrix may allow hydrophobic media such as oil to permeate it more easily such that they do not remain trapped therein. In one embodiment, the term "lose its form" means to become incompletely gelled, for example to dissolve. In another embodiment, the term "lose its form" means to break. When a gel matrix is broken, its fixed shape changes. A gel matrix may break in response to a mechanical stimulus. The composition of the gel matrix may therefore be chosen to be "soft", (that is, easily breakable) or "hard" (that is, not easily breakable).

When a compartmentalised or multi-compartmentalised gel matrix becomes more permeable or loses its form, it may release the contents of one or more of its compartments (and in particular any active agents therein) to the environment. Accordingly the contents of one or more compartments may be exposed to the environment. For example, the aqueous medium in an aqueous layer or in an aqueous droplet within a compartment may flow out of the gel matrix and into the environment.

In the event that the compartmentalised or multi-compartmentalised gel matrix breaks, one or more compartments therein may be opened, meaning that they are no longer surrounded by a continuous shell of gel. For example, substantially all of the compartments may open, e.g. all of the compartments in a compartmentalised or multi-compartmentalised gel matrix may open when the gel matrix breaks. Where a compartment is broken or opened, it is likely that the layer or layers of amphipathic molecules therein may also break (e.g. rupture) and release the contents into the environment. By "rupture" herein is meant rupture irreversibly so that the entire contents of the layer of amphipathic molecules are released into the environment. Thus, in some embodiments, a compartmentalised or multi-compartmentalised gel matrix will release the contents of its compartment(s), including the hydrophobic and aqueous media in the compartments therein, to the environment on breaking.

In some embodiments (such as where the gel matrix becomes more permeable or dissolves) the compartments of the gel matrix may be exposed in a manner such that one or more layers of amphipathic molecules therein are not ruptured. In some embodiments, therefore, when the gel matrix becomes more permeable or loses its form, the outer layers of amphipathic molecules surrounding the volumes of hydrophobic medium in one or more compartments are not ruptured. Similarly, in some embodiments, when the gel matrix becomes more permeable or loses its form, the inner layers of amphipathic molecules surrounding one or more aqueous droplets within one or more compartments are not ruptured. In some embodiments, when the gel matrix becomes more permeable or loses its form, one or more bilayers in one or more compartments are not ruptured (bilayers are discussed in more detail below). Typically, where one or more layers of amphipathic molecules remains intact when the gel matrix loses its form or becomes more permeable, the release of the contents of said layers to the environment is delayed. For example, said contents may be released only after a further external stimulus, or only after additional time has passed. Where one or more layers of amphipathic molecules remains intact, the release of the contents of that layer to the environment will be controlled by that layer of amphipathic molecules.

The external stimulus which causes a compartmentalised or multi-compartmentalised gel matrix to break or lose its form is typically temperature or pH. However, other suitable stimuli that may be used include but are not limited to ultrasound; a mechanical stimulus (e.g. pressure); shear flow; a critical concentration of a species (e.g. a critical concentration of divalent cations); and electromagnetic radiation (light), including but not limited to infrared, UV, X-rays and gamma rays. In one aspect of this embodiment, the external stimulus may be temperature. In this aspect, the composition of the gel matrix is chosen to give the gel matrix temperature-dependent properties. For instance, the gel matrix may become more permeable or lose its form on heating, e.g. when placed in warm water or hot water. In another aspect of this embodiment, the external stimulus may be pH. In this aspect, the composition of the gel matrix may be chosen to give it pH-dependent properties. For instance, the gel matrix may become more permeable or lose its form on exposure to acid. An exemplary acid in this regard is stomach acid or hydrochloric acid. In another aspect of this embodiment, the external stimulus may be an ionic trigger. In this aspect, the composition of the gel matrix may be chosen to give it properties that depend on the ionic concentration of its surroundings. For instance, the gel matrix may become more permeable or lose its form on exposure to high or low ionic concentrations. On becoming more permeable or losing its form, the gel matrix may release the contents of any compartments therein to its surroundings.

In some embodiments of the invention, the gel matrix comprises regions of differing composition. Typically, the regions of differing composition in such a gel matrix comprise a first region and a second region, the first region having a composition which is different from that of the second region. Thus, the invention provides a compartmentalised gel matrix or a multi-compartmentalised gel matrix wherein the gel matrix comprises two or more gel regions. The invention further provides a compartmentalised gel matrix or a multi-compartmentalised gel matrix wherein the gel matrix comprises two or more gel regions wherein the said gel regions each comprise different gels.

The first region may for instance comprise a material, for instance a compound, which is absent from the second region, and/or the second region may comprise a material, for instance a compound, which is absent from the first region. Additionally or alternatively, the first and second regions may both comprise a particular material, for instance a particular compound, but at different concentrations. For instance, the concentration of the material (e.g. compound), in the first region may be at least twice the concentration of the material (e.g. compound) in the second region. The concentration of the material (e.g. compound), in the first region may for instance be at least ten times, for example at least 100 times, at least 1,000 times, or at least 1,000,000 times, the concentration of the material (e.g. compound) in the second region.

As will be described further below, the material (or compound) in question may for instance be a particular gel, a particular gel-forming agent, biological cells, a particular type of biological cell, or a particular small molecule compound. The material may for instance be a therapeutic agent, diagnostic agent, biological compound (for instance a protein or enzyme or nucleic acid, for instance a membrane protein, e.g. a membrane pore protein) or biological cells (e.g. mammalian cells, for example mammalian cells selected from human embryonic kidney (HEK) cells, osteoblast cells, chrondrocyte cells and mesenchymal stem cells; or for instance bacteria, for example bacteria which are commonly found in or on the human body, for instance gut bacteria).

The regions of differing composition may further comprise a third region, the third region having a composition which is different from that of the first region and also different from that of the second region. The composition of the third region may differ from that of the first or second region as defined above for difference between the first and second regions.

The location of the one or more compartments within a compartmentalised or multi-compartmentalised gel matrix having multiple gel regions is not particularly limited. For instance, where the gel matrix is a multi-compartmentalised gel matrix the compartments may be located only in one gel region, or in some but not all of the gel regions, or in all of the gel regions.

A multi-compartmentalised gel matrix may having multiple gel regions may comprise different varieties of compartments in each of the different gel regions. For example, a first gel region in the gel matrix may comprise compartments of a first composition and a second gel region in the gel matrix may comprise compartments of a second composition. Alternatively, different varieties of compartment may be distributed through the gel regions at random.

In a gel matrix comprising regions, the regions of differing composition may be located adjacent to one another, for example the regions may be arranged in layers. Alternatively, the regions of differing composition may comprise one region within (i.e. encapsulated by or surrounded by) another region.

Typically, the regions of differing composition within a gel matrix have differing physical properties. For example, the differing regions of the gel matrix may comprise different kinds of gel, for example different kinds of polymer e.g. different kinds of hydrogel. There are numerous advantages associated with using different kinds of gel. For example, differing gels may be compatible with different components. For instance, a gel formed from a hydrophilic polymer may be unable to carry a salt, but able to carry biological cells, and thus in order to incorporate both components into a single gel matrix, it may be convenient to create a gel matrix having regions comprising different kinds of gel.

The differing regions of gel may have differing responses to external stimuli. As discussed above, a gel matrix may release the contents of compartments therein to its surroundings in response to an external stimulus. Where the gel matrix comprises different gel regions, these regions may for instance be sensitive to the same stimulus and the compartments in all the regions may therefore be capable of releasing their contents simultaneously upon exposure to that stimulus. In other embodiments, two or more gel regions may have different stabilities, and the compartments therein may therefore be capable of releasing their contents into the environment at different times, in response to different stimuli, or for instance in response to different levels or magnitudes of the same stimulus. For example, a first compartment in a first gel region may be capable of releasing its contents in response to a change in pH, whereas a second compartment in a second gel region may be capable of releasing its contents in response to a change in temperature.

Alternatively, compartments within two or more gel regions within the same gel matrix may release their contents in response to different levels of the same stimulus. Thus, for example, a first compartment in a first gel region may be capable of releasing its contents in response to a relatively small change in pH or temperature, whereas a second compartment in a second gel region may only release its contents in response to a larger change in pH or temperature.

One area where a gel matrix having different regions with different properties may be useful is in drug delivery. For example, a compartmentalised or multi-compartmentalised gel matrix carrying a particular active agent such as a therapeutic agent may be coated in a gel region chosen to ensure a suitable time of release (referred to as a "timed-release formulation"). In another example of a timed-release formulation, a multi-compartmentalised gel matrix may comprise multiple gel regions designed to release the contents of compartments therein at different times, ensuring a particular dosage pattern from a single administration. Accordingly, the invention provides a pharmaceutical formulation comprising a compartmentalised or multi-compartmentalised gel matrix according to the invention. The invention further provides a pharmaceutical formulation comprising a compartmentalised or multi-compartmentalised gel matrix according to the invention wherein the pharmaceutical formulation is a timed-release formulation.

The Hydrophobic Medium

Each compartment in the compartmentalised and multi-compartmentalised gel matrices of the invention comprises a volume of hydrophobic medium. The hydrophobic medium may be selected from a wide range of materials. Suitable hydrophobic media are described in WO 2013/064837 A1, the entire contents of which is incorporated herein by reference. The hydrophobic medium may comprise a single hydrophobic compound. Alternatively, it may comprise a mixture of two or more different hydrophobic compounds. The medium is hydrophobic so that the aqueous droplet or droplets in the compartment remain encapsulated in droplet form, rather than mixing with the hydrophobic medium, but otherwise the hydrophobic medium can be freely chosen. The hydrophobic medium can be selected to affect the buoyancy of the aqueous droplet or droplets in the compartment and the speed of formation of the inner layer of amphipathic molecules around the aqueous droplet or droplets when preparing the compartmentalised gel matrix. Furthermore the hydrophobic medium can be chosen for its compatibility with a particular active agent, such as a therapeutic agent or a diagnostic agent.

The hydrophobic medium in the compartments of the invention is typically an oil. The oil may be a single, pure, compound, or the oil may comprise a mixture of two or more compounds. Any type of oil is suitable, as long as its interfacial tension with the hydrophilic media of the aqueous droplets and the surrounding gel matrix is high enough to prevent the spontaneous disintegration of the oil and aqueous droplets, and as long as it does not destabilize the formed bilayers.

The oil may for instance comprise silicone oil (for instance poly phenyl methyl siloxane). The oil may consist of a single silicone oil, for instance poly phenyl methyl siloxane. Alternatively, the oil may comprise a mixture of two or more different silicone oils.

Additionally or alternatively, the oil may comprise a hydrocarbon. When the oil comprises a hydrocarbon it may comprise a single hydrocarbon compound, or a mixture of two or more hydrocarbons. For example, the oil may comprise hexadecane.

In some embodiments, the oil is a mixture comprising: (a) one or more hydrocarbons, and (b) one or more silicone oils.

When the oil comprises a hydrocarbon, the hydrocarbon may be branched or unbranched, for example a hydrocarbon having from 5 to 30 carbon atoms, or from 5 to 20 carbon atoms (although hydrocarbons of lower molecular weight would require control of evaporation). Preferably, the hydrocarbon is a liquid at the operating temperature of the compartmentalised or multi-compartmentalised gel matrix of the invention. Suitable examples include alkanes or alkenes, such as hexadecane, decane, pentane or squalene. Usually, the oil comprises a hydrocarbon.

Typically the hydrocarbon is an unsubstituted $C_{10}$-$C_{20}$ alkane, for instance hexadecane. In some embodiments the hydrocarbon is a longer-chain hydrocarbon, such as an unsubstituted $C_{15}$-$C_{20}$ alkane.

Other types of oil are possible. For example the oil may be a fluorocarbon. This might be useful for the study of some systems, for example to minimise loss of a particular membrane protein or analyte from the volume of hydrophobic medium or to control gas content such as oxygen.

Typically, the oil comprises silicone oil or a hydrocarbon. Any suitable silicone oil may be employed.

The hydrocarbon typically has from 5 to 20 carbon atoms (a $C_5$-$C_{20}$ hydrocarbon), more typically from 10 to 20 carbon atoms (a $C_{10}$-$C_{20}$ hydrocarbon). Typically, it is an alkane or an alkene. Thus, the hydrocarbon may be a $C_5$-$C_{20}$ alkane, or a $C_{10}$-$C_{20}$ alkane. In another embodiment, the hydrocarbon may be a $C_5$-$C_{20}$ alkene, or a $C_{10}$-$C_{20}$ alkene. The hydrocarbon is typically unsubstituted. In a preferred embodiment, the hydrocarbon is an unsubstituted $C_5$-$C_{20}$ alkane, preferably an unsubstituted $C_{10}$-$C_{20}$ alkane. The hydrocarbon may for instance be squalene, hexadecane or decane. In one embodiment it is squalene. However, in some embodiments the hydrocarbon may be substituted with a halogen atom, for instance bromine.

In some embodiments, the hydrophobic medium comprises a mixture of silicone oil and a hydrocarbon. Such mixtures have been found to provide advantageously low incubation times for stable multisomes to be formed. The silicone oil and hydrocarbon in the mixture may be as further defined above. Typically, the hydrocarbon is an unsubstituted $C_{10}$-$C_{20}$ alkane, preferably hexadecane. The silicone oil typically has a density close to that of water; it may for instance be poly phenyl methyl siloxane. Usually, the volume ratio of the silicone oil to the hydrocarbon is equal or greater than 1:2. The volume ratio of the silicone oil to the hydrocarbon may for instance be from 1:1 to 10:1, for instance about 1:1 or about 3:1.

In one embodiment, the hydrophobic medium comprises both silicone oil and hexadecane. Typically the silicone oil is poly phenyl methyl siloxane. The volume ratio of the silicone oil to the hexadecane is typically equal or greater than 1:1, for instance from 1:1 to 10:1. It may for instance be about 1:1, or about 3:1.

Accordingly, the invention provides a compartmentalised or multi-compartmentalised gel matrix wherein the hydrophobic medium comprises an oil. In other embodiments, the invention provides a compartmentalised or multi-compartmentalised gel matrix wherein the hydrophobic medium consists of an oil.

In some embodiments, the hydrophobic medium may comprise a small molecule, such as a dye. In some embodiments, the hydrophobic medium may comprise amphipathic molecules. In some embodiments, the hydrophobic medium may comprise an active agent. The active agent may be a therapeutic agent, such as a prodrug, or a diagnostic agent, such as a contrast agent. Where the hydrophobic medium comprises an active agent, the agent is typically lipophilic.

Thus, the invention provides a compartmentalised or multi-compartmentalised gel matrix wherein an active agent is present within the hydrophobic medium.

The hydrophobic medium in each compartment within a multi-compartmentalised gel matrix may be the same or different. For example, the hydrophobic medium in each compartment within the multi-compartmentalised gel matrix may be the same.

A compartment according to the invention comprises a volume of hydrophobic medium. The hydrophobic medium in each compartment may be the same or different. The volume of hydrophobic medium in each compartment is not particularly limited, except that it must fit within the volume of the gel matrix. The volume of hydrophobic medium in a compartment is typically or the order of tens or hundreds of microliters. For example, the volume of hydrophobic medium in each compartment may be from 5 to 1000 µL, preferably 10 to 500 µL, more preferably 50 to 200 µL.

The Aqueous Medium

The compartments in the compartmentalised and multi-compartmentalised gel matrices of the invention comprise a droplet of aqueous medium inside the volume of hydrophobic medium. However, it should be noted that a multi-compartmentalised gel matrix may in addition comprise compartments which do not contain aqueous droplets.

In one aspect of the invention, one or more compartments further comprises an aqueous layer around the volume of hydrophobic medium. The aqueous droplet and the aqueous layer may be composed of the same aqueous medium. Alternatively, they may be composed of different aqueous media. The composition of the aqueous media forming the aqueous droplet and/or the aqueous layer are described below.

The aqueous medium may be pure water. Alternatively, the aqueous medium may be an aqueous solution, for instance an aqueous buffer solution. The aqueous solution may be freely chosen for the purpose or use of the compartmentalised or multi-compartmentalised gel matrix, or for the experiment to be performed using the compartmentalised or multi-compartmentalised gel matrix. For instance, the aqueous medium may be chosen for its compatibility with an active agent therein, such as a therapeutic or diagnostic agent.

One important property of the aqueous medium is pH and this can be varied over a wide range. In some embodiments, for instance, the pH of the aqueous medium within the aqueous droplet or droplets may be in the range of from 5 to 9 (or for instance in the range of from 6 to 8) although higher and lower pHs are also possible. The aqueous medium may therefore be an aqueous buffer solution. Any suitable buffer can be employed, depending on the desired pH. The buffer solution may for instance comprise Tris HCl, with KCl, and EDTA. In some embodiments the pH of the aqueous buffer solution is from 5 to 9, or for instance from 6 to 8. The nature and concentration of the solutes can be varied to vary the properties of the solution.

In some embodiments, the aqueous medium may comprise a small molecule, such as a dye. Suitable dyes include, but are not limited to, pyranine. In some embodiments, the aqueous medium may comprise amphipathic molecules. In some embodiments, the aqueous medium may comprise an active agent. The active agent may be a therapeutic agent, such as a prodrug, or a diagnostic agent, such as a contrast agent. Where the aqueous medium comprises an active agent, the agent is typically hydrophilic, for example it may be water-soluble.

Thus, the invention provides a compartmentalised or multi-compartmentalised gel matrix wherein an active agent is present within the aqueous medium.

Aqueous Droplets

Each compartment may comprise one or more aqueous droplets within a volume of hydrophobic medium. Each aqueous droplet comprises an aqueous medium, and each aqueous droplet is surrounded by an inner layer of amphipathic molecules. The aqueous medium of each droplet in the compartment may be the same or different.

In some embodiments, each compartment within a compartmentalised or multi-compartmentalised gel matrix of the invention comprises at least one aqueous droplet. However, also envisaged are embodiments wherein not all of the compartments within a multi-compartmentalised gel matrix comprise aqueous droplets. In some embodiments, a multi-compartmentalised gel matrix according to the invention comprises a plurality of aqueous droplets in at least one of the compartments. In some embodiments, some or all of the compartments within a multi-compartmentalised gel matrix comprise a plurality of aqueous droplets.

Figure 3:
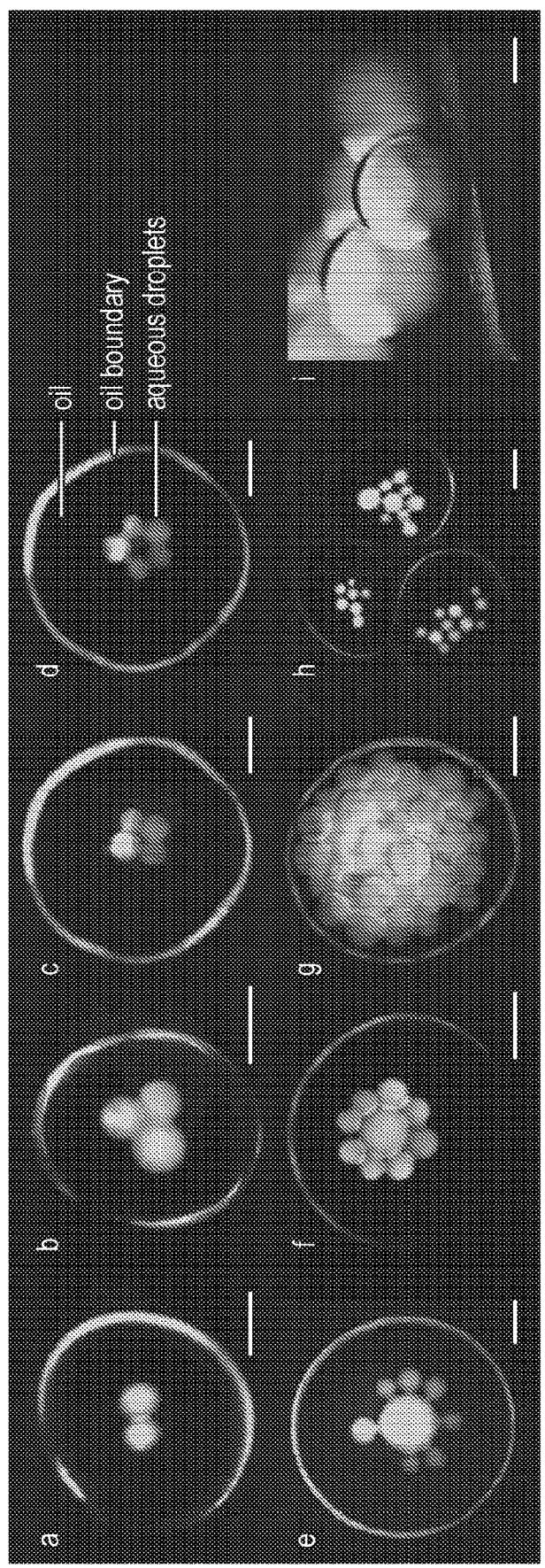
FIG. 3 shows assemblies of aqueous droplets in oil volumes within a hydrogel bulk.

The number of aqueous droplets in each compartment is not particularly limited. For example, Image (g) in FIG. 3 shows a compartment comprising over 40 aqueous droplets. Typically, the number of aqueous droplets in each droplet is from 1 to 500, for instance from 2 to 250, e.g. 2 to 100.

The volume of each aqueous droplet is not particularly limited, except that it must fit within the volume of hydrophobic medium. Where a compartmentalised or multi-compartmentalised gel matrix comprises multiple aqueous droplets, the volume of each aqueous droplet may be the same or different. Where a compartment has within it multiple aqueous droplets, the volume of each aqueous droplet therein may be the same or different. For Example, Images (e) and (h) in FIG. 3 demonstrate a single compartment comprising a plurality of droplets of differing sizes. Typically, the volume of each aqueous droplet is of the order of nanolitres. For example, the volume of each aqueous droplet may be from 1 nL to 1 µL, preferably from 5 nL to 500 nL, more preferably from 10 nL to 200 nL.

An aqueous droplet within a compartment according to the invention may adopt various configurations within the compartment. In some embodiments, part of the inner layer of amphipathic molecules around the aqueous droplet is in contact with another layer of amphipathic molecules and forms a bilayer. In embodiments where the inner layer of amphipathic molecules around the aqueous droplet does form part of a one or more bilayers, where one such bilayer also includes part of an outer layer of amphipathic molecules around a volume of hydrophobic medium the aqueous droplet is said to be in contact with the edge of the hydrophobic medium.

Aqueous Layer

The volume of the aqueous layer is much larger than the volume of an aqueous droplet. For instance, the volume of the aqueous layer may be of the order of tens or hundreds of microliters, e.g. from 10 to 1000 µL, preferably from 50 to 800 µL.

The aqueous layer may have zero thickness in places. That is, the part of the surface of the volume of hydrophobic medium within the aqueous layer may be in contact with the gel matrix.

Amphipathic Molecules

The compartmentalised gel matrix and multi-compartmentalised gel matrix of the invention comprise amphipathic molecules. Amphipathic molecules are distributed in an inner layer at the interface between an aqueous droplet and a surrounding volume of hydrophobic medium. Amphipathic molecules are also distributed in an outer layer around a volume of hydrophobic medium. The outer layer of amphipathic molecules may be at an interface between a volume of hydrophobic medium and an aqueous layer, or between a volume of hydrophobic medium and a gel matrix.

In some embodiments of the invention, the outer layer of amphipathic molecules in at least one of the compartments of a compartmentalised or multi-compartmentalised gel matrix is at an interface between the gel matrix and the volume of hydrophobic medium.

In general, the amphipathic molecules can be of any type which is capable of forming a bilayer consisting of the inner layer and outer layer of amphipathic molecules. This is dependent on the nature of the hydrophobic medium and the aqueous medium (in the aqueous droplets and optionally also in the aqueous layer), but a wide range of amphipathic molecules are possible. Amphipathic molecules are molecules which have both hydrophobic and hydrophilic groups. Preferably, the amphipathic molecules are non-polymeric.

An important class of amphipathic molecules which can be used in the compartmentalised or multi-compartmentalised gel matrix of the invention is lipid molecules. The lipid molecules may be any of the major classes of lipid, including phospholipids, fatty acids, fatty acyls, glycerolipids, glycerophospholipids, sphingolipids, sterol lipids, prenol lipids, saccharolipids and polyketides. Some important examples include phospholipids and fatty acids. The lipid molecules may be naturally occurring or synthetic. Whilst the formation of a bilayer from lipid molecules has been demonstrated the method is expected to be appropriate for any amphipathic molecules capable of forming a bilayer.

A common class of hydrophobic group that may be present in an amphipathic molecule is a hydrocarbon group, as for instance in most lipids. However, another suitable kind of hydrophobic group that may be employed is a fluorocarbon group. Thus, a further important class of amphipathic molecule is an amphipathic molecule that comprises at least one fluorocarbon group. An example of such a molecule would be a lipid-like molecule which comprises a hydrophobic fluorocarbon tail and a hydrophilic head group.

The amphipathic molecules in each compartment need not be all of the same type. Rather, the amphipathic molecules may in some embodiments be a mixture of two or more different kinds of amphipathic molecule. Another important example is that the amphipathic molecules in the respective outer layers of different volumes of hydrophobic media in the gel matrix may be of different types so that double bilayer(s) formed between the different compartments may be asymmetric. Similarly, the amphipathic molecules that form the inner and outer layer within a compartment need not be of the same type so that a bilayer formed of these two layers may be asymmetric.

Typically, therefore, the amphipathic molecules in the compartmentalised and multi-compartmentalised matrix of the invention comprise lipid molecules. The lipid molecules need not be all of the same type. Thus, the amphipathic molecules in each compartment may comprise a single type of lipid or a mixture of two or more different lipid molecules. Also, the lipid composition of an outer layer of a volume of hydrophobic medium may be the same as or different from that of the inner layer at the interface between the volume of aqueous medium and an aqueous droplet. When more than one aqueous droplet is present in a compartment, the lipid compositions of the inner layers of amphipathic molecules surrounding each aqueous droplet may be the same as or different from one another, and the same as or different from the lipid composition of the outer layer. Lipid molecules are particularly advantageous because lipid bilayers, or more generally bilayers of amphipathic molecules, are models of cell membranes and the compartmentalised and multi-compartmentalised gel matrices of the invention therefore serve as excellent platforms for a range of experimental studies, including for instance as proto-organelles, and, in a hierarchical arrangement as protocells, prototissues and proto-organs for "bottom-up" synthetic biology.

Phospholipids are particularly preferred for reasons outlined above and also because they are a major component of all cell membranes, making compartments comprising phospholipids particularly suitable for synthetic biology applications, as well as for drug delivery.

Accordingly, the amphipathic molecules in the compartmentalised and multi-compartmentalised gel matrix of the invention typically comprise phospholipid molecules. The phospholipid molecules may be the same or different, i.e. the amphipathic molecules in each compartment may comprise a single kind of phospholipid, or a mixture of two or more different phospholipids. Phospholipids are well known to the skilled person and many are commercially available, from suppliers such as Avanti Polar Lipids. The phospholipid molecules may be glycerophospholipids or phosphosphingolipids or a mixture of the two. The phospholipid molecules may comprise anionic phospholipids, phospholipids comprising primary amines, choline-containing phospholipids and/or glycosphingolipids. Usually, the amphipathic molecules comprise one or more glycerophospholipids. As the skilled person will appreciate, glycerophospholipids include, but are not limited to glycerophospholipids having a structure as defined in the following formula (I):

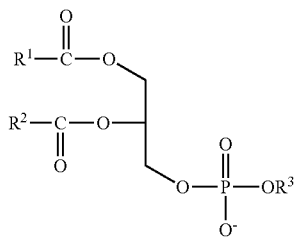

(I)

wherein:

$R^1$ and $R^2$, which are the same or different, are selected from $C_{10}$-$C_{25}$ alkyl groups and $C_{10}$-$C_{25}$ alkylene groups;

either $R^3$ is absent such that $OR^3$ is $O^-$, or $R^3$ is present and is H, $CH_2CH_2N(R^4)_3^+$, a sugar group, or an amino acid group; and each $R^4$, which is the same or different, is independently selected from H and unsubstituted $C_1$-$C_4$ alkyl.

Typically, when $R^3$ is $CH_2CH_2N(R^4)_3^+$, each $R^4$, which is the same or different, is selected from H and methyl. As the skilled person will appreciate, when each and every $R^4$ is methyl, the $R^3$ group is a choline group, and when each and every $R^4$ is H, the $R^3$ group is an ethanolamine group.

When $R^3$ is an amino acid group it may for instance be a serine group, i.e. —$CH_2CH(NH_2)(COOH)$. When $R^3$ is a sugar group, it may for instance be glycerol, i.e. —$CH_2CHOHCH_2OH$, or for instance inositol, i.e. —$CH(CHOH)_5$.

Typical examples of $R^1$ and $R^2$ groups are $C_{10}$-$C_{25}$ alkyl groups, including, but not limited to linear $C_{10}$-$C_{25}$ alkyl groups such as, for instance, $CH_3(CH_2)_{10}$—, $CH_3(CH_2)_{12}$—, $CH_3(CH_2)_{14}$—, $CH_3(CH_2)_{16}$—, $CH_3(CH_2)_{18}$—, $CH_3(CH_2)_{22}$— and branched $C_{10}$-$C_{25}$ alkyl groups such as for instance —$CH_2$—$CH(CH_3)$—$(CH_2)_3$—$CH(CH_3)$—$(CH_2)_3$—$CH(CH_3)$—$(CH_2)_3$—$CH(CH_3)_2$.

Further typical examples of $R^1$ and $R^2$ groups are unsubstituted $C_{10}$-$C_{25}$ alkylene groups, including, but not limited to, $CH_3(CH_2)_5CH=CH(CH_2)_7$—, $CH_3(CH_2)_7CH=CH(CH_2)_7$—, $CH_3(CH_2)_4CH=CHCH_2CH=CH(CH_2)_7$—, $CH_3(CH_2)_4(CH=CHCH_2)_3CH=CH(CH_2)_3$—, and $CH_3CH_2CH=CHCH_2CH=CHCH_2CH=CH(CH_2)_7$—.

As the skilled person will appreciate, the $O^-$ group in the phosphate group adjacent the $OR^3$ group may in some embodiments be protonated, or associated with a suitable cation, for instance a metal cation such as $Na^+$.

Thus, the amphipathic molecules may comprise one or more glycerophospholipids having the structure of formula (as defined above).

For instance, the amphipathic molecules may comprise any one or more of the following glycerophospholipids: 1,2-diphytanoyl-sn-glycero-3-phosphocholine (DPhPC), 1,2-distearoyl-sn-glycero-3-phosphocholine (DSPC) 1,2-dipalmitoyl-sn-glycero-3-phosphocholine (DPPC), or 1,2-dipalmitoyl-sn-glycero-3-[phospho-rac-(1-glycerol)] (DPPG) can be employed as the amphiphilic molecules in the droplet encapsulates of the invention, or a mixture of one or more thereof. The glycerophospholipid 1,2-dioleoyl-sn-glycero-3-phosphoethanolamine (DOPE) may also be used, and is typically used in combination with a pH-sensitive lipid, for instance a fatty acid (see further below). DPhPC is preferred.

The amphipathic molecules in the compartments of the compartmentalised and multi-compartmentalised gel matrix of the invention may comprise one or more fatty acids, e.g. oleic acid. Fatty acids are of course well known to the skilled person and a wide range of these are commercially available. The amphipathic molecules may for instance comprise a mixture comprising: (a) one or more phospholipids, and (b) one or more fatty acids.

Inner and Outer Layer of Amphipathic Molecules

As mentioned in the section above, amphipathic molecules are distributed in an inner layer of amphipathic molecules (at the interface between an aqueous droplet and a surrounding volume of hydrophobic medium) and an outer layer of amphipathic molecules (around a volume of hydrophobic medium). The outer layer may be at an interface between a volume of hydrophobic medium and an aqueous layer, or between a volume of hydrophobic medium and a gel matrix.

The inner layer of amphipathic molecules may be referred to herein as the "inner layer" and the outer layer of amphipathic molecules may be referred to as the "outer layer".

The inner layer of amphipathic molecules formed around the aqueous droplet usually comprises a monolayer of amphipathic molecules which is formed and maintained naturally by the interaction of the hydrophobic and hydrophilic groups with the aqueous medium so that the molecules align on the surface of the droplet with the hydrophilic groups facing inwards towards the aqueous medium and the hydrophobic groups facing outwards towards the hydrophobic medium.

Likewise, the outer layer of amphipathic molecules formed around the volume of hydrophobic medium usually comprises a monolayer of amphipathic molecules which is formed and maintained naturally by the interaction of the hydrophobic and hydrophilic groups with: (a) the hydrophobic medium and (b) the surrounding aqueous layer or gel matrix. Both the inner layer and outer layer of amphipathic molecules are usually therefore monolayers of amphipathic molecules.

The inner and outer layers of amphipathic molecules may not form immediately. For instance, upon insertion of a volume of hydrophobic medium comprising amphipathic molecules into a gel precursor to form a compartment, the compartment may not initially comprise an outer layer of amphipathic molecules. For example, the amphipathic molecules may be distributed evenly throughout the volume of hydrophobic medium. Upon formation of an interface, for instance with the gel precursor or gel matrix, amphipathic molecules within the volume of hydrophobic medium may self-assemble such that a monolayer is formed at its surface. Similarly, upon insertion of an aqueous droplet into a volume of hydrophobic medium, an inner layer of amphipathic molecules may not immediately exist.

Upon formation of the interface between the volume of hydrophobic medium and the aqueous droplet, amphipathic molecules which are present within the hydrophobic medium and/or the aqueous medium may self-assemble to form a monolayer at the surface of the aqueous droplet. Usually, the amphipathic molecules within a compartment are present within the hydrophobic medium. For example, the hydrophobic medium may comprise amphipathic molecules. For instance, the hydrophobic medium may comprise amphipathic molecules and the aqueous medium may not comprise amphipathic molecules.

Bilayer of Amphipathic Molecules

In some embodiments of the compartmentalised gel matrix and multi-compartmentalised gel matrix of the invention, particularly when an aqueous droplet is first synthesised within a volume of hydrophobic medium and the aqueous droplet has not yet had time to adhere to the outer layer of amphipathic molecules to form a thermodynamically more stable structure, the aqueous droplet will be located fully within the volume of hydrophobic medium. The inner layer of amphipathic molecules will not in such cases be in contact with the outer layer of the compartment; the inner layer will usually only be in contact with the hydrophobic medium.

In one embodiment, therefore, the aqueous droplet is situated inside the volume of hydrophobic medium and said inner layer of amphipathic molecules is not in contact with the outer layer. Generally, in this embodiment, the inner layer of amphipathic molecules contacts the hydrophobic medium.

Typically, however, a compartment according to the invention comprises at least one bilayer of amphipathic molecules. Usually, for instance, the outer layer of amphipathic molecules around the volume of hydrophobic medium and the inner layer of amphipathic molecules around the aqueous droplet are capable of together forming a bilayer of amphipathic molecules at an interface between the aqueous droplet and the outer layer of amphipathic molecules.

Thus, in some embodiments, the aqueous droplet is situated at the edge of the volume of hydrophobic medium, wherein a part of the inner layer around the aqueous droplet contacts a part of the outer layer of amphipathic molecules around the volume of hydrophobic medium, and the said parts that are in contact thereby form a bilayer of said amphipathic molecules at an interface between the aqueous droplet and the outer layer. Typically in such embodiments, a different part of the inner layer around the said aqueous droplet contacts the hydrophobic medium. Such arrangements are kinetically stable. Formation of a bilayer typically lowers the energy of the system.

In some embodiments, in a multi-compartmentalised gel matrix according to the invention a part of the outer layer of amphipathic molecules contacts a part of the inner layer of amphipathic molecules in at least one of the compartments. Preferably, the said parts of the outer layer of amphipathic molecules and the inner layer of amphipathic molecules that are in contact form a bilayer.

Accordingly, in a preferred embodiment, the invention provides a multi-compartmentalised gel matrix comprising a gel matrix and a plurality of compartments, wherein each compartment comprises: a volume of a hydrophobic medium; an outer layer of amphipathic molecules around the volume of hydrophobic medium at an interface between the volume of hydrophobic medium and the gel matrix; an aqueous droplet in the volume of hydrophobic medium; and an inner layer of amphipathic molecules at an interface between the aqueous droplet and the hydrophobic medium, wherein a part of the outer layer of amphipathic molecules contacts a part of the inner layer of amphipathic molecules forming a bilayer, and wherein said bilayer comprises a membrane protein.

A compartment according to the invention may comprise a bilayer comprising two inner layers of amphipathic molecules. Such a bilayer may be present in a compartment as well as, or instead of, a bilayer comprising an outer layer of amphipathic molecules (that is, a layer of amphipathic molecules around the outer edge of a volume of hydrophobic medium). Typically, where a compartment comprises a plurality of aqueous droplets, part of an inner layer of amphipathic molecules around one aqueous droplet in the compartment may contact a part of an inner layer of amphipathic molecules around a further aqueous droplet in the same compartment, thereby forming a bilayer of the amphipathic molecules at an interface between said first and second aqueous droplets.

Thus, more generally, a compartment according to the invention typically comprises a bilayer of amphipathic molecules, which bilayer is formed at an interface between the aqueous droplet and the outer layer of amphipathic molecules around a volume of hydrophobic medium, or between the aqueous droplet and a second aqueous droplet.

The bilayer at the interface between said first and second droplets may further comprise one or more membrane proteins. Droplets within a compartment can exchange chemical species with each other through membrane proteins incorporated in the bilayer between the droplets. The membrane protein may be of any type, including for instance a pump, channel and/or pore.

Usually, at least one of said first and second droplets is situated at the edge of the volume of hydrophobic medium, wherein part of the inner layer of amphipathic molecules around the aqueous droplet contacts the outer layer of amphipathic molecules around the volume of hydrophobic medium, thereby forming a bilayer of said amphipathic molecules at an interface between the aqueous droplet and the outer layer of amphipathic molecules.

A bilayer as described herein is typically a lipid bilayer. Accordingly, the invention provides a compartmentalised or multi-compartmentalised gel matrix comprising a bilayer as described above wherein the bilayer is a lipid bilayer.

The bilayer at the interface between said aqueous droplet and the outer layer may further comprise one or more membrane proteins. The membrane protein may be of any type, including for instance a pump, channel and/or pore. Accordingly, the invention provides a compartmentalised or multi-compartmentalised gel matrix comprising a bilayer wherein the bilayer comprises a membrane protein.

Proteins within a Bilayer

A bilayer according to the invention (or, indeed, any of the more generically-defined inner or outer layers of amphipathic molecules described herein) may further comprise a membrane protein. A membrane protein may be present in a bilayer comprising a part of an inner layer of amphipathic molecules and an outer layer of amphipathic molecules, and/or in a bilayer comprising two inner layers of amphipathic molecules.

A membrane protein may typically be included in the bilayer to enable or assist the transport of a species across the bilayer. For instance, a membrane protein may form an ion channel or a protein pore. An ion channel or a protein pore may comprise a single membrane protein or may be constructed from one or more membrane proteins, wherein the said membrane proteins are the same or different.

The membrane protein may be of any type. The use of integral membrane proteins has been demonstrated, but it is equally expected that peripheral membrane proteins could be used. The membrane protein may for instance be a membrane pump, channel and/or pore, to allow for precise control over the exchange of material, and electrical communication, between the droplet and the external solution. Further possible membrane proteins include, but are not limited to, a receptor, a transporter or a protein which effects cell recognition or a cell-to-cell interaction. The membrane protein could for instance be a membrane pore, for example α hemolysin (abbreviated to αHL). In another example, the membrane protein could be a DNA nanopore. However, any suitable membrane protein can be used including the two major classes, that is, β-barrels or α-helical bundles. An important application is a membrane protein which is a pore or a channel. Besides a protein pore or channel, further possible membrane proteins include, but not exclusively, a receptor, a transporter or a protein which effects cell recognition or a cell-to-cell interaction. A bilayer comprising a part of an inner layer of amphipathic molecules and an outer layer of amphipathic molecules, and/or a bilayer comprising two inner layers of amphipathic molecules, may comprise more than one membrane protein. For instance, a particular bilayer may contain multiple copies of the same membrane protein, or two or more different classes of membrane proteins. Where more than one class is present, the bilayer may contain multiple copies of each different class. The bilayer may for example comprise different kinds of ion channel membrane proteins, for instance at least one sodium channel protein and at least one potassium channel protein.

Suitable membrane proteins which allow for exchange of materials and electrical communication are known and readily available to the skilled person; many such proteins are either commercially available or can be prepared by known methods. For instance, WT αHL monomers can be prepared by in vitro transcription-translation (IVTT), and heptamerised by incubation with rabbit red blood cell membranes. The heptamers are typically purified by sodium dodecyl sulphate polyacrylamide gel electrophoresis (SDS-PAGE) (Maglia, G. et al. Method. Enzymol. 475, 591-623, 2010). Also, Bayley, H. et al. Droplet interface bilayers. *Mol. BioSyst.* 4, 1191-1208 (2008) lists several proteins that were tested for insertion into droplet interface bilayers made in bulk oil. Another example of a membrane protein which allows exchange of materials and electrical communication across a bilayer is cytolysin A (abbreviated to ClyA). The preparation of ClyA and its insertion into a bilayer of the invention is described in the Examples section.

Accordingly, in some embodiments a compartmentalised or multi-compartmentalised gel matrix according to the invention comprises a bilayer and said bilayer comprises a protein pore. In one embodiment, a compartmentalised or multi-compartmentalised gel matrix according to the invention comprises a bilayer and the said bilayer comprises cytolysin A. In another embodiment, a compartmentalised or multi-compartmentalised gel matrix according to the invention comprises a bilayer and the said bilayer comprises alpha-hemolysin.

Double Bilayer of Amphipathic Molecules

A multi-compartmentalised gel matrix is useful in the creation of a double bilayer. Double bilayers are particularly useful in mimicking biological objects comprising double bilayers, such as mitochondria or cell nuclei.

The term "double bilayer" as used herein denotes a pair of bilayers arranged next to one another. By "next to" is meant that the bilayers are sufficiently close that they are in communication one another. Thus, the invention provides a multi-compartmentalised gel matrix as described herein comprising two bilayers as defined above which are positioned next to one another and form a double bilayer.

In one embodiment, molecules may be exchanged across both bilayers in a double bilayer. For example, molecules that are transported out of a compartment across one bilayer (for example via a protein pore) are typically transported into the second compartment across the other bilayer of the double bilayer (for example via a protein pore). In another example, the two compartments either side of a double bilayer are in electrical contact with one another, for example by an ion flow across the double bilayer.

For instance, two bilayers which together form a double bilayer may be separated by a distance less than 200 μm, e.g. less than 100 μm, preferably less than 10 μm. In some embodiments, the distance that separates the bilayers which together form a double bilayer may be 500 nm or less, or 200 nm or less.

For example, in one embodiment the two bilayers forming a double bilayer are separated by a distance of 1 nm to 200 μm. In another embodiment the two bilayers forming a double bilayer are separated by a distance of 50 nm to 50 μm. In some embodiments, the two bilayers which together form the double bilayer are in contact.

In some embodiments, the pair of bilayers in a double bilayer are separated by a region of the gel matrix. In some embodiments, the region of the gel matrix that separates the bilayers is 10 nm thick or less.

The two bilayers forming a double bilayer are typically separated by a gel strip. By "gel strip" is meant a portion of gel within the gel matrix that is situated between two bilayers which together form a double bilayer. In some embodiments, the gel strip has a maximum thickness of less than 200 nm, e.g. less than 100 nm, preferably less than 50 nm. In some embodiments, the gel strip has a minimum thickness of at least 0.1 nm. For example, the gel strip may have a thickness of from 0.1 to 50 nm, or 0.1 to 20 nm.

The gel strip typically comprises only one gel region. However, where the two bilayers which together form the double bilayer are situated in different gel regions of the gel matrix, the gel strip may comprise two gel compositions, corresponding to the gel compositions of the two different gel regions in which the two bilayers are situated.

In some embodiments, one or both of the bilayers which together form the double bilayer are present in nested compartments. In these embodiments, the bilayers forming the double bilayer may be separated not only by a gel strip but also by a portion of one or more aqueous layers of each nested compartment. Preferably, though, the bilayers in a double bilayer are separated only by a gel strip.

In some embodiments, both of the bilayers which together form the double bilayer are present in the same nested compartment. That is, the invention provides a compartmentalised or multi-compartmentalised gel matrix comprising a nested compartment, wherein the nested compartment comprises a double bilayer, wherein one bilayer within the double bilayer comprises a bilayer of amphipathic molecules at an interface between the aqueous layer in the nested compartment and the surrounding gel, and the second bilayer within the double bilayer comprises:
  (a) a layer of amphipathic molecules at an interface between an aqueous droplet and a volume of hydrophobic medium in said nested compartment; and
  (b) a layer of amphipathic molecules at an interface between the aqueous layer and the volume of hydrophobic medium in said nested compartment.

In this embodiment, it is preferred that the gel is a hydrogel.

The two bilayers which together form a double bilayer are each as described in the "bilayers" section above. Briefly, the bilayers each comprise two monolayers. The monolayers comprise amphipathic molecules, which are also as described above. Typically, each of the two bilayers within the double bilayer comprises (a) an inner layer of amphipathic molecules at an interface between an aqueous droplet and the volume of hydrophobic medium in a compartment; and (b) an outer layer of amphipathic molecules surrounding the said volume of hydrophobic medium. In some embodiments, the said outer layer of amphipathic molecules (b) is at an interface between the said volume of hydrophobic medium and an aqueous layer in the said compartment. However, in a preferred embodiment, each of the two bilayers within the double bilayer comprises (a) an inner layer of amphipathic molecules at an interface between an aqueous droplet and the volume of hydrophobic medium in a compartment; and (b) an outer layer of amphipathic molecules at an interface between the said hydrophobic medium and the said gel matrix.

Thus, the invention provides a multi-compartmentalised gel matrix comprising a double bilayer wherein each bilayer within the double bilayer comprises:
  (a) a layer of amphipathic molecules at an interface between an aqueous droplet and the volume of hydrophobic medium in a compartment; and
  (b) a layer of amphipathic molecules at an interface between an aqueous droplet and the volume of hydrophobic medium.

The invention further provides a multi-compartmentalised gel matrix comprising a double bilayer wherein one bilayer within the double bilayer comprises:
  (a) a layer of amphipathic molecules at an interface between an aqueous droplet and a volume of hydrophobic medium; and
  (b) a layer of amphipathic molecules at an interface between the gel matrix and the volume of hydrophobic medium.

and the second bilayer within the double bilayer comprises:
  (a) a layer of amphipathic molecules at an interface between an aqueous droplet and a volume of hydrophobic medium; and
  (b) a layer of amphipathic molecules at an interface between the aqueous layer and the volume of hydrophobic medium.

The length of the double bilayer is not particularly limited. However, it is influenced by the size of the volumes of hydrophobic medium whose outer layers of amphipathic molecules both contribute to the bilayers which together form the double bilayer. Accordingly, the length of the double bilayer may increased by pushing the said volumes of hydrophobic medium together, and may be decreased by pulling said volumes of hydrophobic medium apart.

As mentioned above, one or both of the two bilayers in a bilayer may comprise membrane proteins. Alternatively or additionally, a double bilayer may comprise a membrane protein that spans the double bilayer (that is, the said membrane protein spans both bilayers within the double bilayer). Examples of such membrane proteins are membranes that form pores spanning two bilayers, such as gap junctions and nuclear pores.

As described above in relation to membrane proteins spanning single bilayers, a protein pore spanning a double bilayer may consist of a single protein or may be constructed from multiple proteins. The membrane proteins may be provided in the compartment for self-assembly. For example, one or more membrane proteins may be provided in an aqueous droplet in one or both compartments that contribute to the double bilayer. Alternatively or additionally, a membrane protein (e.g. a protein pore) may be inserted into a double bilayer after its formation.

The presence of a membrane protein spanning a double bilayer may be detected by techniques known in the art. For example, the electrical contact between adjacent compartments may be measured. An increase in current suggests the insertion of a transport mechanism (such as a protein pore) between the compartments. This is discussed in more detail in Example 5.

The multi-compartmentalised gel matrix of the invention may therefore be used to study the properties of double bilayers. Techniques for such study are well-known in the art.

Thus, in some embodiments at least one compartment of the compartmentalised or multi-compartmentalised gel matrix comprises an electrode. For example, where a multi-compartmentalised gel matrix comprises a double bilayer, at least one of the compartments contributing to the double bilayer comprises an electrode, e.g. an electrode suitable for measuring the electrical properties of the double bilayer. In another embodiment, where a compartment within a compartmentalised gel matrix comprises a bilayer, the said compartment may comprise an electrode suitable for measuring the electrical properties of the bilayer. In the foregoing examples, the gel of the compartmentalised or multi-compartmentalised gel matrix may comprise a further electrode.

In another embodiment, where a multi-compartmentalised gel matrix comprises two compartments in electrical communication with each other, each of said compartments comprises an electrode.

The electrode is typically an electrochemically reversible electrode. Usually the electrode comprises an electrochemically active electrode such as an Ag/AgCl electrode. Alternatively, the electrode may be a high work function metal (for instance gold, silver, nickel, palladium or platinum), if used in conjunction with an electrochemically active mediator such as ferrocyanide. For instance, a redox couple, or a member of a redox couple which may be partially oxidised or reduced to provide the redox couple, may be used.

Suitable redox couples include those known in the art such as $Fe^{2+}/Fe^{3+}$, ferrocene/ferrocium or $Ru^{2+}/Ru^{3+}$.

The ability to move material from one compartment to another across a double bilayer in a multi-compartmentalised gel matrix may have particular uses in transporting material between different environments. For example, material may be transported across a double bilayer from one gel region to another gel region of the multi-compartmentalised gel matrix Also envisaged as part of the present invention is a network of double bilayers. For example, a chain of a first, second and third compartment in a multi-compartmentalised gel matrix according to the invention may comprise two double bilayers: between the first and second compartments, and between the second and third compartments.

More complex systems are, of course, possible. However, using this example it is possible to see how a complex system may be built up. Transport of a material into a first aqueous droplet in a first compartment may be controlled by a membrane protein. The inner layer of amphipathic molecules around this first aqueous droplet may contribute to a first double bilayer, in which case material in the first compartment may be transported into a second compartment by a membrane protein spanning the first double bilayer. Alternatively, the material may need to be transported between one or more aqueous droplets in the first compartment to reach an aqueous droplet which forms part of the first double bilayer. When transported across the first double bilayer, the material will arrive in an aqueous droplet in the second compartment. As in the first compartment, this aqueous droplet may be connected to the second double bilayer and may transfer the material directly into the third compartment. Alternatively, the material may have to pass through a series of one or more aqueous droplets in the second compartment to reach the aqueous droplet which forms the second bilayer. Once in said droplet, the material will be transferred into an aqueous droplet in the third compartment.

Each transfer across a bilayer may be controlled by one or more membrane proteins. These membrane proteins may be chosen to allow transfer of material only under certain conditions, for instance below a particular pH (e.g. below pH 7.5), or at a particular ionic concentration. Thus the transfer of material from one compartment to another may be contingent on various environmental factors, allowing the precise control of the movement of material through the compartments of the multi-compartmentalised gel matrix of the invention.

The compartmentalised and multi-compartmentalised gel matrices of the invention have uses in sensing and signalling. By using membrane proteins and multiple compartments linked by bilayers, compartmentalised and multi-compartmentalised gel matrices can sense their environment, process information, and contingently deliver materials to the surroundings. Accordingly, the invention further provides the use of a compartmentalised or multi-compartmentalised gel matrix of the invention as defined herein for trafficking a molecule between compartments therein and/or for delivering a molecule from a therein to the external environment. More generally, the invention further provides the use of a compartmentalised or multi-compartmentalised gel matrix of the invention as defined herein for exchanging materials between a compartment or compartments therein and the environment.

Networks of aqueous droplets joined by droplet interface bilayers can be constructed that exploit a variety of membrane pumps, channels and pores to act as light sensors, batteries, and electrical devices. This is described in Holden, M. A. et al., J. Am. Chem. Soc. 129, 8650-8655 (2007), and Maglia, G. et al. Nat. Nanotechnol. 4, 437-440 (2009), which relate to the construction of such droplet networks in a bulk oil phase. Such networks of aqueous droplets can also be constructed within one or more compartments of a gel matrix of the invention, using the methods described herein, to provide compartmentalised or multi-compartmentalised gel matrices of the invention that function as sensors, batteries, or electrical devices.

Accordingly, the invention further provides the use of a compartmentalised or multi-compartmentalised gel matrix of the invention as defined herein as a sensor, battery, or electrical device. Further provided is a sensor, a battery, or an electrical device, comprising a compartmentalised or multi-compartmentalised gel matrix of the invention as defined herein.

Network

The multi-compartmentalised gel matrix of the invention may comprise a network. By "network" is meant a network of compartments. Thus, the invention provides a multi-compartmentalised gel matrix wherein the compartments form a network. The compartments in a network are usually in communication with one another: each compartment may be in communication with one or more other compartments. The network of compartments may typically comprise two or more compartments which are in communication with each other. By "in communication with each other" is meant that the said two or more compartments may interact. For instance, two or more compartments within the network may be in electrical contact or may be capable of exchanging material with one another. Material may be communicated, or exchanged, between compartments for example by diffusion or by protein transport. Communication may occur between two or more compartments within a network through a bilayer in each compartment, and optionally through protein pores when protein pores are present in the bilayers.

As explained above, transport of a material may occur within an individual compartment as aqueous droplets within a compartment can exchange material between each other, typically via membrane proteins in the bilayers between droplets. Additionally, aqueous droplets within a compartment can exchange material between the droplet and the surrounding gel matrix (optionally via the surrounding aqueous layer if the compartment is a nested compartment). This transport is usually effected via membrane proteins in a bilayer formed between an inner layer of amphipathic molecules around an aqueous droplet and an outer layer of aqueous molecules around a volume of hydrophobic medium. Thus, compartments having multiple aqueous droplets therein are capable of trafficking materials such as chemical compounds from aqueous droplet to aqueous droplet, as well as to and from the gel matrix.

Additionally, a multi-compartmentalised gel matrix comprising compartments situated next to one another may traffic material from one compartment to another within the matrix. By "next to" is meant that the compartments are sufficiently close together that they may be in communication with one another. For instance, they may be in electrical contact with one another. In another instance, the distance may be sufficiently small that a material in one compartment (e.g. a small molecule) may diffuse from one compartment into the other. A simple embodiment is described below.

In this exemplary embodiment, a network consists of two compartments, each containing a volume of hydrophobic medium with an aqueous droplet therein. In each compartment, a bilayer is formed comprising a part of the inner layer of amphipathic molecules around the aqueous droplet in contact with a part of the outer layer of amphipathic molecules around the volume of hydrophobic medium. Each bilayer comprises an ion channel. The compartments are next to one another and in particular the bilayers are next to one another. In this embodiment, an ionic species in one of the aqueous droplets may diffuse out of that aqueous droplets through a bilayer via an ion channel, through a small region of gel and into the second aqueous droplet through the second bilayer via the second ion channel.

A network of compartments in the multi-compartmentalised gel matrix may be one-dimensional, two-dimensional or three-dimensional. Thus, the invention provides a multi-compartmentalised gel matrix comprising a network of compartments wherein the network is a two- or three-dimensional network. A one-dimensional network may comprise a "chain" of compartments, wherein each compartment is next to a maximum of two other compartments to form a line of compartments. A two- or three-dimensional network is a multi-compartmentalised gel matrix in which at least one compartments is in contact with more than two other compartments. Usually, in a network, more than one compartment in the network is in contact with more than two other compartments. In some networks, each and every compartment in the network is in contact with more than two other compartments. The network can for instance be a "two-dimensional" monolayer of compartments or a "three-dimensional" mass of compartments. Complex transport systems can be built up in this way.

The communication between the compartments making up the network may be controlled in a variety of ways. For instance, communication into and out of each compartment can be controlled by the number and type of membrane proteins present in any bilayers comprising the outer layer of amphipathic molecules in the compartment. Communication between each compartment may further be influenced by the distance between compartments within the gel matrix. Communication may also be influenced by the type of gel within the gel matrix; for instance, a hydrophilic gel (e.g. a hydrogel) may allow water-soluble small molecules to diffuse between compartments but will resist the passage of lipophilic molecules. Thus, where a gel matrix comprises multiple gel regions, some regions of gel may allow the communication of certain species between compartments whereas other regions of the gel matrix, which have a different composition, may not allow the communication of those species.

Thus, multi-compartmentalised gel matrices can be prepared that are capable of sensing their environment, processing the information, and then contingently delivering materials to, or receiving materials from, the environment.

The number of compartments within a network is not particularly limited. It can in principle be very high, for instance in the order of thousands. However, more typically it will be of the order of tens or hundreds of compartments, for example from 2 to 200 compartments, e.g. 2 to 100 or 2 to 50 compartments. Additionally, as discussed above, each compartment may comprise a plurality of aqueous droplets, for instance up to fifty droplets, meaning that a complex system can be created with a small number of compartments (e.g. less than ten compartments).

Uses of the Compartmentalised Gel Matrix

Compartmentalised and multi-compartmentalised gel matrices of the invention may be used as drug delivery vehicles, for instance as vehicles for delivering an active agent (e.g. therapeutic agents, diagnostic agents, or contrast agents) in vivo, or for delivering any other type of compound or composition in vivo as desired.

A particular advantage of the compartmentalised and multi-compartmentalised gel matrix of the invention is that they are robust. They may therefore be subject to the rigours of storage and transport without significant degradation, for example by breakage or leakage of active agent. Moreover, the gel matrix may comprise one or more gel regions. These gel regions may have properties suited to the particular mode of delivery. For instance, they may comprise water-resistant outer layer for the purpose of storage and transport, and one or more inner hydrophilic regions to aid rapid efflux of a hydrophilic active agent therein. Furthermore, each compartment may comprise a different environment, for instance a different solvent, suited for carrying a different active agent.

A further particular advantage of the multi-compartmentalised gel matrix of the invention is that they may comprise a double bilayer.

In one embodiment, the compartmentalised gel matrix or multi-compartmentalised gel matrix of the invention further comprises an active agent.

In one embodiment, the compartmentalised gel matrix or multi-compartmentalised gel matrix of the invention further comprises a therapeutic agent. The therapeutic agent may be in prodrug form. Thus in one embodiment, the compartmentalised gel matrix or multi-compartmentalised gel matrix of the invention further comprises a prodrug.

In one embodiment, the compartmentalised gel matrix or multi-compartmentalised gel matrix of the invention further comprises a nutraceutical. By "nutraceutical" is meant a dietary supplement. Typical examples of dietary supplements are food extracts including, for example, vitamins, minerals, plant extracts, amino acids, enzymes and so on.

The compartmentalised gel matrix or multi-compartmentalised gel matrix of the invention may alternatively comprise a diagnostic agent, or for instance a contrast agent.

The therapeutic agent, nutraceutical, prodrug, diagnostic agent, or contrast agent may be present in an aqueous droplet within one or more compartments according the invention. Alternatively, it may be present in the hydrophobic medium. Typically, it is present in the or an aqueous droplet in one or more compartments.

Multiple compartments within a multi-compartmentalised gel matrix can release their contents into the environment simultaneously or at different times, e.g. upon exposure to an external stimulus such as a change in pH or temperature; this provides a useful method for the combinatorial delivery of drugs. Indeed, delivering multiple pharmacological species to a cell by encapsulation in conventional liposomes requires that these species be encapsulated either together, allowing potentially undesirable reactions between them; or separately, in which case each cell will receive a poorly controlled proportion of each species. By contrast, the delivery of several drugs encapsulated in different compartments of a single gel matrix would allow precise control over dosage proportions. One or more active ingredients may be present in the hydrophobic medium, and one or more different active ingredients may be present in the aqueous medium (e.g. in the aqueous droplets within the or each compartment). This may be beneficial for the delivery of drugs with independent mechanisms of action; their uptake by cells in fixed proportions could be expected to increase their overall efficacy, and decrease the probability of resistance developing to any one of the drugs.

Accordingly, in one embodiment, the compartmentalised or multi-compartmentalised gel matrix of the invention further comprises a first active agent and a second active agent. Typically, these are present in different compartments, but may be present within different areas of the same compartment (e.g. in different aqueous droplets within a compartment, or within the hydrophobic and aqueous medium within the droplet).

Thus, in one embodiment the first active agent is within the, or at least one of the, aqueous droplets in one or more compartments, and the second active agent is within the volume of hydrophobic medium in one or more compartments.

In another embodiment, one or more compartments in the compartmentalised gel matrix or multi-compartmentalised gel matrix of the invention comprises a plurality of aqueous droplets, and the first active agent and the second active agent are within different aqueous droplets within a single compartment.

In another embodiment, the first active agent is present in one or more compartments within a first gel region of a multi-compartmentalised gel matrix, and the second active agent is present in one or more compartments within a second gel region of a multi-compartmentalised gel matrix.

In a further embodiment, the compartmentalised or multi-compartmentalised gel matrix of the invention comprises a first active agent in a first solvent environment and a second active agent in a second solvent environment. Typically, where the gel matrix of the invention comprises a hydrophilic active agent, said hydrophilic active agent is present within an aqueous environment (e.g. in an aqueous droplet or aqueous layer, or other volume of polar medium). Typically, where the gel matrix of the invention comprises a hydrophobic active agent, said hydrophobic active agent is present within a hydrophobic environment (e.g. in a volume of hydrophobic medium).

Thus, in some embodiments the invention provides a compartmentalised or multi-compartmentalised el matrix comprising a hydrophilic active agent in an aqueous droplet and a hydrophobic active agent in a volume of hydrophobic medium, wherein the aqueous droplet and volume of hydrophobic medium are present in the compartment or compartments of the said gel matrix. Where the gel matrix is a multi-compartmentalised gel matrix, the hydrophilic active agent and the hydrophobic active agent may be present in the same or different compartments.

In some embodiments, the invention provides a compartmentalised or multi-compartmentalised gel matrix comprising in one or more compartments a first carrier solvent comprising a first active agent, and a second carrier solvent comprising a second active agent. The first and second carrier solvents may be the same or different; generally, the first and second carrier solvents differ when the first and second active agents differ. In some embodiments, the carrier solvents are present in the same compartment. Carrier solvents are typically present in the same compartment where one carrier solvent is present in the volume of hydrophobic medium and the other is present in an aqueous droplet. Carrier solvents may also be present in the same compartment when said carrier solvents are present in two different aqueous droplets in a compartment. Where the carrier solvents are present in different compartments of a multi-compartmentalised gel matrix, the type of carrier solvent is not particularly limited.

Typically, the first and second active agents are selected from therapeutic agents, nutraceuticals, diagnostic agents, drugs for use together in combination therapies, prodrugs and their corresponding activators, drugs and their corresponding deactivator compounds, and contrast agents for monitoring the biodistribution of a drug.

Alternatively, the first and second active agents may be reactant compounds for reacting together in a chemical reaction.

Typically, the first and second active agents are present in the compartmentalised gel matrix or multi-compartmentalised gel matrix in a predetermined proportion, for instance in a predetermined dosage proportion, or for instance in a stoichiometric proportion suitable for a particular chemical reaction to take place between the active agents.

The delivery of multiple drugs with independent mechanisms of action can be more effective than the sum of the effects of each drug separately. A common use of drug combinations is to prevent the emergence of drug resistance in a wide range of diseases. If the various drugs are delivered in solution, the proportion of each drug taken up by a particular cell is poorly controlled. By contrast, encapsulation of these drugs in a single carrier, such as a compartmentalised or multi-compartmentalised gel matrix of the invention, enables precise control over dosage proportions. Encapsulating multiple drugs in separate compartments prevents any undesirable interactions between the drugs, and allows the conditions in each compartment to be optimized for the drug in that compartment. Furthermore, encapsulating multiple drugs in different gel regions of the gel matrix may allow the conditions under which the drug is released to be controlled by controlling the properties of the gel regions.

Thus, in one embodiment, the first and second active agents referred to above are two different drugs. Typically, the first and second active agents are drugs which are suitable for use together in a combination therapy. The drugs may be present in the compartmentalised or multi-compartmentalised gel matrix in a predetermined dosage proportion. Many drug combinations which are suitable for use together in a combination therapy, and which are therefore suitable for use together in a compartmentalised or multi-compartmentalised gel matrix of the invention, are known in the art.

For instance, the use of combinations of antimalarials that do not share the same resistance mechanism may reduce the chances of drug resistance (White, N. "Antimalarial drug resistance and combination chemotherapy." *Phil. Trans. R. Soc. Lond B* 354, 739-749 (1999)). Thus, the first and second active agents may be two different antimalarial drugs having different drug resistance mechanisms. In particular, the first and second antimalarial drugs may be pyrimethamine in combination with sulphadoxine or sulphalene, which combination is used to treat malaria caused by chloroquine-resistant *P. falciparum*. The two compounds inhibit sequential steps in folate biosynthesis. The same mechanism is employed by the combination of chlorproguanil and dapsone. Other antimalarial drug combinations with different mechanisms of action include: atovaquone and proguanil, artemisin and mefloquine, artemether and lumefantrine, artesunate with atovaquone and proguanil, quinine and tetracycline, and quinine and clindamycin. Thus, the first and second active agents may be any of the abovementioned combinations.

A further example is cancer, for which a great number of combination chemotherapy regimens exist (see, for instance, http://www.macmillan.org.uk). Some examples are ABVD (doxorubicin, bleomycin, vinblastine and dacarbazine) for Hodgkin's lymphoma, CHOP (cyclophosphamide, doxorubicin, vincristine and prednisone) for non-Hodgkin's lymphoma, and CMF (cyclophosphamide, methotrexate and 5-fluorouracil) for breast cancer. Thus, the compartmentalised or multi-compartmentalised gel matrix of the invention may comprise any of the abovementioned combinations and the different drugs may be contained within the same or different compartments of the compartmentalised or multi-compartmentalised gel matrix. The different drugs may further be contained within different gel regions of the gel matrix.

Yet further examples of drugs which can be included within the compartmentalised or multi-compartmentalised gel matrix of the invention are drug combinations used to treat viral infection (see Clavel, F. & Hance, A. J. HIV drug resistance. N. Engl. J. Med. 350, 1023-1035 (2004)). Typical combinations include nucleoside reverse-transcriptase inhibitors (which inhibit reverse transcription of the viral genome) and a non-nucleoside reverse-transcriptase inhibitor (which inhibits reverse transcription of the viral genome by a different mechanism) or a protease inhibitor (which inhibits viral particle assembly). Some current recommended regimens are (see http://aidsinfo.nih.gov): emtricitabine, tenofovir and efavirenz; emtricitabine, tenofovir, tazanavir and ritonavir; emtricitabine, tenofovir, darunavir and ritonavir; and emtricitabine, tenofovir, and raltegravir. The compartmentalised or multi-compartmentalised gel matrix of the invention may therefore comprise any of the abovementioned combinations and the different drugs may be contained within different compartments. The said different drugs may further be contained within different gel regions of the gel matrix.

The compartmentalised and multi-compartmentalised gel matrices of the invention also allow the delivery of compounds that independently have little or no effect, and are only effective in combination with other compounds. Thus, the term "active agent" should be taken to include agents which individually have little effect. These synergistic combinations are used in some treatments for bacterial infection, and in the delivery of prodrugs (inactive precursors of active drugs). In some cases, as in the treatment of bacterial infections discussed below, the various compounds may be contained together in the same gel matrix, in which case the advantages of compartmentalised and multi-compartmentalised gel matrices are as discussed above. In other cases, such as the delivery and activation of prodrugs as discussed below, the components react when brought together. Thus, when a compartmentalised or multi-compartmentalised gel matrix is triggered to release its contents, an active species can be created in situ with different properties to its parent compounds. Some examples are as follows:

Bacterial infection [Walsh, C. Molecular mechanisms that confer antibacterial drug resistance. Nature 406, 775-781 (2000)]: Amoxicillin is used in combination with clavulanate, which inactivates an enzyme that in certain strains would otherwise deactivate amoxicillin. The combination of ampicillin and sulbactam employs a similar principle, where sulbactam is the enzyme deactivator. Another synergistic combination is that of quinupristin and dalfopristin.

Accordingly, the first and second drugs in the compartmentalised or multi-compartmentalised gel matrix of the invention may for instance be amoxicillin and clavulanate respectively, ampicillin and sulbactam respectively, or quinupristin and dalfopristin respectively.

Another possibility is enzyme-prodrug therapy [Xu, G. & McLeod, H. L. Clin. Cancer Res. 7, 3314-3324 (2001)]: HMR 1826, an inactive derivative of the anti-cancer drug doxorubicin, is converted by human beta-glucuronidase to doxorubicin. In a study that employed this combination, the human beta-glucuronidase gene was first transfected into tumour cells, which then produced the enzyme and secreted it. The prodrug HMR 1826 was added to the extracellular space, where it was converted to the active drug doxorubicin. Whereas HMR 1826 is not permeable to the cell membrane, doxorubicin is able to access the cytosol. Accordingly, the first and second agents in the compartmentalised or multi-compartmentalised gel matrix of the invention may be HMR 1826 and human beta-glucuronidase.

In another embodiment, the compartmentalised or multi-compartmentalised gel matrix of the invention is used as a vehicle for the simultaneous delivery of a prodrug and its activator. In this application, one aqueous droplet inside a compartment contains a prodrug, and another aqueous droplet of the same compartment contains its corresponding activator. Jointly releasing the contents upon some external stimulus would allow the prodrug and activator to combine, producing the active species in situ. This would allow the administration of drugs that are, for example, too unstable or insoluble to be delivered in the active state. This approach could also be used to encapsulate a prodrug impermeant to a bilayer at the surface of the said aqueous droplets, which is converted to an active drug that is permeant to cell membranes.

Thus, in one embodiment, the first active agent is an inactive form of a drug which is capable of being activated by an activator, and the second active agent is said activator. The activator may for instance be an enzyme. The inactive form of said drug may be referred to as a prodrug.

Typically, the prodrug is of a drug which is too unstable or insoluble to be delivered in the active state. Thus, in one embodiment the prodrug is miproxifene phosphate and the activator is an alkaline phosphatase. Miproxifene phosphate is the inactive phosphate ester of the anticancer agent miproxifene, and has ~1,000-fold greater aqueous solubility than miproxifene. It is converted to the active species by alkaline phosphatases.

Prodrugs particularly suited to delivery in compartmentalised or multi-compartmentalised gel matrices are those whose activators are not found endogenously. Some prodrug strategies rely on the delivery of an exogenous activator following the systemic, targeted delivery of a prodrug. Xu, G. & McLeod, H. L. "Strategies for enzyme/prodrug cancer therapy" Clin. Cancer Res. 7, 3314-3324 (2001) presents examples of the prodrug/activator combinations used in these strategies, which could be used as the first and second active agents in the compartmentalised or multi-compartmentalised gel matrices of the invention. The prodrug may for instance be HMR 1826, in which case the activator is human beta-glucuronidase.

Conversely, the compartmentalised or multi-compartmentalised gel matrices of the invention could be used to deliver active drugs that are deactivated by another species, giving precise control over the lifetime of the active drug. Bodor, N. & Buchwald, P. "Soft drug design: general principles and recent applications" Med. Res. Rev. 20, 58-101 (2000) presents several examples of soft drugs, which are typically deactivated by endogenous species. Compartmentalised or multi-compartmentalised gel matrices can allow the use of exogenous deactivators, or higher concentrations of endogenous deactivators than would otherwise be found in the body. For instance, an active agent may be comprised in a first region of the gel matrix and released initially, but after a certain period a second inactivating agent present in a second gel region of the matrix may be released, deactivating the first agent.

Thus, in another embodiment, the first agent is a drug that is capable of being deactivated by a deactivator compound, and the second agent is said deactivator compound. For instance, the first agent may be the drug mivacurium chloride and the second agent may be the corresponding enzyme deactivator human plasma cholinesterase.

In addition to drugs, compartmentalised or multi-compartmentalised gel matrices can also be used to carry a contrast agent for some medical imaging modality. This will allow the precise determination of the distribution of the drugs contained in the compartmentalised or multi-compartmentalised gel matrices, while keeping the marker separate from the drugs until the moment of delivery. It should be possible to encapsulate contrast agents for various medical imaging modalities, which would allow the visualization of how the drug becomes distributed within the body. The use of separate compartments for the drug and the tracer would prevent any chemical reaction between the two. Contrast agents could be included for radiography (e.g. diatrizoate, iopamidol, iodixanol), MRI (e.g. gadodiamide, gadopentetic acid), ultrasound (e.g. air bubbles), or radionuclides may be encapsulated for positron emission tomography (e.g. fludeoxyglucose ($^{18}$F)), scintigraphy (e.g. iobenguane) or single-photon emission computed tomography (e.g. Na$^{123}$I).

Accordingly, in another embodiment, the first active agent is a drug and the second active agent is a contrast agent suitable for monitoring the biodistribution of the drug. The contrast agent may for instance be a contrast agent for radiography (e.g. diatrizoate, iopamidol, iodixanol), magnetic resonance imaging (MRI) (e.g. gadodiamide, gadopentetic acid), or ultrasound (e.g. air bubbles), or radionuclides may be encapsulated for positron emission tomography (e.g. fludeoxyglucose ($^{18}$F)), scintigraphy (e.g. iobenguane) or single-photon emission computed tomography (e.g. Na$^{123}$I).

A compartmentalised or multi-compartmentalised gel matrix might be made to contain non-drug compounds and drugs in separate compartments. One possibility for the non-drug compound is a contrast agent suitable for monitoring the biodistribution of the drug, as discussed above. Other possibilities are as follows:

Targeting agents [Pouponneau, P., Leroux, J. C., Soulez, G., Gaboury, L. & Martel, S. Co-encapsulation of magnetic nanoparticles and doxorubicin into biodegradable microcarriers for deep tissue targeting by vascular MRI navigation. *Biomaterials* 32, 3481-3486 (2011)]: A recent study encapsulated doxorubicin and magnetic nanoparticles (FeCo) in poly(lactic-co-glycolic acid) microspheres, and used a modified MRI scanner to simultaneously image and steer the microparticles through blood vessels in vivo. A similar principle could be applied to the droplet encapsulates of the invention, in which case the magnetic particles and drug could be encapsulated in separate compartments.

In addition to encapsulating a drug, a compartmentalised or multi-compartmentalised gel matrices could contain a substance that responds to an external trigger in such a way as to induce release of the drug. This substance might for instance be ferromagnetic particles, which could be heated by externally applied alternating magnetic fields as used for MRI.

It might be possible to encapsulate living cells within the compartments themselves, and release them into the environment, together with compounds encapsulated separately in the same gel matrix, to trigger a particular behaviour.

Accordingly, in another embodiment, the first active agent is a drug and the second active agent is a targeting agent, a trigger or a living cell. The targeting agent or trigger may be selected from any of those listed above.

The compartmentalised or multi-compartmentalised gel matrices of the invention may contain three or more different agents, in different compartments and/or within different areas of the same compartment (e.g. within different aqueous droplets, or within the aqueous medium and the hydrophobic medium). The multi-compartmentalised gel matrix may further contain different active agents within compartments contained in different gel regions of the gel matrix.

Accordingly, in another embodiment, the multi-compartmentalised gel matrix is a multi-compartmentalised gel matrix as defined above which comprises a plurality of compartments, and which further comprises a first active agent, a second active agent, and a third active agent in compartments. In a further embodiment, the multi-compartmentalised gel matrix is a multi-compartmentalised gel matrix as defined above which comprises a plurality of gel regions, each of which regions having one or more compartments therein, and wherein the one or more compartments in each different region comprise a different active agent.

For instance, in one embodiment a first active agent is present in one or more compartments in a first gel region of the multi-compartmentalised gel matrix, a second active agent is present within one or more compartments in a second gel region of the gel matrix, and a third active agent is present one or more compartments in a third gel region of the gel matrix. In one aspect of this embodiment, the first, second and third active agents are the same.

In another embodiment, the multi-compartmentalised gel matrix comprises a first gel region having one or more compartments therein each comprising two or more aqueous droplets, wherein a first said aqueous droplet comprises a first active agent and a second said aqueous droplet comprises a second active agent. The said multi-compartmentalised gel matrix further comprises a second gel region having one or more compartments therein each comprising two or more aqueous droplets, wherein a first said aqueous droplet comprises a first active agent and a second said aqueous droplet comprises a first active agent.

The third active agent may for instance be a therapeutic agent, a diagnostic agent, a drug for use together in a combination therapy with the first or second agent, a prodrug, an activator compound for a prodrug, a deactivator compound for an active drug, or a contrast agent for monitoring the biodistribution of the first or second agent. Alternatively, the first, second and third active agents may be reactant compounds for reacting together in a chemical reaction.

Typically the first, second and third active agents are present in the compartmentalised or multi-compartmentalised gel matrix in a predetermined proportion. As mentioned above, the delivery of several drugs encapsulated in different compartments would allow precise control over dosage proportions. This may be beneficial for the delivery of drugs with independent mechanisms of action. Also, their uptake by cells in fixed proportions could be expected to increase their overall efficacy, and decrease the probability of resistance developing to any one of the drugs.

Some non-limiting examples of combinations of three or more drugs which can be employed in the compartmentalised or multi-compartmentalised gel matrix of the invention (for instance each drug in a separate compartment) include the following cancer therapies: ABVD (doxorubicin, bleomycin, vinblastine and dacarbazine) for Hodgkin's lymphoma, CHOP (cyclophosphamide, doxorubicin, vincristine and prednisone) for non-Hodgkin's lymphoma, and CMF (cyclophosphamide, methotrexate and 5-fluorouracil) for breast cancer.

It is also reasonable to expect that compartmentalised gel matrices might be used to encapsulate substances not presently delivered in combination. The ideal combination of compounds would consist of parent compounds that are stable separately, and following triggered release from a compartment, react to form an active, unstable compound. The instability of the active compound would ensure that areas far from the triggered region are not affected.

As has been discussed above, the composition of the gel matrix may be chosen to become more permeable to a volume of hydrophobic medium in response to a particular external stimulus. This is useful in the application of the gel matrices of the invention for drug delivery. In some further exemplary embodiments of the invention which are particularly useful in drug delivery, the compartments within each gel region may themselves have a stepwise response to a stimulus. For instance, each gel region may comprise a plurality of compartments wherein one or more compartments within the said plurality release their contents at a different rate to the other compartments in the plurality in response to a stimulus. For example, one or more compartments within the plurality of compartments in a gel region may release its contents slowly at low temperatures (e.g. 20 to 40° C.), while other compartments within the plurality may release their contents more rapidly at those temperatures. Alternatively or additionally, one or more compartments within a gel region may comprise two or more aqueous droplets, the contents of which is released at differing rates in response to the same stimulus. For instance, one aqueous droplet may release its contents more rapidly at low temperatures (e.g. 20 to 40° C.) than another droplet within the same compartment.

The release of the contents of particular compartments, or aqueous droplets within compartments, within a particular region of gel may be controlled by modifying the layers or bilayers of amphipathic molecules that surround the compartments (or aqueous droplets therein). For instance, as mentioned above, when the compartmentalised or multi-compartmentalised gel matrix loses its form or becomes more permeable, one or more layers of amphipathic molecules within one or more compartments does not rupture and hence the contents of said one or more layers is not released to the environment. The contents of said one or more layers may be released in response to a further external stimulus, or to further exposure to the same stimulus that caused the gel matrix to lose its form or become permeable.

The external monolayers or bilayers of two or more compartments within the same compartmentalised gel matrix or multi-compartmentalised gel matrix (e.g. within the same gel region) may for instance be sensitive to the same stimulus and the compartments may therefore be capable of releasing their contents simultaneously upon exposure to that stimulus. In other embodiments, the external monolayers or bilayers of two or more compartments within the same compartmentalised gel matrix or multi-compartmentalised gel matrix (e.g. within the same gel region) may have different stabilities, and the compartments may therefore be capable of releasing their contents into the environment at different times, in response to different stimuli, or for instance in response to different levels or magnitudes of the same stimulus. For example, a first compartment in a gel matrix may be capable of releasing its contents in response to a change in pH, whereas a second compartment in the gel matrix may be capable of releasing its contents in response to a change in temperature.

Alternatively, two or more aqueous droplets within the same compartment may release their contents in response to different levels of the same stimulus. Thus, for example, a first aqueous droplet may be capable of releasing its contents in response to a relatively small change in pH or temperature, whereas a second aqueous droplet may only release its contents in response to a larger change in pH or temperature. Additionally or alternatively, one or more of the bilayers inside the compartment may be sensitive to a stimulus such that the contents of two or more aqueous droplets therein may be combined.

Thus, in some embodiments, multiple aqueous droplets within the same compartment are capable of releasing their contents into the environment simultaneously, e.g. upon exposure to an external stimulus such as a change in pH or temperature. The contents referred to here may be first, second and/or third active agents as defined above, or any other compound or composition for delivery from within the compartment.

Accordingly, in embodiments of the compartmentalised or multi-compartmentalised gel matrix of the invention in which the compartment comprises a monolayer or bilayer of amphipathic molecules, the stability of said monolayer or bilayer may be sensitive to a stimulus. The stimulus is typically an external stimulus.

Also, in embodiments of compartmentalised or multi-compartmentalised gel matrix of the invention, in which the one or more compartments comprise a plurality of monolayers and/or bilayers of amphipathic molecules, the stabilities of one or more of said monolayers and/or bilayers may be sensitive to a stimulus. In some embodiments, the stability of at least one of said monolayers and/or bilayers is sensitive to a stimulus. The stimulus is typically an external stimulus. In other embodiments, the stability of more than one of said monolayers and/or bilayers is sensitive to a stimulus. In other embodiments, the stabilities of each and every one of said monolayers and/or bilayers is sensitive to a stimulus. The stimuli to which the layers are sensitive may be the same or different.

In embodiments of the compartmentalised or multi-compartmentalised gel matrix of the invention described herein in which part of an inner layer of amphipathic molecules contacts an outer layer of amphipathic molecules, thereby forming a bilayer of said amphipathic molecules at an interface between the aqueous droplet and the gel matrix or aqueous layer surrounding the hydrophobic medium (i.e. an "external bilayer"), the stability of said bilayer may be sensitive to a stimulus. The stimulus is typically an external stimulus.

Also, in embodiments of the compartmentalised or multi-compartmentalised gel matrix of the invention described herein in which the droplet encapsulate comprises a plurality of aqueous droplets within a compartment, wherein the inner layers around more than one of said aqueous droplets contacts the outer layer to form a plurality of external bilayers, the stability of one or more of said bilayers may be sensitive to a stimulus. The stimulus is typically an external stimulus. In some embodiments, the stability of at least one of said bilayers is sensitive to a stimulus. In other embodiments, the stability of more than one of said bilayers is sensitive to a stimulus. In other embodiments, the stabilities of each and every one of said bilayers is sensitive to a stimulus. The stimuli to which the external bilayers are sensitive may be the same or different.

In embodiments of the compartmentalised or multi-compartmentalised gel matrix of the invention described herein in which a compartment comprises a plurality of aqueous droplets, wherein part of the inner layer of amphipathic molecules around a first of said aqueous droplets contacts part of the inner layer of a second of said aqueous droplets, thereby forming a bilayer of the amphipathic molecules at an interface between said first and second aqueous droplets (an "internal bilayer"), the stability of said bilayer may or may not be sensitive to a stimulus. In some embodiments, the stability of said internal bilayer is sensitive to an external stimulus.

Furthermore, in embodiments of the compartmentalised or multi-compartmentalised gel matrix of the invention described herein in which a compartment comprises a plurality of said internal bilayers of amphipathic molecules, the stability of one or more of said bilayers may be sensitive to a stimulus. The stimulus may be an external stimulus. In some embodiments, the stability of at least one of said internal bilayers is sensitive to a stimulus. In other embodiments, the stabilities of each and every one of said internal bilayers is sensitive to a stimulus. The stimuli to which the internal bilayers are sensitive may be the same or different.

Typically, in these embodiments, the compartmentalised or multi-compartmentalised gel matrix of the invention is one which further comprises an active agent for delivery, such as a therapeutic agent, prodrug, diagnostic agent, or contrast agent, as described above. Alternatively, it may be one which comprises two or more such active agents for delivery. The two or more agents may be in separate compartments of the encapsulate, as defined above, or in the same compartment. For instance, the gel matrix of the invention may be a multi-compartmentalised gel matrix which comprises a first active agent and a second active agent in separate compartments in different gel regions of the gel matrix, or one which comprises first, second and third active agents in separate compartments in different gel regions of the matrix, as defined above.

The external stimuli which cause the gel matrices of the invention to lose their form or break may also be the stimuli to which the one or more layers of amphipathic molecules are sensitive. Additionally or alternatively, the stabilities of bilayers of amphipathic molecules may be controlled by including a molecule in one or more of the bilayers, such as a lipid or protein, that recognises a surface species on a target cell. The surface species may itself be a protein. The response to this recognition might be immediate destabilization of the bilayer, or it might be indirect. Accordingly, in one embodiment, the amphipathic molecules of said bilayer or bilayers comprise a molecule that recognises a surface species on a target cell, wherein the response to the recognition comprises destabilization of the bilayer or bilayers. The response may comprise immediate destabilization of the bilayer, or it may comprise indirect destabilization of the bilayer. The molecule may for instance be a lipid or a protein.

In one embodiment, the external stimulus to which one or more layers of amphipathic molecules is sensitive is a change in pH. Thus, in some embodiments the amphipathic molecules comprised in one or more compartments are selected such that a bilayer or bilayers formed therefrom rupture upon a change in pH. This can be achieved by employing a pH-sensitive lipid in the bilayer or bilayers in question. The pH-sensitive lipid may for instance be a fatty acid having a $pK_a$ when incorporated in a bilayer at or around the pH at which it is desired that the bilayer or bilayers of amphipathic molecules should become unstable. At pH's that are greater than the $pK_a$ of the fatty acid, the fatty acid will be deprotonated and therefore strongly amphipathic, and will therefore be suitable for stabilising an internal or external bilayer of a compartment. At pH's that are lower than the $pK_a$, on the other hand, the fatty acid will be protonated and less amphipathic, thereby destabilising any bilayer in which it is present. As the skilled person will appreciate, the $pK_a$ of a fatty acid in a bilayer is shifted compared to the $pK_a$ of the free fatty acid in aqueous solution. Thus, each $pK_a$ referred to herein is the $pK_a$ of the fatty acid when it is present in a bilayer of non-polymeric amphipathic molecules in the droplet encapsulate. The skilled person can readily measure the $pK_a$ of a fatty acid in a bilayer using methods which are known in the art, for instance by using known spectroscopic methods, in particular known methods which employ NMR spectroscopy.

Thus, in one embodiment of the compartmentalised gel matrix or multi-compartmentalised gel matrix of the invention, the amphipathic molecules in one or more compartments comprise a pH-sensitive lipid.

In another embodiment, the layers, bilayer or bilayers of amphipathic molecules in one or more compartments according to the invention are temperature-sensitive. Thus, the bilayer or bilayers of amphipathic molecules may in some embodiments be capable of rupturing upon exposure to an elevated temperature or upon exposure to a reduced temperature. In one embodiment, the bilayer or bilayers of amphipathic molecules are capable of rupturing upon exposure to an elevated temperature. In order to be useful for in vivo drug delivery the elevated temperature is typically around or above body temperature, i.e. around or above 37° C. Thus, in one embodiment of the compartmentalised or multi-compartmentalised gel matrix of the invention, the layers, bilayer or bilayers of amphipathic molecules are capable of rupturing upon exposure to a temperature equal to or greater than about 37° C. In another embodiment, the bilayer or bilayers of amphipathic molecules are capable of rupturing or leaking upon exposure to a temperature equal to or greater than about 40° C., or for instance equal to or greater than about 42° C. Such embodiments are useful in conjunction with local mild hyperthermia of up to 42° C., producing a corresponding local enhancement in drug release from a compartmentalised or multi-compartmentalised gel matrix in vivo.

Typically, in these embodiments, the layers, bilayer or bilayers of non-polymeric amphipathic molecules comprise a temperature-sensitive lipid. Typically, the temperature-sensitive lipid is a lipid that has a melting transition temperature $T_m$ at or around the temperature of interest at which it is desired that the layers of amphipathic molecules should become unstable. Liposomes made with such lipids are known to have a local maximum of permeability around $T_m$, attributable to the boundaries between the solid and fluid phases of the liposomal bilayer. That said, the rupturing temperature of the layer(s) or bilayer(s) of amphipathic molecules may be considerably different from, usually lower than, the transition temperature of the temperature-sensitive lipid. This is usually the case if a further lipid is present, as the presence of a further lipid can have the effect of broadening the melting transition of the temperature-sensitive lipid, and/or decreasing the peak transition temperature of the temperature-sensitive lipid. Second, the rupture temperature of a layer of amphipathic molecules surrounding an aqueous droplet or a volume of hydrophobic medium often depends on the size of said droplet or volume.

Thus, typically, the temperature-sensitive lipid employed in the bilayer or bilayers in one or more compartments according to the invention is a lipid which has a melting transition temperature, $T_m$, which is equal to or greater than the temperature of interest at which it is desired that the layers of amphipathic molecules should become unstable.

Accordingly, the temperature-sensitive lipid may be a lipid having a melting transition temperature, $T_m$, which is equal to or greater than about 37° C. More typically, it is a lipid having a melting transition temperature, $T_m$, which is equal to or greater than about 40° C. Thus, it can be a lipid having a melting transition temperature, $T_m$, of from 37° C. to 90° C., or for instance from 40° C. to 70° C. In one embodiment, the temperature-sensitive lipid is a lipid which has a melting transition temperature, $T_m$, of from 40° C. to 60° C.

As will be apparent from the above, the multi-compartmentalised gel matrix of the invention is particularly well suited to a complex delivery pattern, for example a multi-stage delivery pattern, of an active agent. By "multi-stage delivery pattern" is meant a process of delivering an active agent wherein one or more active agents are delivered in two or more separate portions. In some embodiments, the two or more portions may be intended for delivery at different times. For example, a first dosage may be intended for delivery at an initial time, and a second dosage may be intended for delay at a period thereafter (e.g. several hours or days thereafter). In some embodiments, the two or more dosages may be intended for delivery in response to different external stimuli. For instance, a first dosage may be intended for delivery in a neutral environment (e.g. in the buccal cavity) and a second dosage may be intended for delivery in an acidic environment (e.g. in the stomach). Tumors have a lower pH than the surrounding tissue and hence a first or further dosage intended for delivery in an acidic environment may also be intended for delivery in a tumor. Alternatively, a gel matrix or multi-compartmentalised gel matrix according to the invention may be designed to release a portion of an active agent at a particular time, and another portion of an active agent in response to a particular external stimulus. Thus, complex delivery patterns may be created.

The invention therefore provides a compartmentalised or multi-compartmentalised gel matrix of the invention as defined herein, for use in a method for treatment of the human or animal body by therapy. Typically, in this aspect, the compartmentalised or multi-compartmentalised gel matrix is a compartmentalised or multi-compartmentalised gel matrix of the invention as defined above which further comprises a therapeutic agent or prodrug. It may for instance be a multi-compartmentalised gel matrix which comprises two or more active agents in separate compartments, as defined above.

The invention further provides a compartmentalised or multi-compartmentalised gel matrix of the invention as defined herein, for use in a diagnostic method practised on the human or animal body. Typically, in this aspect, the compartmentalised or multi-compartmentalised gel matrix is a compartmentalised or multi-compartmentalised gel matrix of the invention as defined above which further comprises a diagnostic agent or a contrast agent. It may for instance be one which comprises two or more active agents in separate compartments, as defined above.

The compartmentalised and multi-compartmentalised gel matrices of the invention are further of great use in "bottom-up" synthetic biology. The compartmentalised and/or multi-compartmentalised gel matrices of the invention may be used to build protocells, and hence a proto-tissue, and further even a proto-organ in a hierarchical manner. The hierarchy is as follows: proto-organelle→protocell→proto-tissue→(proto-organ). The arrow symbol "→" indicates "constructed from". Thus, a protocell acts as the scaffold or basic unit from which proto-tissue and proto-organs may be built.

As used herein, the term "protocell" or "proto-cell" is intended to mean a synthetic mimic of a biological cell. The term "protoorganelle" or "proto-organelle" is intended to mean a synthetic mimic of an organelle such as may be found in a biological cell. Similarly the term "prototissue" or "proto-tissue" should be taken to mean a synthetic mimic of a biological tissue. Further, the term "protoorgan" or "proto-organ" should be taken to mean a synthetic mimic of a biological organ.

For a protocell and a prototissue to be of use in mimicking biological cells and tissue, a crucial feature is the presence of a viscous fluid or a gel-like material between the proto-organelles (similar to cytoplasm), and between the protocells (mimicking the extracellular matrix), respectively. In the compartmentalised or multi-compartmentalised gel matrix of the invention, the gel of the gel matrix between one or more compartments may act as a mimic of cellular cytoplasm or as the extra-cellular matrix, as described in the following paragraphs.

Depending on the number of compartments within the gel matrix and the number of aqueous droplets within each compartment, the gel matrix can either act as a protocell or a prototissue. The possibilities are shown in detail in FIG. 1 and described in Example 1. For instance, a single aqueous droplet in a compartment comprising a volume of hydrophobic medium acts as a proto-organelle. A plurality of proto-organelles (that is, aqueous droplets) housed in the same multi-compartmentalised gel matrix but in different compartments would constitute a protocell (as shown in Image (i) in FIG. 1). Many such protocells when connected through bilayers would form a multi-gel prototissue (as shown in Image (ii) in FIG. 1). If the gels containing each protocell are joined, the prototissue in this scenario may be described as a multi-compartmentalised gel matrix comprising a plurality of gel regions, comprising a plurality of compartments in each of said gel regions.

Another way of constructing a prototissue using the compartmentalised or multi-compartmentalised gel matrices of the invention is to incorporate a number of protocells in the same gel. A protocell in this scenario is made by a collection of aqueous droplets in single volume of hydrophobic medium in a compartment, each of the aqueous droplets being proto-organelles (as shown in Image (iii) in FIG. 1).

A key difference between the proto-organelles formed in Images (ii) and (iii) of FIG. 1 is the nature of the aforementioned bilayers. In the compartmentalised and multi-compartmentalised gel matrices of the invention, a compartment of the invention typically comprises an outer layer of amphipathic molecules surrounding the volume of hydrophobic medium therein, and one or more inner layers of amphipathic molecules surrounding the or each aqueous droplet therein. When the compartmentalised or multi-compartmentalised gel matrix of the invention is used or for use in synthetic biology, the layers of amphipathic molecules are typically monolayers of lipid molecules. Accordingly, a part of one such layer contacts a part of another such layer, a lipid bilayer is usually formed. In the embodiment shown in Image (ii) of FIG. 1, a proto-organelle has an individual communication line (bilayer) comprising a part of the layer of amphipathic molecules surrounding the aqueous droplet in each compartment and a part of the layer of amphipathic molecules surrounding the volume of hydrophobic medium in each compartment. By contrast, in the embodiment shown in Image (iii) of FIG. 1, the proto-organelles can perform more complex communication patterns, because the same bilayer is shared by at least two proto-organelles. A network of prototissues as in (iii) could be the basis of mimicking an organ (as shown in Image (iv) of FIG. 1).

Thus, the present invention provides a protocell comprising a multi-compartmentalised gel matrix according to the invention, wherein each compartment in the plurality of compartments comprises an aqueous droplet.

The present invention provides a prototissue comprising a plurality of protocells, wherein one or more of said protocells is a multi-compartmentalised gel matrix according to the invention, wherein each compartment in the plurality of compartments comprises an aqueous droplet. In some embodiments of this aspect of the invention, each compartment in the said plurality of compartments comprises exactly one aqueous droplet.

The present invention also provides a prototissue comprising a plurality of protocells, wherein two or more of said protocells is a multi-compartmentalised gel matrix according to the invention, wherein each compartment in the plurality of compartments comprises an aqueous droplet. In some embodiments of this aspect of the invention, at least one protocell which is a multi-compartmentalised gel matrix according to the invention comprises a different gel composition to at least one other protocell which is a multi-compartmentalised gel matrix according to the invention.

The present invention also provides a prototissue comprising a plurality of protocells, wherein the said prototissue is a multi-compartmentalised gel matrix according to the invention comprising a plurality of compartments, wherein each compartment comprises a plurality of aqueous droplets. In some embodiments of this aspect of the invention, the said multi-compartmentalised gel matrix comprises a plurality of gel regions.

The present invention also provides a protoorgan comprising a plurality of prototissues of the invention.

The present invention further provides the use of a protocell according to the invention in synthetic biology.

The present invention further provides the use of a prototissue according to the invention in synthetic biology.

The present invention further provides the use of a protoorgan according to the present invention in synthetic biology.

Mimics of biological species according to the invention (such as proto-organelles contained in a compartmentalised or multi-compartmentalised gel matrix according to the invention, or protocells, prototissues and protoorgans according to the invention) are particularly robust. They may therefore be subjected to a wide variety of experimental conditions while resisting damage. For example, a synthetic biological species according to the invention may be subjected to a series of experimental conditions with a low risk of damage. For instance, a synthetic biological species according to the invention may be moved with tweezers, pressurised, stretched, punctured, injected or washed without losing its structural integrity. This is particularly advantageous in synthetic biology as it means that a biological mimic such as a prototissue may be subjected to a series of experiments without damage.

Unlike many previous models for biological cells, the present system is capable of modelling a biological cell (or a tissue) where individual organelles (or cells) are demarcated by separate lipid bilayer membranes. The protocell based on multi-compartmentalised gel matrix of the invention makes it possible to include proto-organelles with separate bilayers, as well as with shared bilayers. Moreover, the communication between two biological cells is through membrane proteins (e.g., gap junctions) or diffusion through the cytoplasm. The adjacent placement of two bilayers supported by a gel matrix may enable the multi-compartmentalised gel matrix of the invention to model both of these transport mechanisms.

The gel matrices of the present invention are particularly advantageous as the protocell model described herein has the capacity to be functionally upgraded or used in other applications targeted to membrane protein studies. For example, because lipid bilayers can form on a hydrated support cushion, the inclusion of an intervening aqueous layer between a hydrogel and an aqueous droplet in oil (as in a nested compartment of the invention, FIG. 6) demonstrates the possibility of forming concentric lipid bilayers akin to those in organelles with double bilayers (mitochondrion, nucleus) in the biological cell.

It is further envisaged that the multi-compartmentalised and compartmentalised gel matrices of the invention, and biological mimics constructed from said matrices, may be able to interface with biological cells or tissues.

The multi-compartmentalised gel matrix of the invention provides a means or preparing one or more double bilayers and fixing their position in relation to one another. Furthermore, one or more membrane proteins may be inserted into the said bilayers. The position and orientation of two or more such membrane proteins relative to one another may be fixed in the gel matrix. The multi-compartmentalised gel matrix of the invention therefore provides a very useful platform for the study of bilayers and membrane proteins therein, and typically of double bilayers and proteins therein. The multi-compartmentalised gel matrix therefore provides a useful system for the investigation and/or screening of membrane proteins spanning a double bilayer, and/or investigation or screening of the interactions of separate membrane proteins within the separate bilayers forming a double bilayer. The multi-compartmentalised gel matrix is also useful in the investigation and/or screening of analytes which interact with membrane proteins which span or interact across double bilayers. Typically the said membrane protein is an ion channel. For instance, the effect of different ligands on the folding and function of ion channels may be studied.

Accordingly, the invention further provides the use of a multi-compartmentalised gel matrix of the invention as defined herein in a method of investigating and/or screening a membrane protein which spans two bilayers. In another aspect the invention further provides the use of a multi-compartmentalised gel matrix as defined herein in a method of investigating and/or screening membrane proteins which interact across a double bilayer. In another aspect the invention provides the use of a multi-compartmentalised gel matrix of the invention as defined herein in a method of investigating and/or screening an analyte which interacts with a membrane protein that spans a double bilayer, or which interacts with membrane proteins which themselves interact across a double bilayer.

Techniques for studying membrane proteins in lipid bilayers are well known in the art. For example, the voltage dependence of the properties of the membrane protein may be determined. The function of a channel or pore may be determined by measuring, for example, an ionic current flowing across the lipid bilayer through a membrane protein. The function of a transporter may be determined by measuring the amount of a molecule translocated across the lipid bilayer, for example by mass spectrometry or ELISA or by using a substrate which is tagged fluorescently or radioactively.

Method of the Invention

The present invention provides a method for providing a compartmentalised or multi-compartmentalised gel matrix.

In one aspect, the invention provides a method of manufacturing a multi-compartmentalised gel matrix, the method comprising:
(i) inserting a volume of a hydrophobic medium into an incompletely gelled gel precursor via an inserting means to form a compartment;
(ii) repeating step (i) one or more times to provide a plurality of compartments in the gel precursor;
(iii) gelling the gel precursor;
(iv) inserting a volume of an aqueous medium into a said compartment via an inserting means to form an aqueous droplet therein; and
(v) repeating step (iv) a plurality of times to provide an aqueous droplet in each compartment among the plurality of compartments.

In another aspect, the invention provides a method of manufacturing a compartmentalised gel matrix comprising a nested compartment, the method comprising:
(i) inserting a volume of a hydrophobic medium into an incompletely gelled gel precursor via an inserting means to form a compartment;
(iii) gelling the gel precursor;
(vi) inserting a quantity of an aqueous medium into or near to the volume of hydrophobic medium via an inserting means to form an engulfed volume of hydrophobic medium in a layer of aqueous medium; and
(vii) inserting a volume of an aqueous medium into the engulfed volume of hydrophobic medium via an inserting means to form an aqueous droplet therein.

In some embodiments, step (vi) comprises inserting the quantity of aqueous medium into the volume of hydrophobic medium. Accordingly, the invention provides a method wherein step (vi) comprises inserting the quantity of aqueous medium into the volume of hydrophobic medium.

The multi-compartmentalised gel matrix and compartmentalised gel matrix produced according to the above methods correspond to the multi-compartmentalised gel matrix and compartmentalised gel matrix of the invention, as defined above. The materials used in the above methods are similarly as defined above in relation to the compartmentalised and multi-compartmentalised gel matrices of the invention. For instance, the aqueous medium, hydrophobic medium, gel precursor and gel matrix are as defined in relation to the above products.

The compartmentalised gel matrix and multi-compartmentalised gel matrix produced in the above methods comprise an inner and an outer layer of amphipathic molecules, as described above. These amphipathic molecules may be provided within the aqueous medium and/or the hydrophobic medium in the above methods. For instance, the hydrophobic medium may comprise amphipathic molecules and the aqueous medium may not comprise amphipathic molecules. Usually, the amphipathic molecules within a compartment are present within the hydrophobic medium. For example, the hydrophobic medium may comprise amphipathic molecules.

The order of the steps performed in the methods of the invention is variable in some but not all regards. A volume of hydrophobic medium must be inserted into a gel precursor and not a gel matrix to form a compartment. Accordingly, steps (i) and (ii) are performed before step (iii). Similarly, a volume of aqueous medium can usually only be inserted into an engulfed volume of hydrophobic medium after said volume of hydrophobic medium has been engulfed in an aqueous layer. Accordingly, step (vi) is performed before step (vii).

Where the method is a method of providing a multi-compartmentalised gel matrix, the order in which aqueous droplets are inserted into the compartments is not particularly limited. Where a plurality of aqueous droplets is inserted in one or more compartments among plurality of compartments, a first aqueous droplet may be inserted to each compartment among the plurality of compartments before a second aqueous droplet is added to any compartment. Alternatively, two or more aqueous droplets may be inserted into one compartment of the plurality of compartments before any aqueous droplets are added to another compartment of the plurality of compartments.

In some embodiments, step (iv) is repeated to provide a further aqueous droplet in at least one compartment among the plurality of compartments. In some embodiments, step (iv) is repeated a plurality of times to provide a plurality of aqueous droplets in each compartment among the plurality of compartments. Thus, the invention provides a method wherein step (iv) is repeated to provide a further aqueous droplet in at least one compartment among the plurality of compartments. The invention further provides a method wherein step (iv) is repeated a plurality of times to provide a plurality of aqueous droplets in each compartment among the plurality of compartments.

The two above-mentioned aspects of the methods of the invention may be combined. Thus, the present invention also provides a method of producing a multi-compartmentalised gel matrix comprising one or more nested compartments, the method comprising:
(i) inserting a volume of a hydrophobic medium into an incompletely gelled gel precursor via an inserting means to form a compartment;
(ii) repeating step (i) one or more times to provide a plurality of compartments in the gel precursor;
(iii) gelling the gel precursor;
(iv) inserting a volume of an aqueous medium into a said compartment via an inserting means to form an aqueous droplet therein;
(v) repeating step (iv) a plurality of times to provide an aqueous droplet in each compartment among the plurality of compartments;
(vi) inserting a quantity of an aqueous medium into or near to a volume of hydrophobic medium via an inserting means to form an engulfed volume of hydrophobic medium in a layer of aqueous medium; and
(vii) inserting a volume of an aqueous medium into the engulfed volume of hydrophobic medium via an inserting means to form an aqueous droplet therein.

The order of steps in the above method of producing a multi-compartmentalised gel matrix comprising one or more nested compartments is variable in some regards. The order of steps (iv) to (vii) is somewhat variable. In some embodiments, one or more engulfed droplets may be formed before any aqueous droplets are inserted into any compartments. That is, step (vi) may be performed and optionally repeated one or more times before steps (iv) and (v) are performed. Similarly, steps (vi) and (vii) may be performed and optionally repeated one or more times before steps (iv) and (v) are performed.

Thus, the invention provides a method of manufacturing a multi-compartmentalised gel matrix according to the invention wherein steps (i), (vi) and (vii) are performed multiple times to provide a multi-compartmentalised gel matrix comprising a plurality of nested compartments.

In the method of the invention, amphipathic molecules are introduced into the compartments of the invention. Usually, the amphipathic molecules will self-assemble into the layers of amphipathic molecules present in the compartmentalised and multi-compartmentalised gel matrices of the invention. That is, the amphipathic molecules typically self-assemble into an inner layer at the interface between each aqueous droplet and the surrounding volume of hydrophobic medium, and an outer layer around each volume of hydrophobic medium.

In the methods of the invention, amphipathic molecules may be introduced into the gel precursor within the volume of hydrophobic medium in step (i). Alternatively or additionally, amphipathic molecules may be introduced within the volume of aqueous medium in steps (iv) to (vii). Typically, if amphipathic molecules are introduced into a compartment in the quantity of aqueous medium that engulfs a volume of hydrophobic medium then amphipathic molecules are also introduced into that compartment either in the hydrophobic medium or the aqueous medium that forms the aqueous droplet(s) in the compartment. Usually the amphipathic molecules that are introduced into a compartment are introduced with the hydrophobic medium in step (i).

Thus, the invention provides a method of manufacturing a compartmentalised or multi-compartmentalised gel matrix according to the invention wherein the hydrophobic medium and/or the aqueous medium comprises amphipathic molecules. The invention further provides a method of manufacturing a compartmentalised or multi-compartmentalised gel matrix according to the invention wherein the hydrophobic medium comprises amphipathic molecules. In some embodiments of this aspect of the invention, the hydrophobic medium comprises a lipid.

Usually, in the method of the invention, the compartmentalised or multi-compartmentalised gel matrix comprises an inner layer of amphipathic molecules at an interface between the or each aqueous droplet and the or each volume of hydrophobic medium.

The invention further provides a method of manufacturing a compartmentalised or multi-compartmentalised gel matrix according to the invention wherein the hydrophobic medium and/or the aqueous medium comprises amphipathic molecules and the compartmentalised or multi-compartmentalised gel matrix comprises an inner layer of the amphipathic molecules at an interface between the or each aqueous droplet and the or each volume of hydrophobic medium.

Typically, in the method of the invention, the compartmentalised or multi-compartmentalised gel matrix comprises an outer layer of amphipathic molecules around the or each volume of hydrophobic medium.

The invention further provides a method of manufacturing a compartmentalised or multi-compartmentalised gel matrix according to the invention wherein the hydrophobic medium and/or the aqueous medium comprises amphipathic molecules and the compartmentalised or multi-compartmentalised gel matrix comprises an outer layer of the amphipathic molecules around the or each volume of hydrophobic medium. In some embodiments of this aspect of the invention, the said outer layer of amphipathic molecules is at an interface between the volume of hydrophobic medium and the gel matrix. In some embodiments of this aspect of the invention, the said outer layer of amphipathic molecules is at an interface between the volume of hydrophobic medium and the aqueous layer.

The invention further provides a method of manufacturing a compartmentalised or multi-compartmentalised gel matrix comprising an active agent as described above wherein the hydrophobic medium and/or the aqueous medium comprise an active agent.

The invention further provides a method of manufacturing a compartmentalised or multi-compartmentalised gel matrix comprising an active agent as described above wherein the aqueous medium comprises a membrane protein.

Method of Producing Gel Matrix Having Multiple Gel Regions

In a further aspect, the invention also provides methods of producing a multi-compartmentalised gel matrix comprising more than one gel region.

In some embodiments, the method of producing a multi-compartmentalised gel matrix comprising more than one gel region involves: (a) producing a first compartmentalised or multi-compartmentalised gel matrix according to a method of the invention; and (b) joining a second gel matrix thereto, wherein the second gel matrix has a different composition to the first gel matrix.

The method of joining the second gel matrix to the first is not particularly limited. For instance, a gel precursor may be placed in contact with the first gel matrix and then gelled. The gel matrices are joined by the said gelling.

In another embodiment, a part of the first gel matrix, and/or a part of the second gel matrix, that are placed in contact with one another may be incompletely gelled. For example, a part of the second gel matrix may be partially melted, and/or a part of the first gel matrix may be partially melted. A join is effected where an incompletely gelled part of one or other of the gel matrices gels in contact with the other gel matrix.

In other embodiments, the first and second gel matrices may be joined by other means including, for example, an adhesive or by the application of pressure. In still further embodiments, the first and second gel matrices may not be irreversibly joined but may be held together. For instance, the first and second gel matrices may be clamped together by clamping means (e.g. tweezers or a solid casing).

Where a multi-compartmentalised gel matrix is formed by joining a gel matrix manufactured according to a method of the invention to a second gel matrix, the second gel matrix may or may not be a compartmentalised or multi-compartmentalised gel matrix of the invention. In some embodiments, the second gel matrix is a compartmentalised or multi-compartmentalised gel matrix of the invention. In the said embodiments, the method of manufacturing a multi-compartmentalised gel matrix according to the invention involves: (a) producing a first compartmentalised or multi-compartmentalised gel matrix according to a method of the invention; (b) producing a second compartmentalised or multi-compartmentalised gel matrix according to a method of the invention; and (c) joining the first and second gel matrices, wherein the second gel matrix has a different composition to the first gel matrix.

The number of gel matrices which may be joined as described above is not particularly limited. Accordingly, a method of manufacturing a compartmentalised or multi-compartmentalised gel matrix according to the invention involves joining together a plurality of gel matrices, some or all of which are compartmentalised or multi-compartmentalised gel matrices according to the invention.

A further method of the invention, which is a method of providing a multi-compartmentalised gel matrix comprising two or more gel regions, involves adding a further gel region to a compartmentalised or multi-compartmentalised gel matrix according to the invention, and then providing one or more compartments in said further gel region.

Thus, in some embodiments the invention provides a method of manufacturing a multi-compartmentalised gel matrix, said method comprising manufacturing a compartmentalised or multi-compartmentalised gel matrix according to any above-described method, and further comprises:
(iiia) providing a further gel precursor in contact with the gel matrix formed in step (iii); and
(iiib) repeating any above-described method of providing a compartmentalised or multi-compartmentalised gel matrix on said further gel precursor.

In the said embodiments, the order of steps of the methods of the invention are variable as described above. As described above, the insertion of one or more volumes of hydrophobic medium is performed upon a gel precursor and hence step (i) must be performed before step (iii) in each iteration of the process of the invention. However, the time at which one or more aqueous droplets is inserted into the compartments formed in the process of the invention is variable.

In some embodiments, one or more compartments are formed in a first gel precursor (steps (i) and (ii)), which is then gelled (step (iii)), forming a first gel matrix. A second gel precursor is added to the first gel matrix (step (iiia)) and one or more compartments are formed therein. The second gel precursor is then gelled. The insertion of one or more aqueous droplets into the compartments is performed subsequently.

In typical embodiments of the methods of the invention, one or more aqueous droplets is inserted in the one or more compartments of the first gel matrix (steps (iv) and (v)) before step (iiia) is performed.

In yet other embodiments of the methods of the invention, one or more aqueous droplets is inserted into compartments within the first and/or second gel precursor.

Steps (iiia) and (iiib) may be repeated a plurality of times, forming a gel matrix comprising a plurality of regions.

The Gelling Step

Gelling is the process by which the gel precursor is transformed into a gel. The term "gelling" herein particularly refers to the process by which a gel precursor becomes a gel matrix, or a part of a gel matrix, according to the invention. The gel precursor is typically flowable, whereas the gel matrix is typically not flowable and may be referred to as firm. According, the gelling step of the process of the invention is typically the step during which the shape of the gel matrix is determined.

The gelling process involves the formation of cross-links between gel particles in the gel precursor. The cross-links may, for example, involve the entanglement of gel particles in the gel precursor, forming physical bonds. Alternatively or additionally, the cross-links may be covalent bonds formed between gel particles in the gel precursor. The formation of cross-links between gel particles causes the gel matrix to be robust. By "robust" is meant that the gel matrix may be resistant to mechanical wear and tear, for instance it may be resistant to deformation. In consequence, the gel matrix may therefore be manipulated after it has been created. For example, the gel matrix of the invention may be cut, joined or stapled in order to alter the shape of the matrix or to combine two or more gel matrices.

The precise types of cross-link formed varies with the gel particles and other species present in the gel precursor. Many types of gel precursor, and methods of gelling said gel precursors, are known in the art. A few exemplary embodiments are described below.

The gelling process may comprise an irradiation step (e.g. by ultraviolet light) in order to initiate cross-linking (e.g. polymerisation). In such a case, the gel precursor may comprise a photoinitiator. Another method by which gelling may be achieved is by thermal initiation of cross-linking, for example thermal initiation of polymerisation. The gelling step of the invention may therefore comprise a heating or baking step. The gelling step may comprise an incubation step, wherein the gel precursor is maintained at a particular temperature for a period of time.

Usually the gelling step involves a temperature-initiated sol-gel transition. A temperature-initiated sol-gel transition is a process wherein the transformation of a sol (that is, a fluid comprising gel particles, e.g. a gel precursor) into a gel is initiated by a temperature change. Typically the temperature-initiated sol-gel transition involves cooling a sol-gel from above its sol-gel transition temperature to below its sol-gel transition temperature. The sol-gel transition temperature is the temperature at which the sol-gel transforms from a sol to a gel (and vice versa). The gelling of a sol-gel in sol form to form a gel at the sol-gel transition temperature of the sol-gel is typically reversible. Typically, therefore, the gelling process of the methods of the invention involves the formation of physical bonds. For instance, the said gelling process does not involve the formation of covalent bonds. This may be advantageous where it is desired that the gel matrix formed by the methods of the invention can later dissolve, for instance in vivo.

An example of a sol-gel is a hydrogel, e.g. agarose. Hydrogels are preferred in the methods of the invention.

In some embodiments of the methods of the invention, the gel precursor comprises a sol-gel and the gelling step involves a cooling step. For example, in the said embodiments the gelling step may involve cooling the gel precursor comprising a sol-gel from above to below the sol-gel transition temperature of the gel precursor.

Thus, the invention provides a method of manufacturing a compartmentalised or multi-compartmentalised gel matrix as described herein wherein the gel precursor is a sol-gel and step (iii) comprises cooling the gel precursor to a temperature below its sol-gel transition temperature.

In some embodiments of the methods of the invention, the gelling step may involve an incubation step. For example, the gel matrix may be incubated at a temperature below the sol-gel transition temperature of the constituent gel or gels after the gel matrix is formed in order to promote further gelling.

In some embodiments of the methods of the invention, the gel precursor comprises thermosetting gel particles and the gelling step may therefore involve a heating step. The said heating step may be referred to as a heat-curing step. For example, in the said embodiments the gelling step may involve heat-curing the gel precursor comprising thermosetting gel particles.

Similarly, in some embodiments of the invention, the gel precursor comprises UV-curable gel particles and the gelling step may therefore involve a UV irradiation step. In the said embodiments, the gel precursor may further comprise a photoinitiator. For example, in the said embodiments the gelling step may involve irradiating the gel precursor comprising UV-curable gel particles and optionally a photoinitiator with UV light. The said gelling step may be referred to as a UV-curing step. A UV-curing step may be carried out in addition to a cooling step and/or an incubation step as described above.

Heating Step

Where the gel precursor comprises a sol-gel, the gel precursor is typically capable of undergoing a sol-gel transition. Where the gel precursor is capable of undergoing a sol-gel transition, the gel precursor is usually in sol-form prior to step (i) of the methods of the invention. Accordingly, in some embodiments of the methods of the invention the gel precursor comprises a sol-gel and the gel precursor is initially in sol form. For example, in said embodiments the method typically involves a heating step prior to step (i) to ensure the sol-gel is in sol form prior to step (i). The initial heating step comprises heating the gel precursor to a temperature above its sol-gel transition temperature. For instance, the initial heating step may involve heating the gel precursor to at least 20° C. above its sol-gel transition temperature. E.g. the initial heating step may involve heating the gel precursor to at least 10° C. or at least 5° C. above its sol-gel transition temperature. Similarly, the initial heating step may involve heating the said gel precursor to a temperature at least 10% higher than its sol-gel transition temperature, e.g. at least 20% higher than its sol-gel transition temperature.

The initial heating step may be referred to as a melting step.

Thus, the invention provides a method of manufacturing a compartmentalised or multi-compartmentalised gel matrix as described herein wherein the gel precursor is capable of undergoing a sol-gel transition and the said gel precursor is heated to a temperature above its sol-gel transition temperature before step (i) is performed. In a preferred aspect of this embodiment, the invention provides a method wherein the heated gel precursor is further allowed to cool to a temperature within 5° C. of its sol-gel transition temperature before step (i) is performed.

Insertion of Hydrophobic Medium

The methods of the invention comprise at least one step of inserting a volume of a hydrophobic medium into a gel precursor via an inserting means. This step is hereafter referred to as step (i). Usually, step (i) is repeated a plurality of times in relation to each of one or more gel precursors to form a plurality of compartments according to the invention.

In some embodiments of the methods of the invention, the gel precursor comprises one or more regions that are incompletely gelled, while one or more other regions are gelled. Usually, the insertion of step (i) comprises inserting a volume of hydrophobic medium into an incompletely gelled region of the gel precursor. For instance, step (i) may comprise inserting a volume of hydrophobic medium into a region of gel precursor that is in sol form.

Typically, step (i) comprises inserting a volume of hydrophobic medium into a gel precursor that may subsequently be easily gelled, e.g. may be rapidly gelled. It is preferred to insert a volume of hydrophobic medium into a gel precursor that may be induced to gel by a small change in the physical environment (e.g. temperature). This is preferred as the greater the change in physical environment that is needed to gel the gel precursor, the longer the gelling process will take and the greater the possibility that the volume of hydrophobic medium may move away from the position at which it was inserted. For example, in extreme cases the volume of hydrophobic medium may escape from the gel precursor.

In some embodiments, where the gel precursor of step (i) comprises a sol-gel, said gel precursor is usually close to its sol-gel transition temperature. In one embodiment of the methods of the invention, the gel precursor comprises a sol-gel and is within 20% of its sol-gel transition temperature during step (i). For example, the said gel precursor is within 10% or preferably within 5% of its sol-gel transition temperature during step (i). In other embodiments of the methods of the invention, the gel precursor comprises a sol-gel and is within 10° C. of its sol-gel transition temperature during step (i). For example, the said gel precursor is within 5° C. or preferably within 2° C. of its sol-gel transition temperature during step (i).

Thus, the invention provides a method of manufacturing a compartmentalised or multi-compartmentalised gel matrix as described herein wherein the gel precursor is capable of undergoing a sol-gel transition and steps (i) to (iii) are performed while the gel precursor is maintained at a temperature within 5° C. of its sol-gel transition temperature. In a preferred aspect of this embodiment, the invention provides a method wherein steps (i) to (iii) are performed while the gel precursor is maintained at a temperature within 2° C. of its sol-gel transition temperature.

In some embodiments of the methods of the invention, the gel precursor comprises a sol-gel and the temperature of the gel precursor is below the sol-gel transition temperature of the gel precursor during step (i). This is possible as gelling is not an instantaneous process and so the said gel precursor may be incompletely gelled and hence capable of undergoing step (i), even at the said temperatures. However, it is preferred that, where the gel precursor comprises a sol-gel and is capable of undergoing a sol-gel transition, the temperature of the said gel precursor is above its sol-gel transition during step (i).

In typical embodiments of the methods of the invention, the gel precursor is capable of undergoing a sol-gel transition at a sol-gel transition temperature, and prior to performing the methods of the invention:
the gel precursor is heated to a temperature above its sol-gel transition temperature; and
the gel precursor is cooled to a temperature close to the sol-gel transition temperature of the gel precursor.

In preferred embodiment of the methods of the invention, the gel precursor is capable of undergoing a sol-gel transition at a sol-gel transition temperature and, prior to performing the methods of the invention:
the gel precursor is heated to a temperature at least 10% higher than its sol-gel transition temperature; and
the gel precursor is cooled to a temperature within 5° C. of its sol-gel transition temperature of the gel precursor.

In further preferred embodiments of the methods of the invention, the gel precursor is capable of undergoing a sol-gel transition at a sol-gel transition temperature and, prior to performing the methods of the invention:
the gel precursor is heated to a temperature at least 20° C. higher than its sol-gel transition temperature; and
the gel precursor is cooled to a temperature within 2° C. of its sol-gel transition temperature of the gel precursor.

Insertion Process

The methods of the invention all involve the insertion of at least one volume of a hydrophobic medium into a gel precursor, and at least one droplet of an aqueous medium into said volume of hydrophobic medium, via an inserting means.

The inserting means may be any means suitable to insert a volume of fluid into a gel matrix or a gel precursor. Thus, the inserting means usually comprises a hollow channel ending at one end in a pressurisable reservoir of fluid.

The inserting means must typically be able to insert a volume of fluid in a precise manner, for example to within 10 μm of a position. The inserting means for inserting one or more aqueous droplets into a volume of hydrophobic medium, or for inserting an aqueous layer around a volume of hydrophobic medium must typically be more accurate still. For instance, the said inserting means must be capable of inserting a volume of an aqueous medium within 1 μm to 100 μm of a desired position, e.g. within 50 μm or within 10 μm of a desired position. Accordingly, the hollow channel must have a narrow outlet suitable for inserting a volume of fluid into a gel precursor or into or near a volume of hydrophobic medium therein. Preferably, therefore, the hollow channel has an outlet with a diameter of 10 m or less, preferably 5 µm or less. Particularly where the hollow channel is used for inserting an aqueous droplet, the hollow channel preferably has an outlet with a diameter of 5 µm or less. A preferred example of a hollow channel used in the methods of the invention is a hollow needle, e.g. a hollow microneedle.

Thus, the invention provides a method of manufacturing a compartmentalised or multi-compartmentalised gel matrix according to the invention wherein the insertion means of steps (i), (ii), (iii) and (iiia) are needles, preferably microneedles.

The inserting means is typically a syringe, e.g. a Hamilton syringe.

The volume of fluid inserted by the inserting means is variable. Where the inserting means is used to insert a volume of hydrophobic medium into a gel precursor, the volume of hydrophobic medium inserted in a single step may be from 5 to 1000 µL, preferably 10 to 500 µL, more preferably 50 to 200 µL.

Where the inserting means is used to insert an aqueous droplet within a volume of hydrophobic medium, the volume of aqueous medium inserted in each inserting step may be from 1 nL to 1 µL, preferably from 5 nL to 500 nL, more preferably from 10 nL to 200 nL.

Where the inserting means is used to insert an aqueous layer around a volume of hydrophobic medium, the volume of aqueous medium inserted may be of the order of tens or hundreds of microliters, e.g. from 10 to 1000 µL, preferably from 50 to 800 µL. In some embodiments, the quantity of aqueous medium has a volume that exceeds the volume of hydrophobic medium. Thus, the invention provides a method wherein the quantity of aqueous medium inserted in step (vi) exceeds that of the volume of the hydrophobic medium that is to be engulfed.

A single insertion means may be used in the method of the invention. For instance, a microfluidics device may be able to provide suitable quantities of suitable media in succession to the same insertion means, for instance in a 3D printing method.

Two or more insertion means may be used in the methods of the invention. For instance, a first insertion means may be used to insert hydrophobic medium (that is, to perform step (i)), while a second insertion means may be used to insert aqueous medium (e.g. to perform one or more of steps (iv) to (vii)).

In some embodiments of the methods of the invention, two or more inserting means may be used in a particular step of the methods. For example, step (i) may be performed using two different inserting means. A first inserting means may insert a first type of hydrophobic medium and a second inserting means may insert a second type of hydrophobic medium. Alternatively, the first and second inserting means may be used to insert the same type of hydrophobic medium. Similarly, a first inserting means may be used to insert a first type of aqueous medium and a second inserting means may be used to insert a second type of aqueous medium. Alternatively, a first and second inserting means may be used to insert the same type of aqueous medium.

Where a first and a second inserting means are used, multiple inserting steps may be performed simultaneously. For example, two or more volumes of hydrophobic medium may be inserted simultaneously, or two or more aqueous droplets may be inserted simultaneously, or a volume of hydrophobic medium and an aqueous droplet may be inserted simultaneously. It will be appreciated that a wide variety of permutations of performing steps of the invention in parallel are possible, and that the above are provided merely as examples. Where one or more steps of the methods of the invention are performed in parallel, the methods of the invention may advantageously be performed more rapidly than where steps are performed in succession.

In some embodiments of the invention, a quantity of aqueous medium is inserted at a position near to a volume of hydrophobic medium (referred to as step (vi) hereafter). The quantity of aqueous medium inserted is typically larger than the volume of hydrophobic medium which is to be surrounded. For example, the quantity of aqueous medium may be at least twice the volume of the aqueous droplet.

During step (vi), the position at which the quantity of aqueous medium is inserted must be near to the volume of hydrophobic medium which is to be engulfed. For instance, the aqueous medium must be inserted at a position within 10 nm, e.g. within 5 nm, of the edge of the volume of hydrophobic medium. In a preferred embodiment, in step (vi) the quantity of aqueous medium is inserted into the volume of hydrophobic medium itself. That is, the outlet of the insertion means used to insert the volume of aqueous medium is placed within the volume of hydrophobic medium that is to be engulfed.

Building Up a Network of Compartments

As has been mentioned above, the gel precursor into which one or more volumes of hydrophobic medium are inserted into the methods of the invention is not gelled. However, the gel precursor is preferably in a condition close to gelling, such that a small change in physical conditions (e.g. temperature) may induce gelling. Accordingly, the gel precursor is somewhat viscous and so volumes of hydrophobic medium inserted therein do not move swiftly. Moreover, it may be possible to move a volume of hydrophobic medium after it has been inserted into the gel precursor.

The methods of the invention therefore allow the relative positions of one or more compartments to be controlled. The control over the relative positions of compartments is useful in allowing a network of gel compartments to be built according to a design.

In some embodiments, the insertion means of step (i) is not moved between repetitions of step (i). In these embodiments, each volume of inserted hydrophobic medium may be pushed to a new position by the insertion of a subsequent volume of hydrophobic medium. Alternatively, each volume of hydrophobic medium may be moved after insertion to a new position by an external stimulus. Said external stimulus may be, for example, gravity or a mechanical manipulating means. Alternatively, the gel precursor may be moved relative to the insertion means.

In some embodiments of the method of manufacturing a multi-compartmentalised gel matrix of the invention, the method of the invention comprises a step of moving the insertion means from a first position at which a first volume of hydrophobic medium is inserted to a second position. Thus, in a typical method of the invention step (ii) may comprise:

(ii) moving the insertion means of step (i) to a new position and repeating step (i), and repeating this process one or more times to provide a plurality of compartments in the gel precursor.

The method of the invention therefore provides a method of manufacturing a multi-compartmentalised gel matrix according to the invention wherein step (i) is performed multiple times and the method further comprises moving the insertion means to a new position relative to the gel precursor after performing step (i).

Also provided is a method wherein a plurality of compartments and/or nested compartments are produced and are positioned next to one another.

In those embodiments of the methods of the invention where the insertion means of step (i) and the gel precursor are moved to new positions between repetitions of step (i), complex structures may be built up. In some embodiments, the relative positions may be determined by a computer programme. In these embodiments of the methods of the invention, the position of the gel precursor and/or the insertion means of step (i) are moveable relative to one another by moveable means, and said moveable means are controlled by a computer programme. The computer programme may control the moveable means to move the insertion means and gel precursor relative to one another in a series of steps to adopt a series of relative positions, and step (i) is repeated at each relative position.

In this way, a network of compartments may be created according to a design created on and stored in the memory of a computer. For example, a network may be created by a method of 3D printing, where the 3D-printed items are the compartments produced in step (i).

Manipulating Compartments and Droplets

Once inserted, a volume of hydrophobic medium may be moved in the gel precursor. Similarly, once inserted, an aqueous droplet may be moved inside a compartment.

Typically, an aqueous droplet is manipulated within a compartment to bring the inner layer of amphipathic molecules surrounding said droplet into contact with the outer layer of amphipathic molecules surrounding the volume of hydrophobic medium. That is, the aqueous droplet may be moved into contact with the edge of the volume of hydrophobic medium in which it is contained, for instance in order to form a bilayer.

Typically, a volume of hydrophobic medium is manipulated within a gel precursor in order to move it next to another compartment. For example, a volume of hydrophobic medium may be moved to reduce the width of the gel strip separating one compartment from another.

Thus, the invention provides a method further comprising a manipulation step involving inserting a manipulation means into an aqueous droplet in a volume of hydrophobic medium and manipulating the aqueous droplet such that it is placed in contact with the outer edge of the volume of hydrophobic medium. The invention further provides said method wherein the manipulation step forms a bilayer comprising:
 (a) a part of an inner layer of amphipathic molecules at the interface between the aqueous droplet and the volume of hydrophobic medium; and
 (b) a part of an outer layer of amphipathic molecules at the outer edge of the volume of hydrophobic medium.

Any mechanical means may be used to manipulate an aqueous droplet or a volume of hydrophobic medium. Preferably, the means used to manipulate an aqueous droplet or a volume of hydrophobic medium is a micromanipulator. A micromanipulator may be, for example, a needle.

In some embodiments, a micromanipulator (e.g. a needle) is inserted into an aqueous droplet and manipulated in order to drag the aqueous droplet along its path of movement. In some embodiments, a micromanipulator (e.g. a needle) is inserted adjacent to an aqueous droplet and manipulated to push the aqueous droplet before its path of movement. Corresponding methods may apply to the movement of a volume of hydrophobic medium through a gel precursor.

Insertion of a Protein Pore

In some embodiments of the methods of the invention, the method of manufacturing a compartmentalised or multi-compartmentalised gel matrix of the invention comprises inserting a membrane protein into a bilayer, a double bilayer or a more generically-defined inner or outer layer of amphipathic molecules.

In many embodiments, a membrane protein may be incorporated into a bilayer or monolayer of amphipathic molecules by self-assembly. Thus, a membrane protein (typically a protein pore, e.g. an ion channel) may be provided to the gel matrix of the invention within a volume of hydrophobic medium during step (i) or within the aqueous medium inserted to form an aqueous droplet. Typically, the membrane protein is provided in the aqueous medium that is inserted to form an aqueous droplet.

Alternatively, a membrane protein may be inserted into a bilayer, double bilayer or inner or outer layer of amphipathic molecules in a separate step. In that case, the method may additionally comprise a step of inserting a protein pore (e.g. an ion channel). The membrane protein (e.g. a protein pore) is typically inserted into a bilayer. Accordingly, in some embodiments the methods of the invention comprise a step of inserting a membrane protein into a bilayer. The membrane protein may be provided in an aqueous medium.

Further Processing of the Gel Matrix

According to some methods of the invention, a compartmentalised or multi-compartmentalised gel matrix produced according to a method of the invention may be subjected to additional method steps. For instance, the gel matrix may be subjected to additional method steps to adapt it to a particular use.

Thus, the invention further provides a method comprising:
 (v) further processing the compartmentalised gel matrix or multi-compartmentalised gel matrix.

In some embodiments, a compartmentalised or multi-compartmentalised gel matrix produced according to a method of the invention is coated with an external layer. For example, said gel matrix may be coated with a hard shell or with a biocompatible shell.

In some embodiments, a compartmentalised or multi-compartmentalised gel matrix produced according to a method of the invention is further subjected to an additional polymerisation step such as a UV curing step. Thus, the invention provides a method wherein step (v) comprises curing the compartmentalised gel matrix or multi-compartmentalised gel matrix, preferably in ultraviolet light.

In some embodiments, a compartmentalised or multi-compartmentalised gel matrix produced according to a method of the invention is dehydrated and optionally further rehydrated. Thus, the invention provides a method wherein step (v) comprises drying the compartmentalised or multi-compartmentalised gel matrix.

EXAMPLES

General Experimental Methods

In the following Examples, the methods described below were used.

Liposome Preparation:

25 mg of 1, 2-diphytanoyl-sn-glycero-3-phosphocholine (DPhPC) (Avanti Polar Lipids, USA) was dissolved in 1 mL pentane (Chem-Lab nv, CL00-1614) in a glass vial. The lipid solution was dried under a stream of filtered nitrogen ($N_2$) to form a uniform lipid film on the glass surface. The dried lipid was suspended in a buffer (150 mM NaCl, 10 mM Tris-HCl, pH 7.5), followed by sonication and extrusion through a filter (pore size 0.2 µm) to give unilamellar liposomes. The liposome solution was diluted to a final concentration 5 mg mL$^{-1}$ DPhPC. Liposomes from Porcine brain lipid extract (Avanti Polar Lipids, USA) were made in the same way.

Oil Composition:

Lipids (DPhPC, Porcine brain lipid extract) dissolved in pentane at 10 mg mL$^{-1}$ were evaporated using a stream of filtered N$_2$. The dried lipid film was re-solubilized in a 1:1 (v/v) mixture of silicone oil (Silicone Oil AR 20, Sigma-Aldrich, 10836) and hexadecane (Sigma-Aldrich, H6703). For electrical experiments hexadecane and silicone oil were mixed in a ratio of 3:1 (v/v).

Hydrogel Composition:

1% w/v low gelling temperature agarose (Sigma-Aldrich, A9414) was dissolved in the same buffer used to make liposomes (150 mM NaCl, 10 mM Tris-HCl, pH 7.5) by heating while taking care the volume was maintained.

Hydrogel Formation and Enclosing Single and Multiple Oil Compartments in the Hydrogel:

Agarose was melted by heating up to 80° C. and poured into a 10 mm×35 mm plastic cuvette (Sigma-Aldrich, BRAND® UV cuvette, Z637157). The temperature was monitored every 30 s by means of a hand-held thermistor. At the sol-gel transition temperature of the agarose (27±1° C.), an oil/lipid mixture was injected using a Hamilton syringe to form an oil droplet inside the hydrogel. Multi-compartments of oil inside the hydrogel were formed in the same manner. After injecting one oil droplet inside the hydrogel, the syringe was withdrawn and immediately inserted to inject a second oil droplet very close to the first one. Up to 10 oil droplets (50-200 µL) could be injected in a single hydrogel block. If injected at a higher temperature when the agarose was in the sol state, the oil escaped. At a lower temperature when the agarose had already gelled, it was difficult to for the oil to displace the agarose by an equivalent volume. The hydrogel piece with the oil droplet was allowed to cool to room temperature (22±1° C.). The hydrogel block was then removed from the plastic cuvette by gently pushing.

Encapsulating Aqueous Droplets in the Oil/Hydrogel:

A 1 mL plastic syringe (BD Luer-Lok™) filled with DPhPC liposomes (2-5 m gmL$^{-1}$) was attached to a ~2 cm long Microfil® needle (CMF90UxxL, 36 gauge, 20 µm inner diameter, 90 µm outer diameter; World Precision Instruments). The needle was inserted in the encapsulated oil droplet piercing the solidified hydrogel encasing (22±1° C.), and was held on the upper edge of the oil droplet taking care that the needle end does not touch the hydrogel. By a slight push of the piston, the liposome solution was expelled to form a small aqueous droplet (100-400 µm in diameter). A quick withdrawal of the Microfil® needle from the oil droplet allowed the aqueous droplet to separate from the needle and slowly fall to the bottom of the oil chamber.

Aqueous Droplet Stability Measurements:

Many sets of agarose blocks each with encapsulated oil mixture (7.5 mg mL$^{-1}$ DPhPC) were made. 2 aqueous droplets containing liposomes (5 mg mL$^{-1}$ DPhPC) were injected inside the oil volume and placed in an incubator at 29° C. The stability criterion was the time until one of the aqueous droplets fused with the hydrogel or with each other to make a bigger droplet. The experiment was monitored every 12 h for up to 4 days. The same procedure was repeated with different sets of aqueous droplets (2, 4, 6 and 8 droplets).

Expression of ClyA Pores:

An engineered ClyA containing five mutations, S87C, L99Q, E103G, F166Y and K294R, was used (Soskine et al., "Tuning the size and properties of ClyA nanopores assisted by directed evolution", *J. Am. Chem. Soc.* 135, 13456-13463 (2013)). Monomers containing a C-terminal oligo-histidine tag were expressed in *E. coli* BL21 cells and the soluble fraction purified using Ni-NTA affinity chromatography. Oligomerization of ClyA dodecamers was triggered by the addition of 0.5% w/v β-dodecylmaltoside (DDM, GLYCON Biochemical, and GmbH) and incubation for 15 min at 37° C. Different oligomeric states and monomeric ClyA were separated by blue native polyacrylamide gel electrophoresis using 4-20% polyacrylamide gels (BN-PAGE, Bio-Rad). The band corresponding to dodecamer ClyA was excised from the gel and placed in 150 mM NaCl, 15 mM Tris.HCl, pH 7.5 supplemented with 0.2% w/v DDM and 10 mM EDTA to allow diffusion of the proteins out of the gel. The resulting oligomeric ClyA could be stored at 4° C. for up to 3 weeks.

Bilayer Formation and Capacitance Measurement:

A small piece of the insulating layer was removed from one end of a silver wire (200 µm diameter, A-M systems, USA). Ag/AgCl electrodes were made by immersing the exposed end of the silver wire in a sodium hypochlorite solution for at least 1 h. 3% w/v melted agarose was dabbed at the end of the electrodes to prevent slipping of the aqueous droplets (Holden et al., "Functional bionetworks from nanoliter water droplets", *J. Am. Chem. Soc.* 129, 8650-8655 (2007)). Current was measured across the bilayer formed between the encapsulated aqueous droplet and hydrogel by inserting an Ag/AgCl electrode (cis) into the aqueous droplet attached to the ground terminal of the headstage (Axon Instruments, USA). Another Ag/AgCl electrode (trans), connected to the active terminal of the headstage, was inserted in the hydrogel. A micromanipulator was used to control the bilayer formation by moving the aqueous droplet to touch the inner wall of the hydrogel.

For measuring the bilayer capacitance between two contiguous aqueous droplets, 2 oil droplets were injected in an agarose block as described above. The cis electrode, attached to the ground end of the patch-clamp headstage, was inserted into one oil droplet. The trans Ag/AgCl electrode was inserted into the other oil droplet. Aqueous droplets were injected directly onto the electrode using a micro needle. The distance of the aqueous droplets was adjusted using a micromanipulator to form bilayers with the hydrogel.

Single Channel Electrical Measurement of ClyA, and Thrombin Blocking of ClyA:

For electrical recording ~1-10 ng oligomeric ClyA was added to one of the aqueous droplets, the droplet connected to the cis electrode; the trans electrode was connected to an empty aqueous droplet.

Stock solutions of human thrombin (huThr) were prepared by dissolving the lyophilized protein (Sigma-Aldrich, T6884) inMilli-Q® water up to a concentration of 0.2 NIH units µL$^{-1}$. The protein was aliquoted and stored at −20° C. The molar concentration of HT was calculated from its unit concentrations, with 1 NIH unit mL$^{-1}$=10 nM.

huThr (10 nM) was added to an aqueous droplet containing ClyA (1-10 ng), the droplet connected to the cis electrode; the trans electrode was connected to an empty aqueous droplet. Electrical signals were amplified using an Axopatch 200B patch clamp amplifier (Axon Instruments) and digitized with a Digidata 1440 A/D converter (Axon Instruments). Data were recorded using the Clampex 10.4 software (Molecular Devices) and subsequent analysis was carried out using the Clampfit software (Molecular Devices). Electrical recordings by applying a 2 kHz low-pass Bessel filter and a 10 kHz sampling rate. All electrical measurements were conducted at 25° C.

Optical Measurements:

For optical measurements, ClyA monomers were added to 0.2% w/v DDM in 150 mM NaCl, 15 mM Tris.HCl pH 7.5. The ClyA oligomer (20-80 $\mu gmL^{-1}$) was mixed with DPhPC liposomes to perform the optical experiments.

A fluorescent stereo microscope (Leica M165 FC) was used for all optical experiments. Fluorescence images were acquired using a GFP filter (10 447 408 Filter Set ET GFP LP-M205FA/M165FC). ImageJ software (Fiji) was used to analyze and process recorded images.

Example 1: Construction of a Proto-Tissue

The concept of bottom-up design of artificial cells and modular tissues is illustrated in FIG. 1. A prototissue is a mimic of a biological tissue and comprises an ensemble of protocells. A network of prototissues is considered a proto-organ. A simple bottom-up hierarchical construction would therefore be: proto-organelle→protocell→prototissue→proto-organ. In FIG. 1, an exemplary proto-organelle is shown and is an aqueous droplet immersed in an oil/lipid bath to cover it with a lipid monolayer. To produce a system with hierarchical properties, the proto-organelle in oil is encased in a hydrogel. The aqueous droplet-hydrogel interface is stabilized by a lipid bilayer which may have a membrane protein inserted therein to enable a function (such as chemical and electrical communication, or sensing). Protocells are comprised of proto-organelles. A protocell may therefore be created by multi-compartment encapsulation of single aqueous droplets (proto-organelles) in a hydrogel to form a multi-hydrogel protocell, as shown in FIG. 1 (i). An assembly of such hydrogel-protocells, ideally connected through lipid bilayers, will form a prototissue as shown in FIG. 1 (ii). Alternatively, multiple aqueous droplets (proto-organelles) in the same oil compartment (encased in hydrogel) will also constitute a protocell. Multi-compartmentalization of protocells in a hydrogel will also constitute a uni-hydrogel prototissue as illustrated in FIG. 1 (iii). A collection of such prototissues would be a proto-organ, as shown in FIG. 1 (iv).

The advantageous elements of the compartmentalised gel matrix of the invention as regards the formation of proto-organelles, protocells, prototissues and proto-organs are the ability to form multiple levels of compartmentalization, modularity and spatial flexibility. The modular design has the advantage of structure-function interconversion; for instance, an agarose unit can be a proto-organelle, a protocell or a prototissue depending on the experimental requirements. Because the hydrogel pieces can be spatially manipulated, a protocell can be introduced into or removed from a prototissue, e.g., by adding or removing a piece of hydrogel (i↔ii in FIG. 1); injecting aqueous droplets can convert a protocell into a prototissue (i↔iii in FIG. 1); and prototissues can be assembled into or removed from a proto-organ by adding or removing a piece of hydrogel (iii↔iv in FIG. 1).

Example 2: Encapsulation of Proto-Organelles in a Multi-Layered Hydrogel to Form a Protocell The process described above is used and is illustrated step-by-step in FIG. 2 (a). Owing to its ease of availability, low cost, and biocompatibility, agarose was chosen as the hydrogel matrix for droplet encapsulation. Low gel agarose (1% w/v in 150 mM NaCl, 10 mM Tris-HCl, pH 7.5) was melted by heating up to 80° C., poured into a mold, and allowed to cool down to 27° C. (step i). At this sol-gel transition point of the agarose, 50 to 100 µL of hexadecane/silicone oil mixture containing 7.5 mg mL$^{-1}$ DPhPC was injected inside the hydrogel using a steel needle (specifically, a steel microneedle), and retracted without delay (step ii). The oil drop was firmly encased as the agarose completely gelled upon reaching the room temperature (~22° C.). Aqueous droplets were then injected in the oil using a microneedle (step iii). The aqueous droplet settled at the bottom of the oil volume, stabilized by a lipid bilayer at the aqueous-hydrogel interface (step iv). Such an aqueous droplet in oil is a model proto-organelle, and a collection of such proto-organelles in the hydrogel a model protocell.

Figure 2:
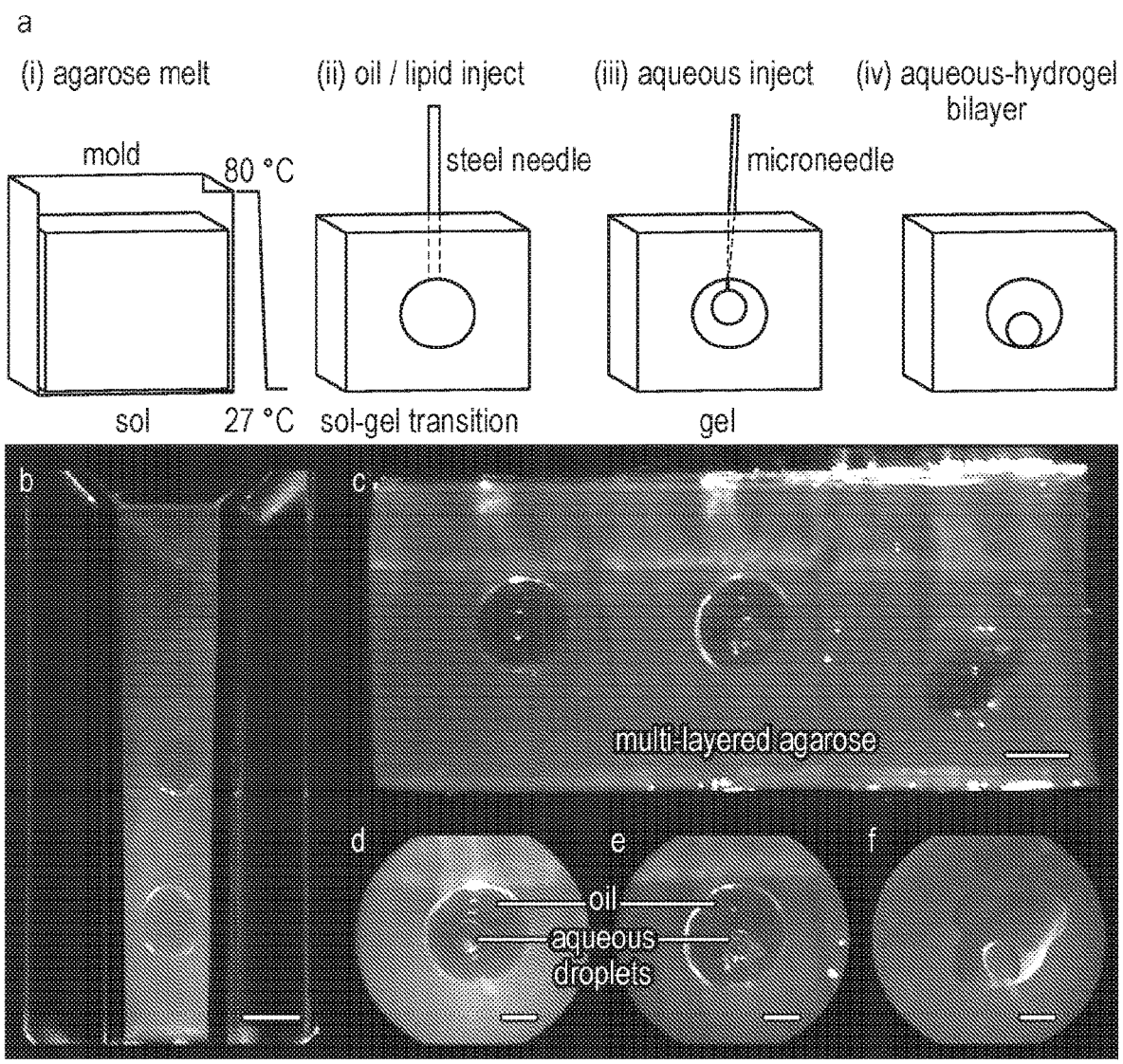
FIG. 2 shows images of multiple aqueous droplets (proto-organelles) within oil volumes in a hydrogel, forming a model protocell.

The process was repeated sequentially to construct a protocell comprising three proto-organelles, as illustrated in FIG. 2 (b). This series of three proto-organelles represents a 2D-network of compartments. A 3-tier agarose block was formed in a cuvette (coloured with water soluble dyes; bottom layer with pyranine, the middle layer without any dye, and the uppermost layer with rhodamine). The hydrogel layers were formed sequentially encapsulating an oil drop after each layer, as shown in FIG. 2 (c) The hydrogel block could be easily removed from the cuvette after complete gelation. The oil droplets were then accessible for injecting aqueous droplets using a microneedle giving a model protocell, as shown in FIG. 2, images d to f, which are enlarged images of the aqueous droplets in the three separate compartments. The gel matrix thus produced is an example of model protocell (ii) in FIG. 1).

Example 3: Encapsulation of Multiple Aqueous Droplets in a Volume of Hydrophobic Medium Assemblies of aqueous droplets in hydrogel as protocell models were made by inserting multiple aqueous droplets into a hydrogel encased oil droplets. The results are illustrated in FIG. 3. Stable aqueous droplet assemblies (solid green spheres) were made of (a) 2, (b) 3, (c) 4, (d) 5 aqueous droplets in hydrogel encased oil droplets (green circles demarcate the oil boundaries). Each of these oil droplet enclosures can be viewed as protocells where the aqueous droplets are the proto-organelles (an example of model protocell (iii) in FIG. 1). As is shown in images (e) and (f) in FIG. 3, the droplet sizes and the numbers could be varied as required. Image (g) shows a 3D assembly of aqueous droplets containing >40 droplets. Image (h) shows three oil droplets in a single piece of hydrogel containing different network geometries of aqueous droplet networks. This collection of protocells can be regarded as a prototissue model (cf. (iii) in FIG. 1). Image (i) is a side-view showing aqueous droplets interfacing with an agarose surface through stable lipid bilayers at the aqueous-hydrogel interface. The aqueous droplets contained 10 mM pyranine.

FIG. 3 contains scale bars on each image therein as follows: (a-h) 1 mm; (i) 100 µm.

The networks of proto-organelles shown in FIG. 3 (a-f) are 2D networks. A stable 3D network of proto-organelles inside an oil compartment encapsulated in hydrogel is shown in FIG. 3g. The aqueous droplet networks in three separate oil compartments, i.e., protocells, encapsulated in the same hydrogel shown in FIG. 3h form a prototissue.

Figure 4:
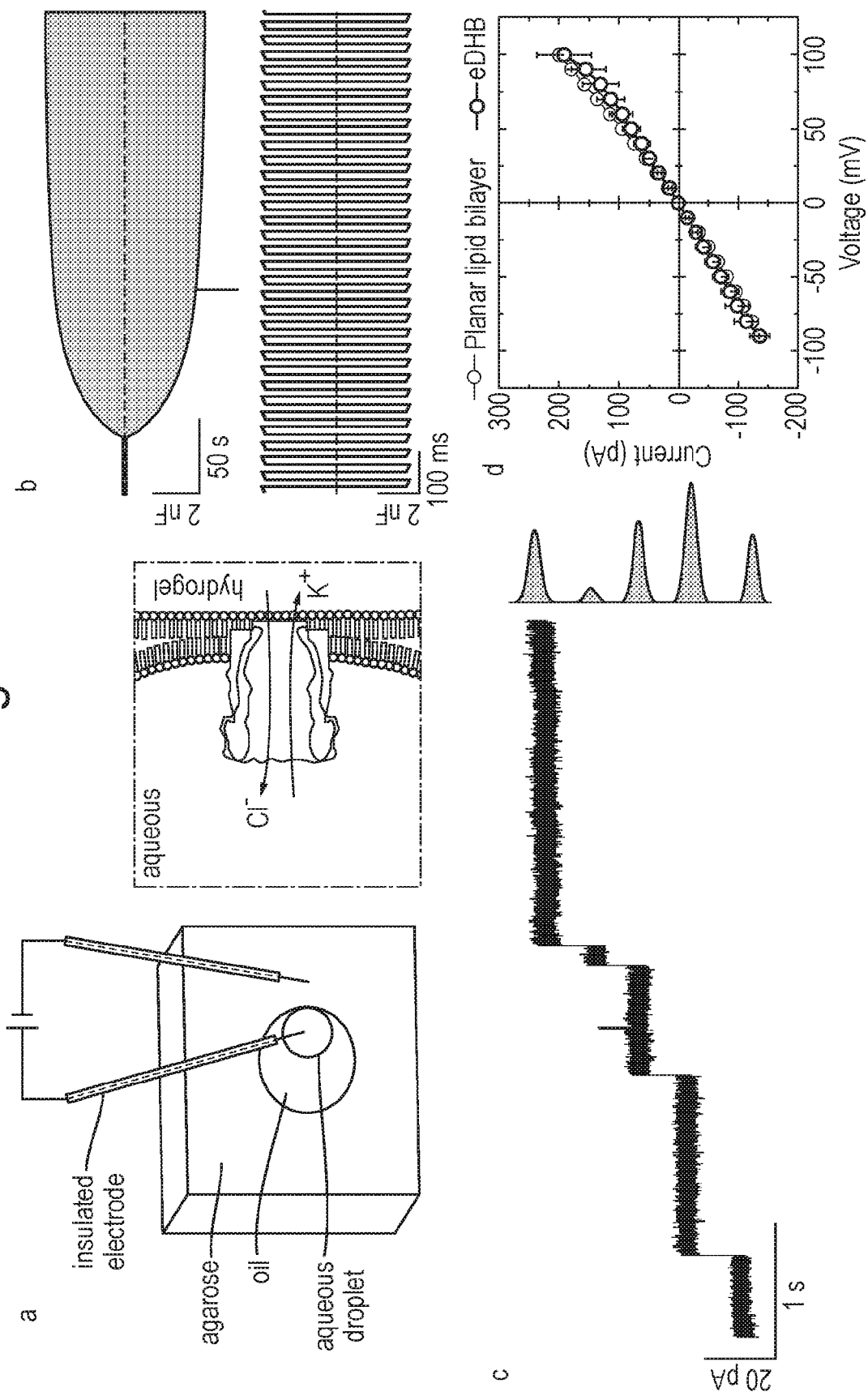
FIG. 4 illustrates the formation of bilayers in the compartments of the invention. The insertion of Cytolysin A and α-hemolysin into these bilayers is also shown, as observed by a step-wise increase in electrical current across the bilayer. The transport of human thrombin through such pores is also shown.
Figure 4:
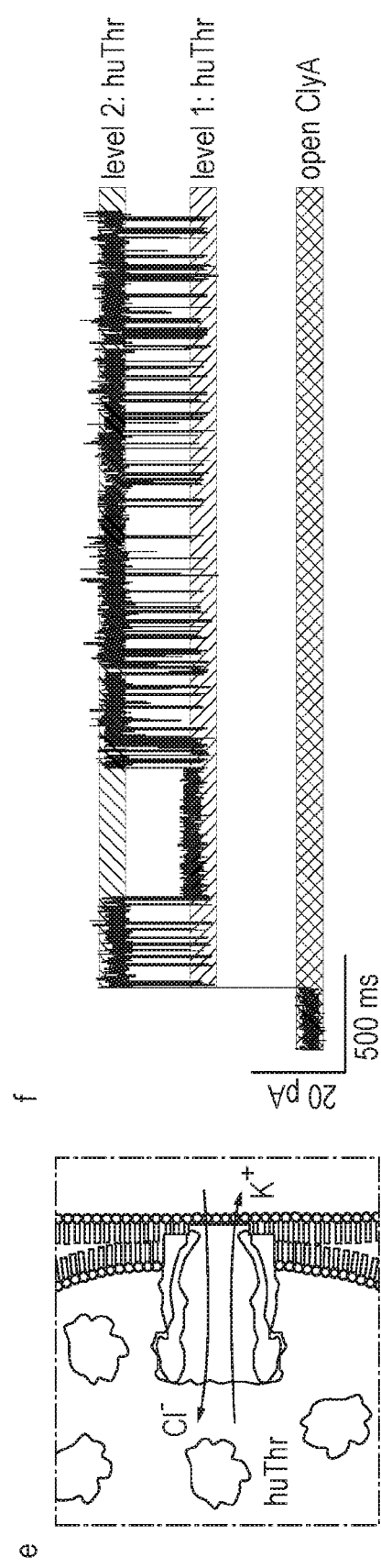

Example 4: Illustration that Encapsulated Droplets in Hydrogel (Proto-Organelles) are Functional Experiments illustrating the formation of a lipid bilayer comprising (i) an inner layer of amphipathic molecules at the interface of an encapsulated aqueous droplet and a volume of hydrophobic medium and (ii) an outer layer of amphipathic molecules at the interface between the volume of hydrophobic medium and an external hydrogel were performed. The method is described in the "experimental methods" section above and illustrated in FIGS. 4(a) and (b). Briefly, using a microneedle syringe, an aqueous droplet was injected inside the oil volume, and transferred at the end of an insulated Ag/AgCl electrode pierced through the hydrogel. Another insulated Ag/AgCl electrode was inserted in the hydrogel block (FIG. 4A). The droplet was brought into contact with the hydrogel surface with micrometer precision using a micromanipulator (FIG. 4, Image a). Bilayer formation was deduced by an increase in the capacitance (FIG. 4, Image b).

The experimental setup is shown in FIG. 4A. FIG. 4A (a) is a diagram showing the formation of a bilayer between the edges of the aqueous droplet and the volume of hydrophobic medium for electrical recording. A compartment was formed by injecting a specific volume of oil into the hydrogel. An insulated electrode was then inserted inside the oil, and an aqueous droplet transferred onto the electrode using a microneedle. Another insulated electrode was inserted in the hydrogel and the electrodes connected to an amplifier. FIG. 4A (b) is a photograph of an insulated electrode with dimensions. The system could also be used to form bilayers comprising (i) a layer of amphipathic molecules at an interface between an aqueous droplet and a hydrophobic medium and (ii) a layer of amphipathic molecules at an interface between a volume of hydrophobic medium and an aqueous layer.

FIG. 4A (c) is an image of two electrodes inserted inside the same oil volume. FIG. 4A (d) shows aqueous droplets transferred onto the electrodes and brought together using a micromanipulator to form a droplet interface bilayer. FIG. 4A (e) shows droplet-hydrogel bilayers comprising (i) a layer of amphipathic molecules at an interface between an aqueous droplet and an oil volume and (ii) a layer of amphipathic molecules at an interface between an oil volume and a hydrogel could be formed in two closely spaced oil volumes to give double bilayers. Stable bilayers with both DPhPC and porcine brain total lipid extract could be formed.

It was found that lipid-monolayer encased aqueous droplets encapsulated in hydrogel were capable of forming stable bilayers at the aqueous-hydrogel interface as determined electrically by an increase in the electrical capacitance, FIG. 4 (b).

Previously, it has been shown that bilayers formed between two droplets (convex-convex contact), between a droplet and a hydrogel (convex-flat contact), or two hydrogel pieces (flat-flat, convex-flat, convex-convex contacts), are capable of hosting protein nanopores and ion channels. A bilayer of a proto-organelle in a compartment according to the present invention was formed between a concave aqueous droplet and a concave hydrogel surface. The bilayers were conducive to the insertion of membrane pores like α-hemolysin (not shown) and ClyA observed as the signature step-wise increase in the electrical current, FIG. 4 (c). Conductance of ClyA inserted in the hydrogel-encapsulated proto-organelle bilayer (1.9±0.3 nS; n=5) was similar to the ClyA conductance measured in a conventional planar lipid bilayer (1.79±0.04 nS; n=3, FIG. 4(d)).

FIG. 4 (d) shows the I-V curve of ClyA insertion in an encapsulated proto-organelle bilayer (shown in red circles) was comparable to that of a planar lipid bilayer (shown in black circles), suggesting the stable insertion of the pores in the hydrogel platform. Thus, the geometry of the contact surfaces did not affect the integrity of the bilayer, and the assembly of the membrane pores in the lipid bilayer.

The proper assembly of ClyA into nanopores at a bilayer is illustrated in FIG. 4 (e). The stability of the ClyA pore was further ascertained by monitoring the binding kinetics of human thrombin (huThr) from the cis entrance of the ClyA pore. An aqueous droplet with huThr and ClyA was transferred onto an Ag/AgCl electrode in an oil chamber inside hydrogel. Bilayer formation between the droplet and the hydrogel and subsequent nanopore insertion was monitored electrically. Transient closure of a single ClyA pore, denoting the entry and exit of huThr, was measured. The transient kinetics of huThr blocking of the pore are shown in FIG. 4 (f). huThr has two definite levels inside ClyA nanopores; at −35 mV, $I_{RES}$ of level 1 is 53.2%±1.6% (N=3, n=263; where N is the number of experiments and n is the number of events) and of level 2 is 21.5%±2% (n=265). The measured values were in good agreement with those determined in planar lipid bilayers (Holden et al., "Functional bionetworks from nanoliter water droplets", J. Am. Chem. Soc. 129, 8650-8655 (2007)).

Example 5: Electrical Communication Between Proto-Organelles of a Protocell

Example 5 demonstrates that oil encapsulation inside hydrogel affords the possibility of controlled compartmentalization and making abutting lipid bilayers. This is key in demonstrating inter-organelle electrical communication. Aqueous droplet-hydrogel bilayers were formed in adjacent oil compartments (FIG. 5, FIG. 4A image (e)).

Figure 10:
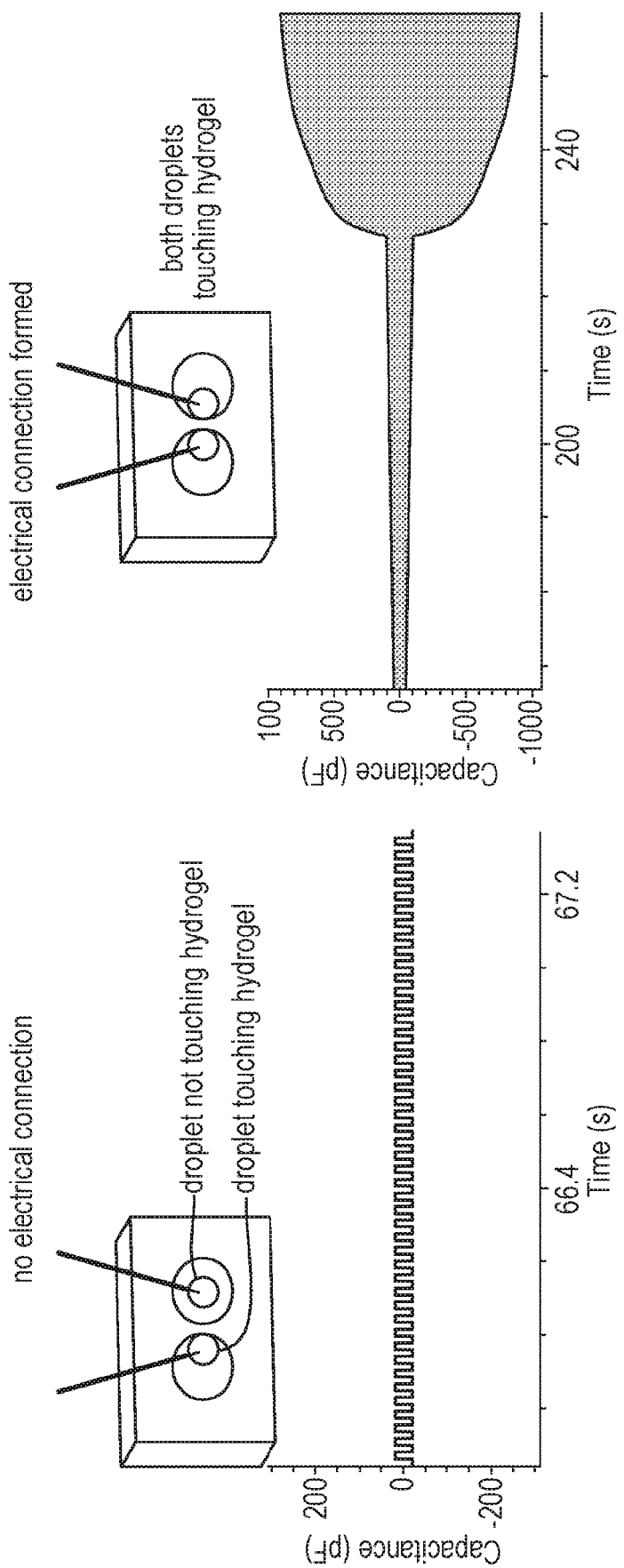
FIG. 10 shows the formation of adjacent bilayers, and the capacitance increase observed when two such bilayers contact one another and complete an electrical circuit.

Owing to the firm enclosure of oil droplets in a hydrogel, it was possible to control the distance between the oil droplets intervened by a thin layer of agarose (100-200 μm). Two aqueous droplets in each oil chamber were controlled using a micromanipulator to form contiguous bilayers. The simultaneous formation of the two bilayers was confirmed by measuring an increase in electrical electrical capacitance (discussed in Example 10, below, and shown in FIG. 10). Step-wise ClyA insertion was observed in the juxtaposed bilayers; the conductance decreased with each insertion as expected for resistors in series (shown in FIG. 10; see FIG. 5A for electrical model, discussed below). Studies were also performed using lysozyme (results not included here).

First, electrical connection was formed only between one aqueous droplet containing ClyA (1-10 ng mL$^{-1}$) and the hydrogel by inserting two insulated electrodes each in the aqueous droplet and the hydrogel (FIG. 5 (a)). The unitary conductance of ClyA was found to be 1.9±0.3 nS (FIG. 5 (c)). Next, in the same experimental set-up, an electrical connection was established between the two droplets (both containing 1-10 ng mL$^{-1}$ ClyA) by inserting both the electrodes in the two droplets (FIG. 5 (b)). As expected in the case of two bilayers in series, the amplitude of the current through the pore decreased with each ClyA insertion (FIG. 5 (d)). In FIG. 5, Image (e), the top panel shows the electrical model where single ClyA pores (resistors) are inserted in two adjacent bilayers (capacitors). The bottom panel shows the insertion of an additional ClyA pore in the left bilayer. The step-size of individual insertion can be modelled as follows.

Bilayer formation and nanopore insertion in the hydrogel-enclosed droplet system can be treated as an electrical circuit in which droplet-hydrogel bilayers are capacitors, ClyA pores are resistors, and the hydrogel between the two electrical circuits is considered as a conductive junction. In the case of a single droplet-hydrogel bilayer the insertion of each pore is characterized by a current step of the same magnitude since the current results from single resistors (pores) inserting sequentially in a capacitor (bilayer). In the case of two bilayers placed adjacent to each other, the current steps are variable.

The case of two adjacent bilayers is considered in this Example. The two bilayers are formed by two aqueous droplets, A and B, with the hydrogel (the set-up shown in, for instance, FIG. 5 (a)). The resistance of the nanopores inserted in the two droplet-hydrogel bilayers is denoted as $R_{SS}$ and $R_B$, respectively (FIG. 5(e)). Because the two bilayers are connected through the hydrogel, they may be considered as two electrical circuits connected in series. Applying rules from the Kirchhoff's Circuit Law and Ohm's Law, basic equations for the droplet-hydrogel adjacent bilayers system are derived.

The net resistance, $R_t$, is the total resistance of the two series circuits (bilayers) with resistors $R_{ss}$ and $R_B$, $$R_t = R_{SS} + R_B \quad (1)$$

Pore insertion in the adjacent bilayer system can be characterized by two types of current; steady-state current, $I_{SS}$, and insertion current, $I_{insert}(t)$. $I_{SS}$ is the current after pore insertion, whereas $I_{insert}(t)$ is the current at the moment of pore insertion.

The steady-state current through the pores in adjacent bilayers is given by Ohm's Law, I=V/R. Therefore, $I_{SS}$, after the insertion of a pore under an applied voltage, $V_{CC}$, is, $$I_{SS} = \frac{V_{CC}}{R_{SS} + R_B} \quad (2)$$

From equation (2) it is expected that $I_{SS}$ resulting from the two bilayer system is less than the one from one bilayer with the same type of pores (resistors). The average $I_{SS}$ of single pores in the one bilayer system is −67±11 pA at −35 mV (FIG. 5(c)). This is in agreement with the conductance of ClyA nanopores (Soskine et al., "Tuning the size and properties of ClyA nanopores assisted by directed evolution", J. Am. Chem. Soc. 135, 13456-13463 (2013)). In the case of two adjacent bilayers the average $I_{SS}$ is −29.5±34 pA at −35 mV (FIG. 5(d)).

In order to obtain a model which describes the current during the continuous insertion of pores in the two adjacent bilayer system, i.e., $I_{insert}(t)$, more resistors have to be added in the electrical circuits. Equation (3) describes the current at the moment of insertion ($I_{insert}(t)$), $$I_{insert}(t) = \alpha + \beta \exp(-\gamma t) \quad (3)$$

where α is the steady-state net current through two adjacent bilayers when an additional pore inserts; β is the initial current deviation from a immediately after a pore insertion; and γ is the inverse of exponential decay time constant for pore insertion event.

Figure 5A:
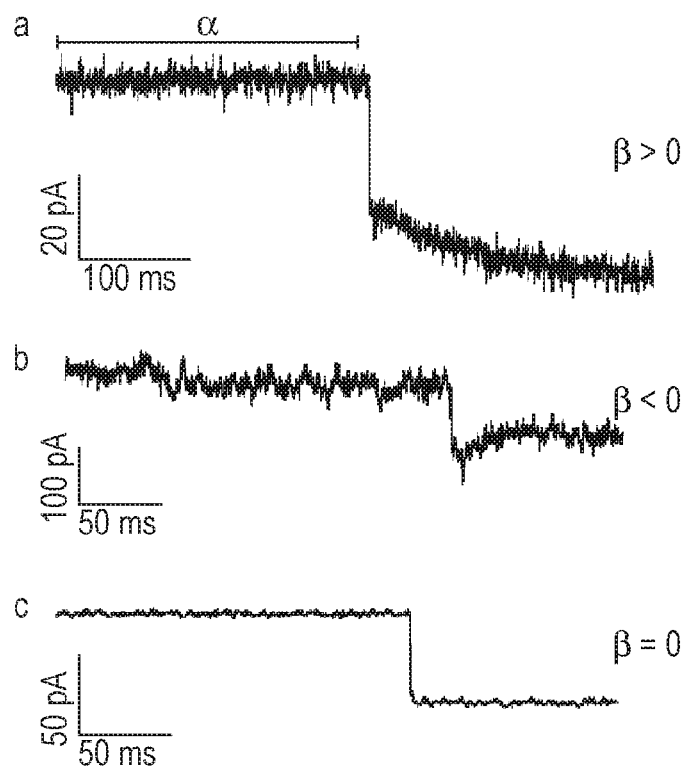
FIGS. 5A and 5B show electrical current measurements taken across pairs of bilayers, and the variation of the current with the orientation and number of ClyA pores in each bilayer.

The numerical solution of equation (3) gives 3 possibilities for β; =0, >0 or <0. These values depend on the ratio of the number of pores inserted in each bilayer. Correspondingly, in experiments on the present system the 3 different possibilities denoting the insertion of ClyA in adjacent bilayers were observed. These are shown in FIG. 5A.

From equations (2) and (3) it is possible to determine the insertion configurations of pores in bilayers A and B. From equation (3), if β=0, $I_{insert}(t)$ is equal to α, i.e., it is equal to the steady-state current. Thus, equation (2) can be used to determine the number of pore insertions and where each new pore inserts in the two bilayers. However, to be able to use equation (2) it is necessary to determine the resistance of ClyA nanopores.

The conductance of a ClyA nanopores at 35 mV is 2.03 nS and 1.79 nS respectively (Soskine et al., "Tuning the size and properties of ClyA nanopores assisted by directed evolution", J Am. Chem. Soc. 135, 13456-13463 (2013)). The resistance of the ClyA pore at ±35 mV therefore is 0.55 GΩ and 0.49 GΩ, respectively. This difference in the resistance at the same voltage is due to the rectification of the nanopore. In the adjacent bilayer system, ClyA nanopores inserted in bilayer B will have a different orientation than the pores inserted in bilayer A. Therefore the resistances of the pores in the two bilayers will have different values at the same voltage due to the rectification properties of ClyA. For example, at −35 mV, $R_{SS}$=0.55 nΩ in case of bilayer A (connected to the ground electrode) and $R_B$=0.49 nΩ for the pore in bilayer B (connected to the active electrode).

If more than one pore is inserted in any bilayer of the two adjacent bilayers, then those pores are resistors connected in parallel. If a new pore R is inserted in bilayer A; $R_{SS}$ is resistance of bilayer A before insertion of the new pore R, then the total resistance, $R_{insert}$, of bilayer A is:

$$R_A = R_{insert} \| R_{SS} \quad R_A = \frac{R_{insert} \times R_{SS}}{R_{insert} + R_{SS}} \quad (4)$$

The value of the current steps denotes the configuration of the pores in the bilayer. The step-size in FIG. 5B (a) denotes a pore in configuration (1A, 1B), i.e., a single pore is inserted in bilayer A and another pore in bilayer B. The change of 33.9 pA upon pore insertion observed experimentally agrees with the calculated value of 33.6 pA (1A, 1B) from equation (2).

Figure 5B:
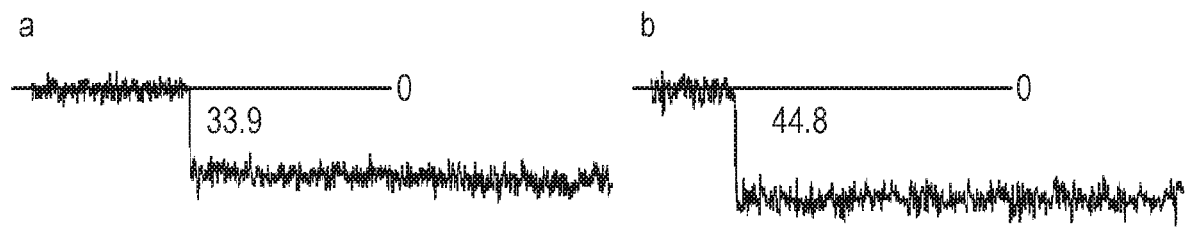

Another case in which two pores inserted in bilayer B and one pore in bilayer A, i.e., configuration (2B, 1A), the current calculated using equations (2) and (4) is equal to −44.3 pA which is in agreement with the current step of 44.8 pA shown in FIG. 5B (b). If the configuration was (1B, 2A) then the expected current would be 45.7 pA.

Example 6: Formation of a Nested Compartment

To demonstrate the versatility of the system, a compartment comprising a volume of oil was further engineered by introducing an aqueous layer between the oil and hydrogel. The method is shown diagrammatically in FIG. 6. First, an oil chamber was formed inside the hydrogel (FIG. 6 (a)). In this step, an oil-lipid mix was encapsulated at the hydrogel gelling transition temperature. Next, instead of injecting a small aqueous volume to form a droplet (typically ~50 nL), a large aqueous volume (~500 μL) was injected in the oil (FIG. 6 (b, c)). Instead of forming a stable bilayer at the oil/hydrogel interface, the injection of a large volume of aqueous medium caused the aqueous medium to engulf the oil volume and form an intervening layer between the hydrogel and the oil. FIG. 6 (d) shows a real image top view of such an oil volume engulfed in an aqueous layer, and FIG. 6(c) shows a cartoon of this image. A small aqueous droplet could still be injected inside the oil droplet (the aqueous droplet representing a proto-organelle) such that the aqueous droplet was stabilized by a bilayer at the oil/aqueous layer interface, FIG. 6 (e). FIG. 6 (f) is a top view real image of the cartoon shown in (e).

FIGS. 6 (d) and (f) contain scale bars representing 1 mm.

Example 7: Stability of Hydrogel-Encapsulated Aqueous Droplets in Different Assemblies Assemblies with 2, 4, 6 and 8 aqueous droplets therein (400 μm diameter, containing 5 mg mL$^{-1}$ DPhPC) were injected into compartments of an oil/lipid mixture (7.5 mg mL-1 DPhPC) encapsulated in different hydrogel blocks and their stability was monitored. The plot in FIG. 7 shows the time taken for the first aqueous droplet to fuse with the hydrogel or with another aqueous droplet. The remaining droplets were still intact. As shown, the minimum stability of the first droplet ranged between 1 h up to 81 h. With increasing size of the assemblies the maximal stability of the first droplet decreased from ~80 h to ~30 h.

It was further found that the hydrogel-encapsulated aqueous droplets were stable, i.e., they did not fuse with the hydrogel, to reasonable mechanical motion. For example, carrying the hydrogel piece from one lab to another (~25 m), or rotating a hydrogel did not destroy the aqueous droplets.

The origin of the droplet stability may be attributed to be the lipid bilayer at the aqueous-hydrogel interface. The lipids in the oil coat the inner surface of the hydrogel enclosure to form a lipid monolayer; the aqueous droplets with liposomes too are encased by lipid monolayers when injected in the oil. Upon settling on the lipid monolayer-coated hydrogel surface, the contact interface between the aqueous droplets and the hydrogel is stabilized by the formation of a lipid bilayer (as illustrated in FIGS. 1 and 2). This stabilization may be attributed to reaching a free energy minimum in a complex energy landscape as in the case of multisomes.

Example 8: Stable Droplet-Hydrogel Bilayer Formation

Figure 8:
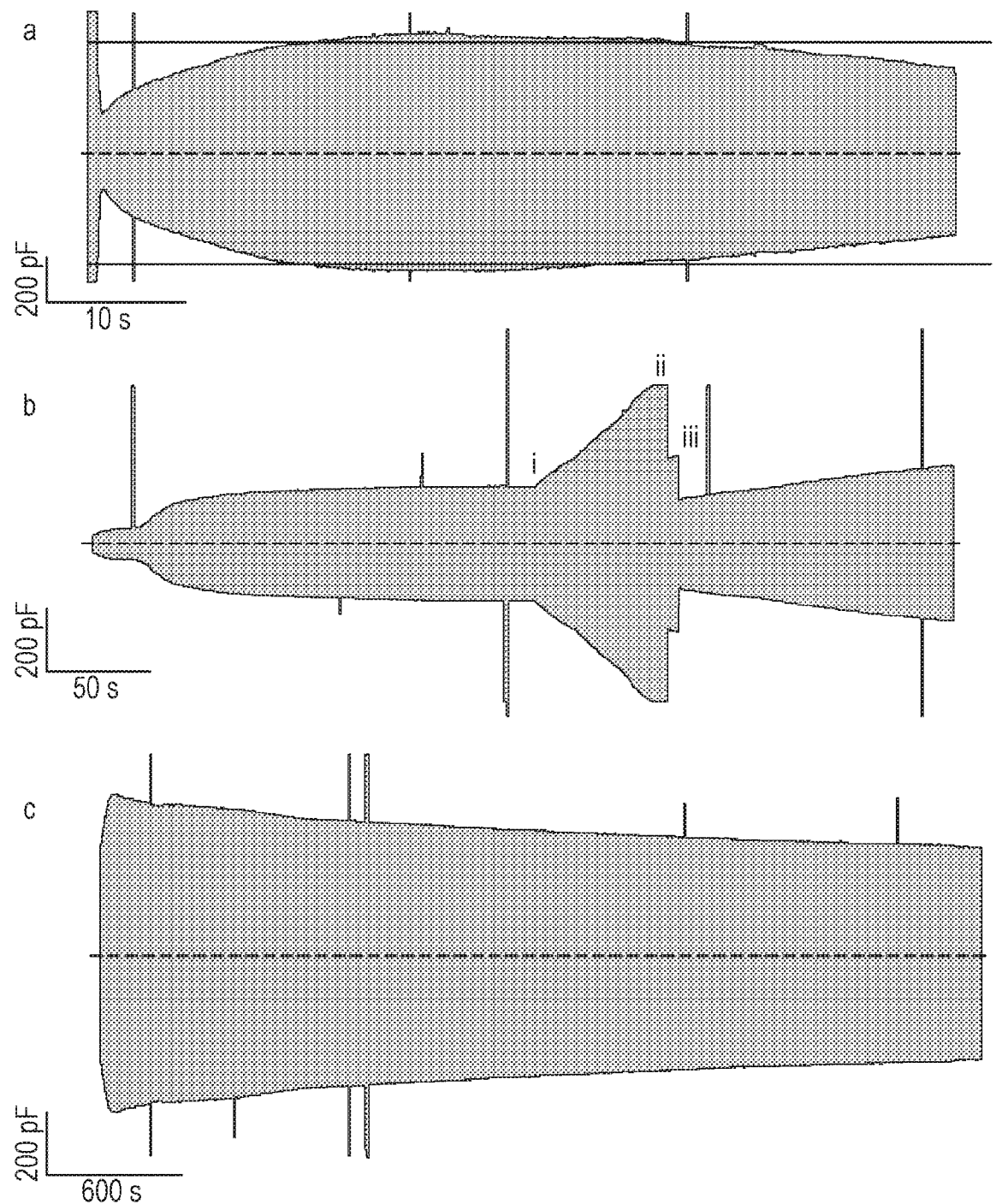
FIG. 8 shows capacitance measurement performed on bilayers according to the invention. Capacitance increases when a bilayer is formed (FIG. 8(*a*)), increases or decreases with the area of the bilayer (FIG. 8(*b*)) and is stable over a long period, indicating that the bilayer is stable for that period (FIG. 8(*c*)).

Capacitance experiments were performed using the experimental set-up shown in FIG. 4A. The results are shown in FIG. 8. FIG. 8 (a) shows a capacitance increase indicating the formation of a bilayer between an aqueous droplet and hydrogel at +50 mV. The bilayers formed were stable for at least 1 h at +50 mV. The encapsulation of droplets with stable bilayers formed the basis of proto-organelles.

FIG. 8 (b) shows how the capacitance due to the bilayer can be affected by manipulating the bilayer. The bilayer area could be increased (i) or decreased (ii, iii) by pushing or pulling the encapsulated aqueous droplet against the hydrogel wall, respectively. The rise in capacitance at point (i) in FIG. 8(b), and the drop at points (ii) and (iii), correspond to such manipulation of the bilayer.

FIG. 8 (c) shows a capacitance recording of a bilayer taken over a period of over an hour. The smooth and minor decrease shows that the bilayer is stable for >1 h under an applied potential of +50 mV.

Example 9: Diffusion Through a Bilayer Facilitated by a Protein Pore

Figure 9:
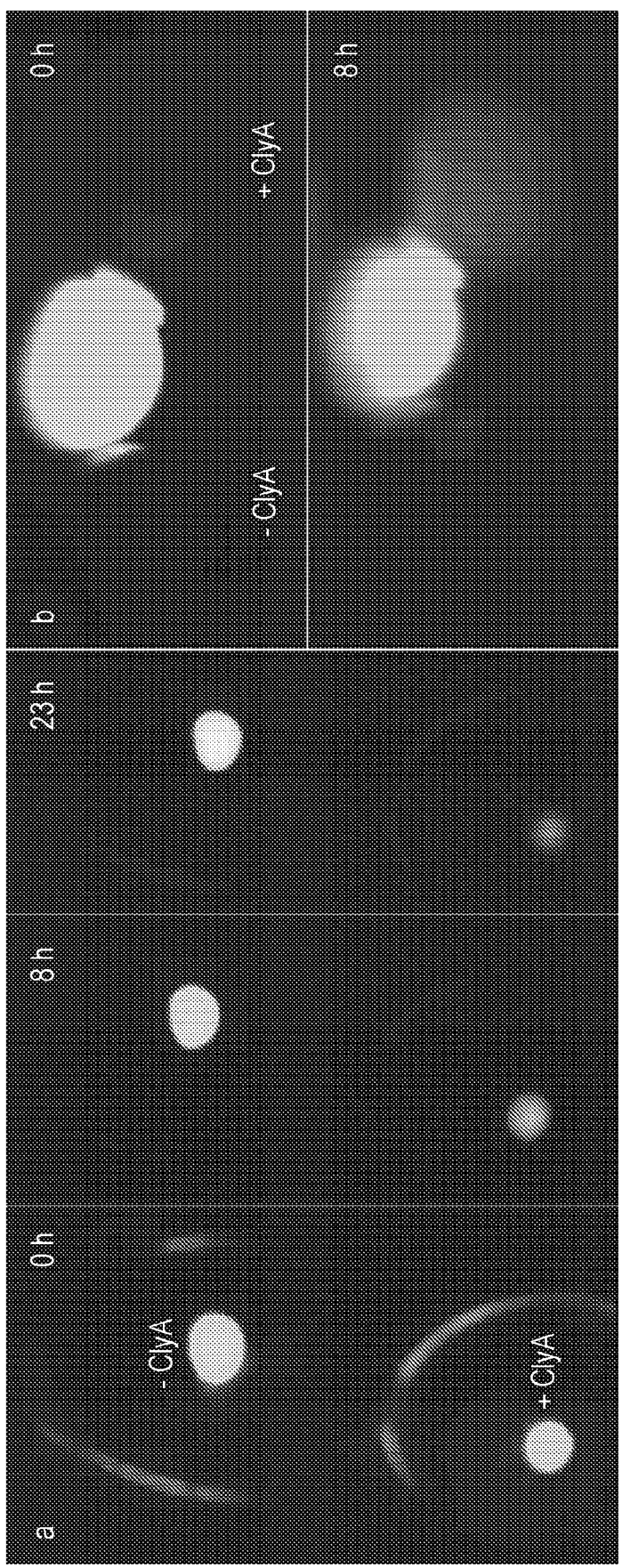
FIG. 9 shows the effects of inserting ClyA pores into a bilayer at the interface between an aqueous droplet and an oil volume. The ClyA pore allows pyranine to diffuse out of, or into, the aqueous droplet; droplets without a ClyA pore do not transfer pyranine in or out.

Functional proto-organelle bilayers were formed using ClyA present in a bilayer. The ClyA pore enables transport into and out of the cell, as is illustrated in FIG. 9, which shows that ClyA pores in a proto-organelle bilayer were capable of sustaining diffusion of a small molecule (pyranine dye).

A multi-compartment hydrogel was formed by encapsulating two oil volumes inside the same hydrogel piece. FIG. 9 (a) shows two aqueous droplets containing pyranine (10 mM in 150 mM NaCl, 10 mM Tris HCl, pH 7.5). The aqueous droplets appear as solid green spheres in FIG. 9. The aqueous solution containing pyranine was injected in two separate oil volumes (the oil volumes can be seen as a green outline in FIG. 9(a)). In one droplet, labelled +ClyA, ClyA (60 μg mL$^1$) was added but not in the other (labelled –ClyA). Insertion of ClyA pores in the bilayer (at the interface between the oil volume and the aqueous droplet) enabled diffusion of pyranine outside the droplet (into the hydrogel) as seen by a decrease in the green intensity after 8 and 23 hours in FIG. 9 (a). No decrease in intensity was observed in the droplet without ClyA over the same duration (~23 h).

Also demonstrated was intra- and inter-communication between proto-organelles in a protocell. For intra-communication, a linear array of 3 aqueous droplets (proto-organelles) in oil encapsulated in a hydrogel block (specifically agarose) was formed; the middle droplet contained pyranine, one droplet contained ClyA and one did not. The results are shown in FIG. 9 (b). The middle droplet with pyranine (green) did not contain ClyA. The droplet on the left was also without ClyA (–ClyA), whereas ClyA was incorporated in the droplet on the right (+ClyA, 40 μg mL$^{-1}$). The interface with +ClyA droplet promoted pyranine diffusion turning the droplet green over 8 h. The –ClyA droplet did not show an increase in green intensity during the same time. Thus pyranine diffusion was observed only across the bilayer between the droplet with pyranine to the droplet containing ClyA.

Example 10: Simultaneous Formation of Adjacent Bilayers

Two aqueous droplets were transferred onto insulated electrodes inserted into two oil volumes next to each other. The setup is shown diagrammatically in FIG. 10. When only one droplet was used to form a bilayer by touching the hydrogel using a micromanipulator, no increase in the electrical capacitance was observed across the electrodes (left-hand side of FIG. 10). However, upon touching the other aqueous droplet to the hydrogel around the oil volume, the circuit was complete and an increase in the electrical capacitance was observed indicating the formation of two bilayers (right-hand side of FIG. 10).

The invention claimed is:

1. A multi-compartmentalised gel matrix comprising a gel matrix and a plurality of compartments, wherein each compartment comprises:
   a volume of a hydrophobic medium;
   an outer layer of amphipathic molecules around the volume of hydrophobic medium;
   an aqueous droplet in the volume of hydrophobic medium; and
   an inner layer of amphipathic molecules at an interface between the aqueous droplet and the hydrophobic medium.

2. A multi-compartmentalised gel matrix according to claim 1 wherein the outer layer of amphipathic molecules in at least one of the compartments is at an interface between the gel matrix and the volume of hydrophobic medium.

3. A multi-compartmentalised gel matrix according to claim 1 wherein the hydrophobic medium in at least one of the compartments contains a plurality of aqueous droplets.

4. A multi-compartmentalised gel matrix according to claim 1, wherein a part of the outer layer of amphipathic molecules contacts a part of the inner layer of amphipathic molecules in at least one of the compartments.

5. A multi-compartmentalised gel matrix according to claim 4, wherein the parts of the outer layer of amphipathic molecules and the inner layer of amphipathic molecules that are in contact form a bilayer.

6. A multi-compartmentalised gel matrix according to claim 5, wherein there are two bilayers which are positioned next to one another and together form a double bilayer.

7. A multi-compartmentalised gel matrix according to claim 6 wherein each bilayer within the double bilayer comprises:
(a) a layer of amphipathic molecules at an interface between an aqueous droplet and the volume of hydrophobic medium; and
(b) a layer of amphipathic molecules at an interface between the gel matrix and the volume of hydrophobic medium.

8. A multi-compartmentalised gel matrix according to claim 6 wherein the pair of bilayers are separated by a region of the gel matrix.

9. A multi-compartmentalised gel matrix according to claim 8 wherein the region of the gel matrix that separates the bilayers is 10 nm thick or less.

10. A compartmentalised gel matrix comprising a gel matrix and a nested compartment, wherein the nested compartment comprises:
a volume of a hydrophobic medium;
an aqueous droplet in the hydrophobic medium;
an aqueous layer around the volume of hydrophobic medium;
an inner layer of amphipathic molecules at the interface between the aqueous droplet and the hydrophobic medium; and
an outer layer of amphipathic molecules at the interface between the aqueous layer and the volume of hydrophobic medium.

11. A compartmentalised gel matrix according to claim 10 wherein the volume of hydrophobic medium contains a plurality of aqueous droplets.

12. A compartmentalised gel matrix according to claim 10, wherein a part of the outer layer of amphipathic molecules contacts a part of the inner layer of amphipathic molecules.

13. A compartmentalised gel matrix according to claim 12, wherein the parts of the outer layer of amphipathic molecules and the inner layer of amphipathic molecules that are in contact form a bilayer.

14. A multi-compartmentalised gel matrix according to claim 1 wherein at least one of the compartments comprises an aqueous layer around the volume of hydrophobic medium and said compartment is a nested compartment comprising:
a volume of a hydrophobic medium;
an aqueous droplet in the hydrophobic medium;
an aqueous layer around the volume of hydrophobic medium;
an inner layer of amphipathic molecules at the interface between the aqueous droplet and the hydrophobic medium; and
an outer layer of amphipathic molecules at the interface between the aqueous layer and the volume of hydrophobic medium.

15. A multi-compartmentalised gel matrix according to claim 14 wherein a part of the outer layer of amphipathic molecules contacts a part of the inner layer of amphipathic molecules in at least one of the compartments, and the parts of the outer layer of amphipathic molecules and the inner layer of amphipathic molecules that are in contact form a bilayer, and wherein the multi-compartmentalised gel matrix comprises two such bilayers which are positioned next to one another and together form a double bilayer, wherein one bilayer within the double bilayer comprises:
(a) a layer of amphipathic molecules at an interface between an aqueous droplet and a volume of hydrophobic medium; and
(b) a layer of amphipathic molecules at an interface between the gel matrix and the volume of hydrophobic medium;
and the second bilayer within the double bilayer comprises:
(a) a layer of amphipathic molecules at an interface between an aqueous droplet and a volume of hydrophobic medium; and
(b) a layer of amphipathic molecules at an interface between the aqueous layer and the volume of hydrophobic medium.

16. A multi-compartmentalised gel matrix according to claim 1 wherein the compartments form a network.

17. A multi-compartmentalised gel matrix or a compartmentalised gel matrix according to claim 5 comprising a bilayer, wherein:
(a) the bilayer is a lipid bilayer; and/or
(b) the bilayer comprises a membrane protein; and/or
(c) the bilayer comprises a protein pore; and/or
(d) the bilayer comprises cytolysin A.

18. A multi-compartmentalised gel matrix or compartmentalised gel matrix according to claim 1, wherein the hydrophobic medium comprises or consists of an oil.

19. A multi-compartmentalised gel matrix or compartmentalised gel matrix according to claim 1 wherein:
(a) the gel matrix comprises a biocompatible gel; and/or
(b) the gel matrix comprises or consists of a hydrogel; and/or
(c) the gel matrix comprises two or more gel regions, optionally wherein the gel regions comprise different gels.

20. A multi-compartmentalised gel matrix or compartmentalised gel matrix according to claim 1 comprising an active agent, optionally wherein the gel matrix is functionalised with the active agent; further optionally wherein the active agent is present within a compartment, within the aqueous medium or the hydrophobic medium.

21. A method of manufacturing a multi-compartmentalised gel matrix, the method comprising:
(i) inserting a volume of a hydrophobic medium into an incompletely gelled gel precursor via an inserting means to form a compartment;
(ii) repeating (i) one or more times to provide a plurality of compartments in the gel precursor;
(iii) gelling the gel precursor;
(iv) inserting a volume of an aqueous medium into one of the plurality of compartments via an inserting means to form an aqueous droplet therein; and
(v) repeating (iv) a plurality of times to provide an aqueous droplet in each compartment among the plurality of compartments.

22. A method of producing a multi-compartmentalised gel matrix according to claim 21 comprising one or more nested compartments, the method comprising:

(i) inserting a volume of a hydrophobic medium into an incompletely gelled gel precursor via an inserting means to form a compartment;
(ii) repeating (i) one or more times to provide a plurality of compartments in the gel precursor;
(iii) gelling the gel precursor;
(iv) inserting a volume of an aqueous medium into a said compartment via an inserting means to form an aqueous droplet therein;
(v) repeating (iv) a plurality of times to provide an aqueous droplet in each compartment among the plurality of compartments;
(vi) inserting a quantity of an aqueous medium in or near a volume of hydrophobic medium via an inserting means to form an engulfed volume of hydrophobic medium in a layer of aqueous medium; and
(vii) inserting a volume of an aqueous medium into the engulfed volume of hydrophobic medium via an inserting means to form an aqueous droplet therein.

23. The multi-compartmentalised gel matrix of claim 1, wherein the outer layer of amphipathic molecules and the inner layer of amphipathic molecules are monolayers of amphipathic molecules.

24. The compartmentalised gel matrix of claim 10, wherein the outer layer of amphipathic molecules and the inner layer of amphipathic molecules are monolayers of amphipathic molecules.

* * * * *